United States Patent
Lewicki et al.

(10) Patent No.: US 9,676,865 B2
(45) Date of Patent: *Jun. 13, 2017

(54) ANTIBODIES TO A NON-LIGAND BINDING REGION OF AT LEAST TWO NOTCH RECEPTORS

(71) Applicant: OncoMed Pharmaceuticals, Inc., Redwood City, CA (US)

(72) Inventors: John A. Lewicki, Los Gatos, CA (US); Austin L. Gurney, San Francisco, CA (US); Timothy Hoey, Hillsborough, CA (US); Wan-ching Yen, Foster City, CA (US); Sanjeev Satyal, San Carlos, CA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/308,371

(22) Filed: Jun. 18, 2014

(65) Prior Publication Data

US 2016/0053016 A1    Feb. 25, 2016

Related U.S. Application Data

(62) Division of application No. 13/773,921, filed on Feb. 22, 2013, now Pat. No. 8,784,811, which is a division of application No. 13/472,301, filed on May 15, 2012, now Pat. No. 8,404,237, which is a division of application No. 13/010,486, filed on Jan. 20, 2011, now Pat. No. 8,206,713, which is a division of application No. 11/806,472, filed on May 31, 2007, now Pat. No. 7,919,092.

(60) Provisional application No. 60/812,955, filed on Jun. 13, 2006, provisional application No. 60/879,336, filed on Jan. 9, 2007, provisional application No. 60/878,661, filed on Jan. 5, 2007.

(51) Int. Cl.

| | | |
|---|---|---|
| *C07K 16/18* | (2006.01) | |
| *C07K 16/28* | (2006.01) | |
| *C07K 16/30* | (2006.01) | |
| *A61K 39/395* | (2006.01) | |
| *A61K 45/06* | (2006.01) | |
| *A61N 5/10* | (2006.01) | |
| *C07K 14/705* | (2006.01) | |
| *C07K 14/715* | (2006.01) | |
| *A61K 39/00* | (2006.01) | |

(52) U.S. Cl.
CPC ........ *C07K 16/30* (2013.01); *A61K 39/39558* (2013.01); *A61K 45/06* (2013.01); *A61N 5/10* (2013.01); *C07K 16/18* (2013.01); *C07K 16/28* (2013.01); *C07K 16/3015* (2013.01); *C07K 16/3046* (2013.01); *A61K 2039/505* (2013.01); *A61K 2039/507* (2013.01); *C07K 2317/21* (2013.01); *C07K 2317/24* (2013.01); *C07K 2317/31* (2013.01); *C07K 2317/34* (2013.01); *C07K 2317/73* (2013.01); *C07K 2317/732* (2013.01); *C07K 2317/734* (2013.01); *C07K 2317/76* (2013.01); *C07K 2317/92* (2013.01)

(58) Field of Classification Search
CPC .......... A61K 2300/00; A61K 2039/505; A61K 39/39558; A61K 39/3955; A61K 39/395; A61K 38/177; C07K 2317/76; C07K 2317/73; C07K 16/2863; C07K 16/18; C07K 14/705; C07K 2316/96; C07K 16/00; C07K 16/2866
See application file for complete search history.

(56) References Cited

U.S. PATENT DOCUMENTS

| | | | |
|---|---|---|---|
| 4,676,980 A | 6/1987 | Segal et al. | |
| 5,648,464 A | 7/1997 | Artavanis-Tsakonas et al. | |
| 5,786,158 A | 7/1998 | Artavanis-Tsakonas et al. | |
| 5,789,195 A | 8/1998 | Artavanis-Tsakonas et al. | |
| 5,854,027 A | 12/1998 | Steipe et al. | |
| 6,004,528 A | 12/1999 | Bergstein | |

(Continued)

FOREIGN PATENT DOCUMENTS

| | | | |
|---|---|---|---|
| CA | 2343963 A1 | 4/2000 | |
| CN | 1242802 A | 1/2000 | |

(Continued)

OTHER PUBLICATIONS

Lee et al. Molecular cloning of agonistic and antagonistic monoclonal antibodies against human 4-1BB. Eur J Immunogenet 29: 449-452, 2002.*
Richter et al. Antagonistic TNF receptor one-specific antibody (ATROSAB): receptor binding and in vitro bioactivity. PLOS One 8(8): e72156, 2013.*
Rimm et al. J Cell Biol 111(No. 6 Pt 1): 2405-2416, 1990.*
Beerli, R.R. and Rader, C., "Mining Human Antibody Repertoires," mAbs 2(4):365-378, Landes Bioscience, United States (2010).
Chen, S-M., et al., "Suppression of the Notch Signaling Pathway by γ-Secretase Inhibitor GSI Inhibits Human Nasopharyngeal Carcinoma Cell Proliferation," Cancer Letters 306(1):76-84, Elsevier Ireland Ltd., Ireland (2011).

(Continued)

*Primary Examiner* — Bridget E Bunner
(74) *Attorney, Agent, or Firm* — Sterne, Kessler, Goldstein & Fox P.L.L.C.

(57) ABSTRACT

The present invention relates to compositions and methods for characterizing, diagnosing, and treating cancer. In particular the invention provides the means and methods for the diagnosis, characterization, prognosis and treatment of cancer and specifically targeting cancer stem cells. The present invention provides an antibody that specifically binds to a non-ligand binding region of the extracellular domain of a human NOTCH receptor and inhibits growth of tumor cells. The present invention further provides a method of treating cancer, the method comprising administering a therapeutically effective amount of an antibody that specifically binds to a non-ligand binding region of the extracellular domain of a human NOTCH receptor protein and inhibits growth of tumor cells.

12 Claims, 22 Drawing Sheets

(56) References Cited

U.S. PATENT DOCUMENTS

Figure 1A:
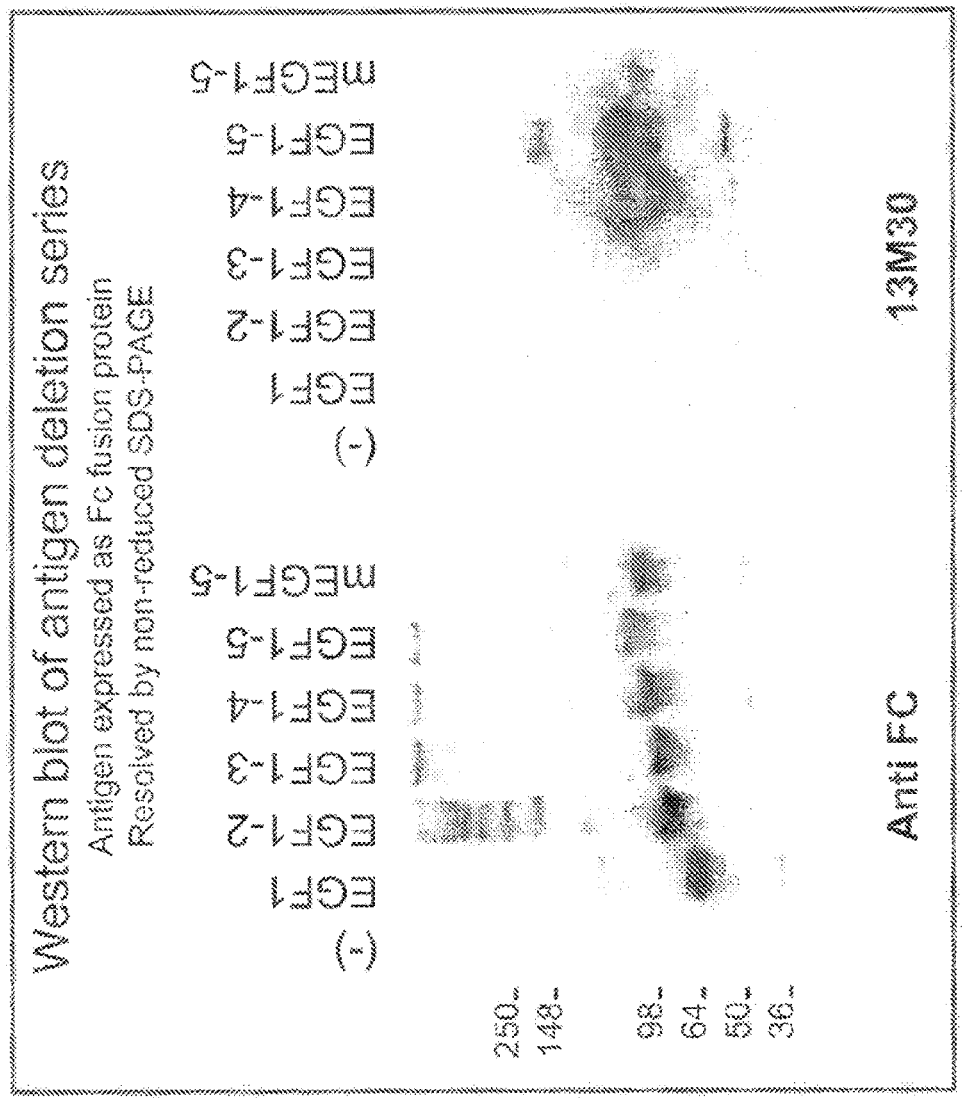

| | | |
|---|---|---|
| 6,080,588 A | 6/2000 | Glick |
| 6,083,904 A | 7/2000 | Artavanis-Tsakonas |
| 6,090,922 A | 7/2000 | Artavanis-Tsakonas et al. |
| 6,180,370 B1 | 1/2001 | Queen et al. |
| 6,379,925 B1 | 4/2002 | Kitajewski et al. |
| 6,537,775 B1 | 3/2003 | Tournier-Lasserve et al. |
| 6,689,744 B2 | 2/2004 | Gao et al. |
| 6,692,919 B1 | 2/2004 | Artavanis-Tsakonas et al. |
| 6,984,522 B2 | 1/2006 | Clarke et al. |
| 7,091,323 B2 | 8/2006 | Pan et al. |
| 7,115,360 B2 | 10/2006 | Clarke et al. |
| 7,282,203 B2 | 10/2007 | Coignet |
| 7,432,364 B2 | 10/2008 | Pan et al. |
| 7,632,926 B2 | 12/2009 | Kim et al. |
| 7,713,710 B2 | 5/2010 | Clarke et al. |
| 7,754,206 B2 | 7/2010 | Clarke et al. |
| 7,850,961 B2 | 12/2010 | Clarke et al. |
| 7,919,092 B2 | 4/2011 | Lewicki et al. |
| 8,088,617 B2 | 1/2012 | Gurney et al. |
| 8,206,713 B2 | 6/2012 | Lewicki et al. |
| 8,226,943 B2 | 7/2012 | Gurney et al. |
| 8,404,237 B2 | 3/2013 | Lewicki et al. |
| 8,425,903 B2 | 4/2013 | Gurney et al. |
| 8,425,930 B2 | 4/2013 | Barboza et al. |
| 8,435,513 B2 | 5/2013 | Gurney et al. |
| 8,460,661 B2 | 6/2013 | Gurney et al. |
| 8,784,811 B2 | 7/2014 | Lewicki et al. |
| 8,834,875 B2 | 9/2014 | Van Der Horst |
| 8,921,106 B2 | 12/2014 | Gurney et al. |
| 8,945,547 B2 | 2/2015 | Gurney et al. |
| 8,945,873 B2 | 2/2015 | Gurney et al. |
| 8,945,874 B2 | 2/2015 | Gurney et al. |
| 8,945,878 B2 | 2/2015 | Gurney et al. |
| 8,956,811 B2 | 2/2015 | Li et al. |
| 8,980,260 B2 | 3/2015 | Gurney et al. |
| 9,132,189 B2 | 9/2015 | Van Der Horst et al. |
| 2002/0010320 A1 | 1/2002 | Fett |
| 2002/0086014 A1 | 7/2002 | Korman et al. |
| 2002/0119565 A1 | 8/2002 | Clarke et al. |
| 2002/0122802 A1 | 9/2002 | Wands et al. |
| 2003/0082651 A1 | 5/2003 | Gao et al. |
| 2003/0083465 A1 | 5/2003 | Zimrin et al. |
| 2003/0186290 A1 | 10/2003 | Tournier-Lasserve et al. |
| 2004/0229301 A1 | 11/2004 | Wang |
| 2005/0026831 A1 | 2/2005 | Bodmer et al. |
| 2005/0089518 A1 | 4/2005 | Clarke et al. |
| 2005/0112121 A1 | 5/2005 | Artavanis-Tsakonas et al. |
| 2005/0129686 A1 | 6/2005 | Coignet |
| 2005/0142635 A1 | 6/2005 | Tsuchiya et al. |
| 2005/0187179 A1 | 8/2005 | Miele et al. |
| 2005/0232927 A1 | 10/2005 | Clarke et al. |
| 2006/0030694 A1 | 2/2006 | Kitajewski et al. |
| 2006/0051325 A1 | 3/2006 | Clarke et al. |
| 2006/0073125 A1 | 4/2006 | Clarke et al. |
| 2006/0083682 A1 | 4/2006 | Bergstein |
| 2006/0263774 A1 | 11/2006 | Clark et al. |
| 2007/0036800 A1 | 2/2007 | Bergstein |
| 2007/0036801 A1 | 2/2007 | Bergstein |
| 2007/0036804 A1 | 2/2007 | Bergstein |
| 2007/0041984 A1 | 2/2007 | Bergstein |
| 2007/0196047 A9 | 8/2007 | Levner et al. |
| 2007/0212737 A1 | 9/2007 | Clarke et al. |
| 2007/0265246 A1 | 11/2007 | Clevers et al. |
| 2008/0076670 A1 | 3/2008 | Sivan et al. |
| 2008/0112940 A1 | 5/2008 | Liaw |
| 2008/0118520 A1 | 5/2008 | Li et al. |
| 2008/0131908 A1 | 6/2008 | Li et al. |
| 2008/0132423 A1 | 6/2008 | Kondo |
| 2008/0178305 A1 | 7/2008 | Clarke et al. |
| 2008/0187532 A1 | 8/2008 | Gurney et al. |
| 2008/0188405 A1 | 8/2008 | Di Fiore et al. |
| 2008/0194022 A1 | 8/2008 | Clarke et al. |
| 2008/0226621 A1 | 9/2008 | Fung et al. |
| 2008/0260734 A1 | 10/2008 | Clarke et al. |
| 2009/0004205 A1 | 1/2009 | Clarke et al. |
| 2009/0028856 A1 | 1/2009 | Chen et al. |
| 2009/0081238 A1 | 3/2009 | Siebel et al. |
| 2009/0092615 A1 | 4/2009 | Dang et al. |
| 2009/0137470 A1 | 5/2009 | Stylianou |
| 2009/0155250 A1 | 6/2009 | Chen et al. |
| 2009/0208491 A1 | 8/2009 | Gurney et al. |
| 2010/0080808 A1 | 4/2010 | Siebel et al. |
| 2010/0087358 A1 | 4/2010 | Aster et al. |
| 2011/0033481 A1 | 2/2011 | Clarke et al. |
| 2011/0092378 A1 | 4/2011 | Clarke et al. |
| 2011/0166028 A1 | 7/2011 | Bergstrom et al. |
| 2011/0253679 A1 | 10/2011 | Yamazaki et al. |
| 2011/0274683 A1 | 11/2011 | Wong et al. |
| 2012/0082659 A1 | 4/2012 | Land et al. |
| 2012/0276099 A1 | 11/2012 | Poppe |
| 2012/0328608 A1 | 12/2012 | Siebel |
| 2013/0243774 A1 | 9/2013 | Van Der Horst et al. |
| 2013/0266594 A1 | 10/2013 | Geles et al. |
| 2013/0323266 A1 | 12/2013 | Hoey et al. |
| 2014/0065205 A1 | 3/2014 | Anthony et al. |
| 2014/0093497 A1 | 4/2014 | Reimann et al. |
| 2014/0127211 A1* | 5/2014 | Geles ............... A61K 47/48561 424/138.1 |
| 2015/0166963 A1 | 6/2015 | Gurney et al. |
| 2015/0183878 A1 | 7/2015 | Gurney et al. |
| 2015/0197563 A1 | 7/2015 | Gurney et al. |
| 2015/0232570 A1 | 8/2015 | Hoey et al. |
| 2015/0316552 A1 | 11/2015 | Cain et al. |
| 2016/0030561 A1 | 2/2016 | Hoey et al. |
| 2016/0053016 A1 | 2/2016 | Lewicki et al. |

FOREIGN PATENT DOCUMENTS

| | | |
|---|---|---|
| CN | 102056945 A | 5/2011 |
| DE | 4425115 A1 | 1/1996 |
| EP | 0662827 A1 | 7/1995 |
| EP | 0576623 B1 | 10/2002 |
| EP | 0662827 B2 | 1/2009 |
| EP | 2307459 B1 | 1/2015 |
| JP | 2002526109 A | 8/2002 |
| WO | WO-9219734 A1 | 11/1992 |
| WO | WO-9407474 A1 | 4/1994 |
| WO | WO-9737004 A1 | 10/1997 |
| WO | WO-9745143 A1 | 12/1997 |
| WO | WO-9820142 A1 | 5/1998 |
| WO | WO-9850431 A2 | 11/1998 |
| WO | WO-9857621 A1 | 12/1998 |
| WO | WO-0020576 A2 | 4/2000 |
| WO | WO-0052143 A2 | 9/2000 |
| WO | WO-0200576 A1 | 1/2002 |
| WO | WO-0212447 A2 | 2/2002 |
| WO | WO-0218544 A2 | 3/2002 |
| WO | WO-02059318 A1 | 8/2002 |
| WO | WO-03042246 A2 | 5/2003 |
| WO | WO-03050502 A2 | 6/2003 |
| WO | WO-03062273 A2 | 7/2003 |
| WO | WO-04001004 A2 | 12/2003 |
| WO | WO-2004052389 A2 | 6/2004 |
| WO | WO-2004091383 A2 | 10/2004 |
| WO | WO-2004094475 A2 | 11/2004 |
| WO | WO-2005026334 A2 | 3/2005 |
| WO | WO-2005054434 A2 | 6/2005 |
| WO | WO-2005074633 A2 | 8/2005 |
| WO | WO-2006015375 A2 | 2/2006 |
| WO | WO-2006053063 A2 | 5/2006 |
| WO | WO-2006110581 A2 | 10/2006 |
| WO | WO-2007061988 A2 | 5/2007 |
| WO | WO-2007145840 A2 | 12/2007 |
| WO | WO-2008051797 A2 | 5/2008 |
| WO | WO-2008057114 A1 | 5/2008 |
| WO | WO-2008057144 A2 | 5/2008 |
| WO | WO-2008076960 A2 | 6/2008 |
| WO | WO-2008051797 A3 | 7/2008 |
| WO | WO-2008091641 A2 | 7/2008 |
| WO | WO-2008108910 A2 | 9/2008 |
| WO | WO-2008109075 A2 | 9/2008 |
| WO | WO-2008136848 A2 | 11/2008 |
| WO | WO-2008150525 A1 | 12/2008 |
| WO | WO-2009025867 A2 | 2/2009 |

(56) References Cited

FOREIGN PATENT DOCUMENTS

| WO | WO-2009035522 A1 | 3/2009 |
|---|---|---|
| WO | WO-2009044173 A2 | 4/2009 |
| WO | WO-2009124931 A2 | 10/2009 |
| WO | WO-2010005566 A2 | 1/2010 |
| WO | WO-2010005567 A2 | 1/2010 |
| WO | WO-2010039832 A1 | 4/2010 |
| WO | WO-2011088215 A2 | 7/2011 |
| WO | WO-2012003472 A1 | 1/2012 |
| WO | WO-2013074596 A1 | 5/2013 |
| WO | WO-2013173542 A1 | 11/2013 |
| WO | WO-2014047426 A1 | 3/2014 |
| WO | WO-2014151606 A2 | 9/2014 |
| WO | WO-2015134627 A1 | 9/2015 |
| WO | WO-2015153997 A2 | 10/2015 |

OTHER PUBLICATIONS

Ding, L-C., et al., "Notch-4 Contributes to the Metastasis of Salivary Adenoid Cystic Carcinoma," Oncology Reports 24(2):363-368, D.A. Spandidos, Greece (2010).
Extended European Search Report for EP Application No. 12850629.2, European Patent Office, Netherlands, mailed on May 22, 2015, 11 pages.
Extended European Search Report for EP Application No. 13790284.7, European Patent Office, Munich, Germany, dated Nov. 18, 2015, 10 pages.
Extended European Search Report for EP Application No. 14195878.5, European Patent Office, Germany, mailed on Apr. 10, 2015, 8 pages.
Extended European Search Report for EP Application No. 14199035.8, European Patent Office, Germany, mailed on Jun. 18, 2015, 12 pages.
Extended European Search Report of European Appl. No. 13839746.8, European Patent Office, Munich, Germany, dated Mar. 21, 2016, 8 pages.
First Declaration of Kenneth Geles, Ph.D., for European Patent No. 2152748 B2, Apr. 19, 2016, 3 pages.
Gianfelici, V, "Activation of the NOTCH1 Pathway in Chronic Lymphocytic Leukemia," Haematologica 97(3):328-330, Ferrata Storti Foundation, Italy (2012).
International Preliminary Report on Patentability for Application No. PCT/US2013/060878, International Bureau of WIPO, Switzerland, mailed on Apr. 2, 2015, 11 pages.
International Search Report and Written Opinion for International Application No. PCT/US2015/018756, United States Patent and Trademark Office, United States, mailed on Jul. 2, 2015, 16 pages.
International Search Report and Written Opinion for Application No. PCT/US2015/024291, International Bureau of WIPO, Switzerland, mailed on Sep. 23, 2015, 15 pages.
International Preliminary Report on Patentability for Application No. PCT/US2014/026094, International Bureau of WIPO, Switzerland, issued on Sep. 15, 2015, 8 pages.
Kamdje, A.N., et al., "Role of Stromal Cell-Mediated Notch Signaling in CLL Resistance to Chemotherapy," Blood Cancer Journal 2(5):e73, Macmillan Publishers Limited, England, 10 pages (2012).
Kamstrup, M.R., et al, "Notch1 as a Potential Therapeutic Target in Cutaneous T-Cell Lymphoma," Blood 116(14):2504-2512, American Society of Hematology, United States (2010).
Kamstrup, M.R., et al., "Notch-1 Expression in Cutaneous T-Cell Lymphomas: a Potential Target for Therapeutic Intervention," APMIS 120(Suppl s134):7, The Authors APMIS, United States, abstract O2-6 (2012).
Kapoun, A.M., et al., "Development and Validation of a Biomarker for Prospective Selection of Notch1 Activation in Patients with Certain Advanced Solid Tumors in a First-in-Human Phase1 Study of the Cancer Stem Cell Targeting Antibody OMP-52M51 (anti-Notch1)," 2015 AACR Annual Meeting, Poster with Abstract 1549. 1 page (2015).

Koch, U. and Radtke, F., "Notch and Cancer: A Double-Edged Sword," Cellular and Molecular Life Sciences 64(21):2746-2762, Springer, Switzerland (2007).
Kridel, R., et al., "Whole transcriptome sequencing reveals recurrent NOTCH1 mutations in mantle cell lymphoma," Blood 119(9):1963-1971, The American Society of Hematology, United States (Mar. 2012).
Lobry, C., et al., "Notch Signaling: Switching an Oncogene to a Tumor Suppressor," Blood 123(16):2451-2459, American Society of Hematology, United States (Apr. 2014).
Lobry, C., et al., "Oncogenic and Tumor Suppressor Functions of Notch in Cancer: it's NOTCH What You Think," Journal of Experimental Medicine 208(10):1931-1935, Rockefeller University Press, United States (2011).
OncoMed Pharmaceuticals Press Release, "FDA Grants Orphan Drug Designations to OncoMed's Tarextumab for the Treatment of Pancreatic and Small Cell Lung Cancer," Jan. 29, 2015, 3 pages.
OncoMed Pharmaceuticals Press Release, "OncoMed Announces Abstracts Accepted for Presentation at the 2015 ASCO Annual Meeting," Apr. 21, 2015, 2 pages.
OncoMed Pharmaceuticals Press Release, "OncoMed Highlights Immuno-Oncology Discoveries During 2015 Research & Development Day," Apr. 29, 2015, 3 pages.
OncoMed Pharmaceuticals Press Release, "OncoMed Pharmaceuticals to Review Key ASCO Data for Demcizumab and Tarextumab During Conference Call on Tuesday, Jun. 2, 2015," May 28, 2015, 2 pages.
OncoMed Pharmaceuticals Press Release, "OncoMed Presents Data from Phase 1b Trial of Demcizumab in Pancreatic Cancer at the 2015 ASCO Annual Meeting," Jun. 1, 2015, 3 pages.
OncoMed Pharmaceuticals Press Release, "OncoMed Presents Data on Clinical and Preclinical Anti-Cancer Stem Cell Programs at American Association for Cancer Research Annual Meeting," Apr. 21, 2015, 3 pages.
OncoMed Pharmaceuticals Press Release, "OncoMed Publishes Data on Tarextumab's Anti-Cancer Stem Cell Activity in Clinical Cancer Research," May 1, 2015, 2 pages.
OncoMed Pharmaceuticals Press Release, "OncoMed to Present Data on Multiple Anti-Cancer Stem Cell Candidates at the American Association of Cancer Research Meeting," Mar. 19, 2015, 2 pages.
Opponent's Response letter to Summons to attend Oral Proceedings and to Patentee's response to the Notice of Opposition, Opposition to European Patent No. 2152748 B2 (Application No. 08768087.2), Genentech Inc. vs. OncoMed Pharmaceuticals, Inc., dated Apr. 20, 2016, 16 pages.
Pietanza, M.C., et al., "Final Results of Phase 1b of Tarextumab (TRXT, OMP-59R5, anti-Notch2/3) in Combination with Etoposide and Platinum (EP) in Patients (pts) with Untreated Extensive-stage Small-Cell Lung Cancer (ED-SCLC)," 2015 ASCO Annual Meeting, Abstract 7508, 2 pages (2015).
Proprietor's Written Submission in response to Summons to attend Oral Proceedings, including Main Request, Auxiliary Requests 1, 2, and 3, Annex I, Authorised Representatives, Opposition to European Patent No. 2152748 B2 (Application No. 08768087.2), Genentech Inc. vs. OncoMed Pharmaceuticals, Inc., dated Apr. 20, 2016, 31 pages.
Qi, R., et al., "Notch1 Signaling Inhibits Growth of Human Hepatocellular Carcinoma through Induction of Cell Cycle Arrest and Apoptosis," Cancer Research 63(23):8323-8329, American Association for Cancer Research, United States (2003).
Rosati, E., et al., "Constitutively Activated Notch Signaling is Involved in Survival and Apoptosis Resistance of B-CLL Cells," Blood 113(4):856-865, American Society of Hematology, United States (2009).
Shah, J., et al., "Tarextumab (Anti-NOTCH2/3) Reverses NOTCH2 and NOTCH3-Dependent Tumorigenicity and Metastases in Small Cell Lung Cancer," 2015 AACR Annual Meeting, Poster with Abstract 2323, 1 page (2015).
Shih, I-M., and Wang, T-L., "Notch Signaling, γ-Secretase Inhibitors, and Cancer Therapy," Cancer Research 67(5):1879-1882, American Association for Cancer Research, United States (2007).

(56) References Cited

OTHER PUBLICATIONS

Summons to attend oral proceedings pursuant to Rule 115(1) EPC for European Patent Application No. 08768087.2-1403/2152748, European Patent Office, Germany, mailed on Apr. 2, 2015.

Thermo Scientific, "Notch1 Antibody (A6), Product Data Sheet," thermoscientific.com/pierce, accessed at http://www.pierce-antibodies.com/products/printProductDetail/printProductDetails.cfm?js=1&format=extended&catnbr=MA1-91405, accessed on Oct. 21, 2015, 6 pages.

Van Der Fits, L., et al., "NOTCH1 Signaling as a Therapeutic Target in Sézary Syndrome," Journal of Investigative Dermatology 132(12):2810-2817, The Society for Investigative Dermatology, United States (2012).

Wang, J., et al., "Regulation of Differentiation and Proliferation of Marrow Hematogenesis Stem Cells by Notch1 Signaling System from Patients with Aplastic Anemia and Chronic Myelogenous Leukemia," Blood 108(11):4215, American Society of Hematology, United States, 2 pages (2006).

Yen, W-C., et al., "Targeting Notch Signaling with a Notch2/Notch3 Antagonist (Tarextumab) Inhibits Tumor Growth and Decreases Tumor-Initiating Cell Frequency," Clinical Cancer Research 21(9):2084-2095, American Association for Cancer Research, United States (2015).

Yin, L., et al., "Notch Signaling: Emerging Molecular Targets for Cancer Therapy," Biochemical Pharmacology 80(5):690-701, Elsevier Science, England (2010).

Zweidler-McKay, P.A., et al., "Notch Signaling is a Potent Inducer of Growth Arrest and Apoptosis in a Wide Range of B-Cell Malignancies," Blood 106(12):3898-3906, American Society of Hematology, United States (2005).

"4G1 NotchI monoclonal antibody," Abnova technical datasheet, accessed at www.abnova.com/products/products_details.asp?Catalogid=1-100004851-M10, accessed on Nov. 9, 2012, 8 pages.

Ahmad, I., et al., "Involvement of Notch-1 in Mammalian Retinal Neurogenesis: Association of Notch-1 Activity with Both Immature and Terminally Differentiated C\ells," Mechanisms of Development 53(1):73-85, Elsevier Scientific Publishers, Ireland (1995).

Al-Hajj, M., et al., "Prospective Identification of Tumorigenic Breast Cancer Cells," Proceedings of the National Academy of Sciences 100(7):3983-3988, The National Academy of Sciences, United States (2003).

Al-Lazikani, B., et al., "Standard Conformations for the Canonical Structures of Immunoglobulins," Journal of Molecular Biology 273(4):927-948, Academic Press Limited, United States (1997).

Allenspach, E.J., et al., "Notch Signaling in Cancer," Cancer Biology Therapy 1(5):466-476, Informa UK Limited, United Kingdom (2002).

Arias, A.M., et al., "CSL-independent notch signalling: a checkpoint in cell fate decisions during development?," Current Opinion in Genetics & Development 12(5):524-533, Elsevier Science Ltd, United Kingdom (2002).

Armstrong, F., et al., "NOTCH is a Key Regulator of Human T-Cell Acute Leukemia Initiating Cell Activity," Blood 113(8):1730-1740, The American Society of Hematology, United States (2009).

Artavanis-Tsakonas, S., et al., "Notch Signaling: Cell Fate Control and Signal Integration in Development," Science 284(5415):770-776, American Association for the Advancement of Science, United States (1999).

Aste-Amezaga, M., et al., "Characterization of Notch1 Antibodies That Inhibit Signaling of Both Normal and Mutated Notch1 Receptors," PLoS One 5(2):1-13, Public Library of Science, United States (2010).

Axelson, H., "Notch Signaling and Cancer: Emerging Complexity," Seminars in Cancer Biology 14(5):317-319, Academic Press, England (2004).

Bellavia, D., et al. "Constitutive Activation of NF-kappaB and T-cell Leukemia/lymphoma in Notch3 Transgenic Mice," The EMBO Journal 19(13):3337-3348, European Molecular Biology Organization, Germany (2000).

Bellavia, D., et al., "Notch3: from Subtle Structural Differences to Functional Diversity," Oncogene 27(38):5092-5098, Nature Publishing Group, England (2008).

Bendell, J., et al., "Final Results of a Phase 1b of OMP-59R5 (Anti-Notch2/3/Stem Cell Antibody) in Combination with Nab-Paclitaxel and Gemcitabine (Nab-P + Gem) in Patients (Pts) with Untreated Metastatic Pancreatic Cancer (Mpc): Alpine Study," ESMO 2014, Published by Oxford University Press, Abstract 688P, 1 page (2014).

Bendell, J., et al., "Final Results of a Phase 1b of OMP-59R5 (Anti-Notch2/3/Stem Cell Antibody) in Combination with Nab-Paclitaxel and Gemcitabine (Nab-P + Gem) in Patients (pts) with Untreated Metastatic Pancreatic Cancer (MPC): Alpine Study," ESMO 2014, Sep. 29, 2014, Poster Display session, 3 Pages (2014).

Bendig, M., "Humanization of Rodent Monoclonal Antibodies by CDR Grafting," METHODS: A Companion to Methods in Enzymology 8:83-93, Academic Press, England (1995).

Bheeshmachar, G., et al., "Evidence for a Role for Notch Signaling in the Cytokine-Dependent Survival of Activated T Cells," Journal of immunology 177(8):5041-5050, American Association of Immunologists, United States (2006).

Boldt, H.B., et al., "The Lin12-Notch Repeats of Pregnancy-Associated Plasma Protein-A Bind Calcium and Determine Its Proteolytic Specificity," The Journal of Biological Chemistry 279(37):38525-38531, American Society for Biochemistry and Molecular Biology, United States (2004).

Bolos, V., et al., "Notch Signaling in Development and Cancer," Endocrine Reviews 28(3):339-363, The Endocrine Society, United States (2007).

Brennan, K. and Brown, A.M., "Is there a Role for Notch Signalling in Human Breast Cancer?," Breast Cancer Research 5(2):69-75, BioMed Central Ltd., United Kingdom (2003).

Brennan, K., et al., "Repression by Notch is Required before Wingless Signalling During Muscle Progenitor cell Development in *Drosophila*," Current Biology 9(13):707-710, Current Biology Publications, United Kingdom (1999).

Brennan, M., et al., "Preparation of Bispecific Antibodies by Chemical Recombination of Monoclonal Immunoglobulin G.sub.1 Fragments," Science 229(4708):81-83, American Association for the Advancement of Science, United States (1985).

Brorson, K., et al., "Mutational Analysis of Avidity and fine Specificity of Anti-levan Antibodies," The Journal of Immunology 163(12):6694-6701, American Association of Immunologists, United States (1999).

Brummell, D.A., et al., "Probing the Combining Site of an Anti-Carbohydrate Antibody by Saturation-Mutagenesis: Role of the Heavy-chain CDR3 Residues," 32(4):1180-1187, American Chemical Society, United States (1993).

Burks, E.A., et al., "In Vitro Scanning Saturation Mutagenesis of an Antibody Binding Pocket," Proceedings of the National Academy of Sciences 94(2):412-417, National Academy of Sciences, United States (1997).

Callahan, R. and Raafat, A., "Notch Signaling in Mammary Gland Tumorigenesi," Journal of Mammary Gland Biology and Neoplasia 6(1):23-36, Kluwer Academic/Plenum Publishers, United States (2001).

Campbell, A.M., "Characterisation of monoclonal antibodies," in Laboratory Techniques in Biochemistry and Molecular Biology, Monoclonal Antibody Technology: The Production and Characterization of Rodent and Human Hybridomas, vol. 13, pp. 186-215, Elsevier, the Netherlands (1984).

Campbell, A.M., "Monoclonal Antibody Technology," The Production and Characterization of Rodent and Human Hybridomas, 13:29 pages, Elsevier Science Publishers B.V, The Netherlands (1984).

Cancilla, B., et al., "Anti-Notch1 Antibody (OMP-52M51) Impedes Tumor Growth and Cancer Stem Cell Frequency (CSC) in a Chemorefractory Breast Cancer Xenograft Model with an Activating Notch1 Mutation and Screening for Activated Notch1 Across Multiple Solid Tumor Types," Proceedings of the 104th Annual Meeting of the American Association for Cancer Research, Apr. 6-10, 2013, Abstract 3728, 2 pages (2013).

Cancilla, B., et al., "NOTCH3 Expression is Predictive of Efficacy in Pancreas Tumor Models Treated with OMP-59R5, a Monoclonal

(56) References Cited

OTHER PUBLICATIONS

Antibody Targeting the NOTCH2 and NOTCH3 Receptors," Proceedings of the 105th Annual Meeting of the American Association for Cancer Research, Apr. 5-9, 2014, Abstract 910, 1 page (2014).
Casset, F., et al., "A Peptide Mimetic of an Anti-CD4 Monoclonal Antibody by Rational Design" Biochemical and Biophysical Research Communications 307(1):198-205, Academic Press, United States (2003).
Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (1999).
Clackson, T., et al., "Making Antibody Fragments Using Phage Display Libraries," Nature 352(6336):624-628, Nature Publishing Group, England (1991).
Cole, S., et al., "The EBV-Hybridoma Technique and Its Application to Human Lung Cancer," Monoclonal Antibodies and Cancer Therapy, 77-96, Proceedings of the Roche-UCLA Symposium, United States (1985).
Colman, P.M., et al., "Effects of Amino Acid Sequence Changes on Antibody-Antigen Interactions," Research in Immunology 145(1):33-36, Elsevier, France (1994).
Cook, N., et al., "Gamma Secretase Inhibition Promotes Hypoxic Necrosis in Mouse Pancreatic Ductal Adenocarcinoma," The Journal of experimental medicine 209(3):437-444, Rockefeller University Press, United States (2012).
Co-pending U.S. Appl. No. 14/358,331, inventors Cain, J.A., et al., filed May 15, 2014 (Not Published).
Co-pending U.S. Appl. No. 14/429,497, inventors Hoey, T.C. et al., filed Mar. 19, 2015 (Not Published).
Co-pending U.S. Appl. No. 14/550,703, inventors Gurney, A.L., et al., filed Nov. 21, 2014 (Not Published).
Co-pending U.S. Appl. No. 14/577,484, inventors Gurney, A.L., et al., filed Dec. 19, 2014 (Not Published).
Co-pending U.S. Appl. No. 14/600,641, inventors Gurney, A.L., et al., filed Jan. 20, 2015 (Not Published).
Cox, C.V., et al., "Characterization of Acute Lymphoblastic Leukemia Progenitor Cells," Blood 104(9):2919-2925, The American Society of Hematology, United States (2004).
Cui, H., et al., "Notch3 Functions as a Tumor Suppressor by Controlling Cellular Senescence," Cancer Research 73(11):3451-3459, American Association for Cancer Research, United States (2013).
Curry, C.L., et al., "Gamma Secretase Inhibitor Blocks Notch Activation and Induces Apoptosis in Kaposi's Sarcoma Tumor Cells," Oncogene 24(42):6333-6344, Nature Publishing Group, United States (2005).
Davis, S.L., et al., "A First-in-Human Phase I Study of the Novel Cancer Stem Cell (CSC) Targeting Antibody OMP-52M51 (Anti-Notch1) Administered Intravenously to Patients with Certain Advanced Solid Tumors," Proceedings of the AACR-NCI-EORTC International Conference: Molecular Targets and Cancer Therapeutics, Oct. 19-23, 2013, Abstract B48, 2 Pages (2013).
De Pascalis, R., et al., "Grafting of 'Abbreviated' Complementarity-Determining Regions Containing Specificity-Determining Residues Essential for Ligand Contact to Engineer a Less Immunogenic Humanized Monoclonal Antibody," Journal of Immunology 169(6):3076-3084, The American Association of Immunologists, United States (2002).
Declaration of Dr. Stephen Blacklow, M.D., Ph.D., for European Patent No. 2152748 B2, 34 pages, Dec. 18, 2014.
Deftos, M.L., et al., "Correlating Notch Signaling with Thymocyte Maturation," Immunity 9(6):777-786, Cell Press, United States (1998).
Del Amo, F.F., et al., "Cloning, Analysis, and Chromosomal Localization of Notch-1, a Mouse Homolog of Drosophila Notch," Genomics 15(2):259-264, Elsevier Science, United Science (1993).
Dikic, I., et al., "Notch: Implications of Endogenous Inhibitors for Therapy," Bioessays 32(6):481-487, John Wiley & Sons, United States (2010).

Domenga, V., et al., "Notch3 is Required for Marterial Identity and Maturation of Vascular Smooth Muscle Cells," Genes & Development 18(22):2730-2735, Cold Spring Harbor Laboratory Press, United States (2004).
Dontu, G., et al., "Role of Notch Signaling in Cell-Fate Determination of Human Mammary Stem/progenitor Cells," Breast Cancer Research 6(6):R605-R615, BioMed Central, England (2004).
Duan, Z., et al., "A Novel Notch Protein, N2N, Targeted by Neutrophil Elastase and Implicated in Hereditary Neutropenia," Molecular and Cellular Biology 24(1):58-70, American Society for Microbiology, United States (2004).
Duncan, A.W., et al., "Integration of Notch and Wnt Signaling in Hematopoietic Stem Cell Maintenance," Nature Immunology 6(3):314-322, Nature Publishing Group, United States (2005).
Ellisen, L.W., et al., "TAN-1, the Human Homolog of the Drosophila notch Gene, is broken by Chromosomal Translocations in T Lymphoblastic Neoplasms," Cell 66(4):649-661, Elsevier Science, United States (1991).
English language Abstract of World Patent Publication No. WO0200576A1, European Patent Office, espacenet database—Worldwide, (2002).
Extended European Search Report of European Appl. No. 08724737.5, European Patent Office, Munich, Germany, dated Sep. 24, 2010.
Fang, P., et al., "Development and Validation of a Notch Custom NGS Assay for Identifying Notch1 Mutations in Chronic Lymphocytic Leukemia and Other Lymphoid Malignancies," 19th European Hematology Association Congress, held Jun. 12-Jun. 15, 2014, Abstract P861, 2 pages, (2014).
Fischer, M., et al., "OMP-59R5 (Anti-Notch2/3) Inhibits Tumor Growth and Reduces Cancer Stem Cell Frequency in Patient Derived SCLC Xenografts," Proceedings of the 105th Annual Meeting of the American Association for Cancer Research, Apr. 5-9, 2014, Abstract 3048, 2 pages (2014).
Fischer, M.M., et al., "Targeting Cancer Stem Cells by a Notch2/Notch3 Cross-Reactive Antibody Inhibits Tumor Growth and Delays Tumor Recurrence in Pancreatic Cancer," Proceedings of the 103rd Annual Meeting of the American Association for Cancer Research, Mar. 31-Apr. 4, 2012, Abstract 1014, 2 pages (2012).
Fleming, R.J., et al., "The Notch receptor and its ligands," Trends in Cell Biology 7(11):437-441, Elsevier Science Ltd., The Netherlands (1997).
Fre, S., et al., "Notch Signals Control the Fate of Immature Progenitor Cells in the Intestine," Nature 435(7044):964-968, Nature Publishing Group, United States (2005).
Freeman, J.W., et al., "Masking of Nontumorous Antigens for Development of Human Tumor Nucleolar Antibodies with Improved Specificity," Cancer research 45(11 Pt 2):5637-5642, American Association for Cancer Research, United States (1985).
Gale, N. W., et al., "Haploinsufficiency of Delta-like 4 Ligand Results in Embryonic Lethality due to Major Defects in arterial and Vascular Development," Proceedings of the National Academy of Sciences 101(45):15949-15954, National Academy of Sciences, United States (2004).
Gallahan, D., and Callahan, R., "The Mouse Mammary Tumor Associated Gene INT3 is a Unique Member of the NOTCH Gene Family (NOTCH4)," Oncogene 14:1838-1890, Stockton Press, United States (1997).
Gallahan, D., et al., "Expression of a Truncated Int3 Gene in Developing Secretory Mammary Epithelium Specifically Retards Lobular Differentiation Resulting in Tumorigenesis," Cancer Research 56(8):1775-1785, American Association for Cancer Research, United States (1996).
Gordon, W.R., et al., "Structural Basis for Autoinhibition of Notch," Nature Structural & Molecular Biology 14(4):295-300, Nature Publishing Group, United States (2007).
Gordon, W.R., et al., "Structure of the Notch1-Negative Regulatory Region: Implications for Normal Activation and Pathogenic Signaling in T-All," Blood 113(18):4381-4390, American Society of Hematology, United States (2009).

(56) References Cited

OTHER PUBLICATIONS

Grabher, C., et al., "Notch 1 Activation in the Molecular Pathogenesis of T-Cell Acute Lymphoblastic Leukaemia," Nature Reviews Cancer 6(5):347-359, Nature Publishing Group, United States (2006).
Greenspan, N.S. and Di Cera. E., "Defining Epitopes: It's not as Easy as it Seems," Nature Biotechnology 17(10):936-937, Nature Publishing Group, United States (1999).
Gridley, T., "Notch Signaling and Inherited Disease Syndromes," Human Molecular Genetics 12(SpecNo. 1):R9-R13, Oxford University Press, United Kingdom (2003).
Gridley, T., "Notch Signaling During Vascular Development," Proceedings of the National Academy of Sciences 98(10):5377-5378, National Academy of Sciences, United States (2001).
Gridley, T., "Notch Signaling in Vertebrate Development and Disease," Molecular and Cellular Neuroscience 9(2):103-108, Academic Press, United States (1997).
Gridley, T., "Vessel guidance," Nature, 445(7129):722-723 (2007) Nature Publishing Group, United States (2007).
Gruber, M., et al., "Efficient Tumor Cell Lysis Mediated by a Bispecific Single Chain Antibody Expressed in *Escherichia coli*," The Journal of Immunology 152(11):5368-5374, The American Association of Immunologists, Inc., United States (1994).
Hadland, B.K., et al., "A Requirement for Notch1 Distinguishes 2 Phases of Definitive Hematopoiesis During Development," Blood 104(10):3097-3105, The American Society of Hematology, United States (2004).
Hainaud, P., et al., "The role of the vascular endothelial growth factor-Delta-like 4 ligand/Notch4-ephrin B2 cascade in tumor vessel remodeling and endothelial cell functions," Cancer Research 66(17):8501-8510, American Association for Cancer Research, United States (2006).
Hallahan, A.R., et al., "The SmoA1 Mouse Model Reveals that Notch Signaling is Critical for the Growth and Survival of Sonic Hedgehog-Induced Medulloblastomas," Cancer Research 64(21):7794-7800, American Association for Cancer Research, United States (2004).
Hambleton, S., et al., "Structural and Functional Properties of the Human Notch-1 Ligand Binding Region," Structure 12(12):2173-2183, Cell Press, United States (2004).
Harper, J.A., et al., "Notch Signaling in Development and Disease," Clinical Genetics 64(6):461-472, Blackwell Publishing, United States (2003).
Hitoshi, S., et al., "Notch Pathway Molecules are Essential for the Maintenance, but not the Generation, of Mammalian Neural Stem Cells," Genes & Development 16(7):846-858, Cold Spring Harbor Laboratory Press, United States (2002).
Holm, P., et al., "Functional Mapping and Single Chain Construction of the Anti-Cytokeratin 8 Monoclonal Antibody TS1," Molecular Immunology 44(6):1075-1084, Pergamon Press, England (2007).
Hoogenboom, H.R. and Winter, G., "By-Passing Immunisation. Human Antibodies from Synthetic Repertoires of Germline VH Gene Segments Rearranged in Vitro," Journal of Molecular Biology 227(2):381-388, Elsevier Science, United States (1992).
Hopfer, et al., "The Notch Pathway in Ovarian Carcinomas and Adenomas," British Journal of Cancer 93(6):709-718, Nature Publishing Group on behalf of Cancer Research UK, England (2005).
Hosse, R.J., et al., "A New Generation of Protein Display Scaffolds for Molecular Recognition," Protein Science 15(1):14-27, Cold Spring Harbor Laboratory Press, United States (2006).
Houde, C., et al., "Overexpression of the Notch Ligand Jag2 in Malignant Plasma Cells from Multiple Myeloma Patients and Cell Lines," Blood 104(12):3697-3704, American Society of Hematology, United States (2004).
Huang, E.Y., et al., "Surface Expression of Notch1 on Thymocytes: Correlation With the Double-Negative to Double-Positive Transition," The Journal of Immunology 171(5):2296-2304, The American Association of Immunologists, Inc., United States (2003).

Huse, W.D., et al., "Generation of a Large Combinatorial Library of the Immunoglobulin Repertoire in Phage Lambda," Science 246(4935):1275-1281, American Association for the Advancement of Science, United States (1989).
Imatani, A. and Callahan, R., "Identification of a Novel NOTCH-4/INT-3 RNA Species Encoding an Activated Gene Product in Certain Human Tumor Cell Lines," Oncogene 19(2):223-231, Nature Publishing Group, United States (2000).
International Preliminary Report on Patentability for International Application No. PCT/US2009/003994, mailed on Jan. 11, 2011, 8 pages.
International Search Report and Written Opinion for Application No. PCT/US2013/060878, US Patent Office, Virginia, mailed on Dec. 17, 2013, 14 pages.
International Search Report and Written Opinion for Application No. PCT/US2014/026094, mailed on Oct. 3, 2014, 13 pages.
International Search Report and written opinion for International Application No. PCT/US09/03994, mailed on Jul. 23, 2010, 13 pages.
International Search Report and written opinion for International Application No. PCT/US09/03995, mailed on Mar. 2, 2010, 10 pages.
International Search Report and Written Opinion for International Application No. PCT/US2013/041279, US Patent Office, mailed on Oct. 24, 2013.
International Search Report for International Application No. PCT/US08/00884 United States Patent and Trademark Office, U.S.A., mailed on Oct. 1, 2008.
International Search Report for International Application No. PCT/US11/21135, International Searching Authority, mailed on Jul. 20, 2011.
International Search Report for International Application No. PCT/US2008/001948, United States Patent and Trademark Office, mailed on Oct. 15, 2008.
International Search Report for International Application No. PCT/US2013/041279, US Patent Office, mailed on Oct. 24, 2013.
Iso, T., et al., "Notch Signaling in Vascular Development," Arteriosclerosis, Thrombosis, and Vascular Biology 23(4):543-553, American Heart Association, Inc., United States (2003).
Jang, M.S., et al., "Notch Signaling as a Target in Multimodality Cancer Therapy," Current Opinion in Molecular Therapeutics 2(1):55-65, Thomson Reuters (Scientific) Ltd., England (2000).
Jang, Y.J., et al., "The Structural Basis for DNA Binding by an Anti-DNA Autoantibody," Molecular Immunology 35(18):1207-1217, Pergamon Press, England (1998).
Jarriault, S., et al., "Signalling Downstream of Activated Mammalian Notch," Nature 377(6547):355-358, Nature Publishing Group, United States (1995).
Jehn, B.M., et al., "Cutting Edge: Protective Effects of Notch-1 on TCR-Induced Apoptosis," The Journal of Immunology 162(2):635-638, The American Association of immunologists, Inc., United States (1999).
Jemal, A., et al., "Cancer statistics, 2010," A Cancer Journal for Clinicians 60(5):277-300, American Cancer Society, Inc., United States (2010).
Jhappan, C., et al., "Expression of an Activated Notch-Related int-3 Transgene Interferes with Cell Differentiation and Induces Neoplastic Transformation in Mammary and Salivary Glands," Genes & Development 6(3):345-355, Cold Spring Harbor Laboratory Press, United States (1992).
Joutel, A. and Tournier-Lasserve, E., "Notch Signalling Pathway and Human Diseases," Seminars in Cell & Developmental Biology 9(6):619-625, Academic Press, United States (1998).
Joutel, A., et al., "Notch3 Mutations in CADASIL, a Hereditary Adult-Onset Condition Causing Stroke and Dementia," Nature 383(6602):707-710, Macmillan Magazines Ltd., United States (1996).
Jundt, F., et al., "Activated Notch1 Signaling Promotes Tumor Cell Proliferation and Survival in Hodgkin and Anaplastic Large Cell Lymphoma," Blood 99(9):3398-3403, The American Society of Hematology, United States (2002).

(56) References Cited

OTHER PUBLICATIONS

Jundt, F., et al., "Jagged1-Induced Notch Signaling Drives Proliferation of Multiple Myeloma Cells," Blood 103(9):3511-3515, The American Society of Hematology, United States (2004).
Jurynczyk, M., et al., "Notch3 Inhibition in Myelin-Reactive T Cells Down-Regulates Protein Kinase C Theta and Attenuates Experimental Autoimmune Encephalomyelitis," The Journal of Immunology 180(4):2634-2640, The American Association of Immunologists, Inc., United States (2008).
Kapoun, A.M., et al., "Biomarker Analysis in Phase 1b Study of Anti-Cancer Stem Cell Antibody Tarextumab(TRXT) in Combination with Nab-Paclitaxeland Gemcitabine(Nab-P+Gem) Demonstrates Pharmacodynamic(PD) Modulation of the Notch Pathway in Patients (pts) with Untreated Metastatic Pancreatic Cancer (mPC)," 1 page (2014).
Karanu, F.N., et al., "The Notch Ligand Jagged-1 Represents a Novel Growth Factor of Human Hematopoietic Stem Cells," The Journal of Experimental Medicine 192(9):1365-1372, The Rockefeller University Press, United States (2000).
Kellogg, D.E., et al., "Taqstart Antibody: 'Hot Start' PCR Facilitated by a Neutralizing Monoclonal Antibody Directed Against Taq DNA Polymerase," BioTechniques 16(6):1134-1137, Informa Healthcare USA, Inc, England (1994).
Kidd, S., et al., "Sequence of the Notch Locus of *Drosophila melanogaster*: Relationship of the Encoded Protein to Mammalian Clotting and Growth Factors," Molecular and Cellular Biology 6(9):3094-3108, American Society for Microbiology, United States (1986).
Kidd, S., et al., "Structure and Distribution of the Notch Protein in Developing *Drosophila*," Genes & Development 3 (8):1113-1129, Cold Spring Harbor Laboratory Press, United States (1989).
Kobayashi, H., et al., "Tryptophan H33 Plays an Important Role in Pyrimidine (6-4) Pyrimidone Photoproduct Binding by a High-Affinity Antibody," Protein Engineering Design and Selection 12(10):879-884, Oxford University Press, United States (1999).
Kohler, G,and Milstein, C., "Continuous Cultures of Fused Cells Secreting Antibody of Predefined Specificity," Nature 256(5517):495-497, Nature Publishing Group, England (1975).
Kopper, L., and Hajdu, M., "Tumor Stem Cells," Pathology and Oncology Research 10(2):69-73, Aranyl Lajos Foundation, Hungary (2004).
Kostelny, S.A., et al., "Formation of a Bispecific Antibody by the Use of Leucine Zippers," The Journal of Immunology 148(5):1547-1553, American Association of Immunologists, United States (1992).
Krebs, L.T., et al., "Notch Signaling is Essential for Vascular Morphogenesis in Mice," Genes & Development 14(11):1343-1352, Cold Spring Harbor Laboratory Press, United States (2000).
Kuukasjarvi, T., et al., "Genetic Heterogeneity and Clonal Evolution Underlying Development of Asynchronous Metastasis in Human Breast Cancer," Cancer Research 57:1597-1604, The American Association for Cancer Research, United States (1997).
Lapidot, T., et al., "A Cell Initiating Human Acute Myeloid Leukaemia After Transplantation Into SCID Mice," Nature 367(6464):645-648, Nature Publishing Group, United States (1994).
Lasky, J.L. and Wu, H.,, "Notch Signaling, Brain Development, and Human Disease," Pediatric Research 57(5 Pt 2):104R-109R, Nature Publishing Group, United States (2005).
Lawrence, N., et al., "Notch signaling targets the Wingless responsiveness of a Ubx visceral mesoderm enhancer in *Drosophila*," Current Biology 11(6):375-385, Cell Press, United States (2001).
Lee, J.S., et al. "Intracisternal Type A Particle-Mediated Activation of the Notch4/int3 Gene in a Mouse Mammary Tumor: Generation of Truncated Notch4/int3 mRNAs by Retroviral Splicing Events," Journal of Virology 73(6): 5166-5171, The American Society for Microbiology, United States (1999).
Lee, S.H., et al., "Mutational Analysis of NOTCH1, 2, 3 and 4 Genes in Common Solid Cancers and Acute Leukemias," Acta Pathologica, Microbiologica et Immunologica Scandinavica 115(12):1357-1363, Munksgaard, Denmark (2007).
Leethanakul, C., et al., "Distinct Pattern of Expression of Differentiation and Growth-Related Genes in Squamous Cell Carcinomas of the Head and Neck Revealed by the Use of Laser Capture Microdissection and Cdna Arrays," Oncogene 19(28):3220-3224, Nature Publishing Group, United States (2000).
Leong, K.G. and Karsan, A., "Recent Insights into the Role of Notch Signaling in Tumorigenesis," Blood 107(6):2223-2233, The American Society of Hematology, United States (2006).
Leong, K.G., et al., "Activated Notch4 Inhibits Angiogenesis: Role of beta 1-Integrin Activation," Molecular and Cellular Biology 22(8):2830-2841, American Society for Microbiology, United States (2002).
Li, K., et al., "Modulation of Notch Signaling by Antibodies Specific for the Extracellular Negative Regulatory Region of NOTCH3," The Journal of Biological Chemistry 283(12):8046-8054, The American Society for Biochemistry and Molecular Biology, Inc., United States (2008).
Li, L., et al., "Cloning, Characterization, and the Complete 56.8-Kilobase DNA Sequence of the Human NOTCH4 gene," Genomics 51(1):45-58, Elsevier Science, United States (1998).
Li, L., et al., "The Human Homolog of rat Jagged1 Expressed by Marrow Stroma Inhibits Differentiation of 32D Cells through Interaction with Notch1," Immunity 8(1):43-55, Cell Press, United States (1998).
Lin, L., et al., "Targeting Specific Regions of the Notch3 Ligand-Binding Domain Induces Apoptosis and Inhibits Tumor Growth in Lung Cancer," Cancer Research 70(2):632-638, American Association for Cancer Research, United States (2010).
Lindsell, C.E., et al., "Jagged: a Mammalian Ligand that Activates Notch1," Cell 80(6):909-917, Cell Press, United States (1995).
Liu, H., et al., "Notch3 is Critical for Proper Angiogenesis and Mural Cell Investment," Cancer Research 107(7):860-870, Lippincott Williams & Wilkins, United States (2010).
Liu, Z., et al., "Notch1 Loss of Heterozygosity causes Vascular Tumors and Lethal Hemorrhage in Mice," Journal of Clinical Investigation 121(2):800-808, American Society for Clinical Investigation, United States (2011).
Lobo, P.I. and Spencer, C.E., "Use of Anti-HLA Antibodies to Mask Major Histocompatibility Complex Gene Products on Tumor Cells Can Enhance Susceptibility of these Cells to Lysis by Natural Killer Cells," The Journal of Clinical Investigation 83(1):278-287, American Society for Clinical Investigation, United States (1989).
Lohr, J.G., et al., "Discovery and prioritization of somatic mutations in diffuse large B-cell lymphoma (DLBCL) by whole-exome sequencing," Proceedings of the National Academy of Sciences 109(10):3879-3884, National Academy of Sciences, United States (Mar. 2012).
Luo, B., et al., "Isolation and Functional Analysis of a cDNA for Human Jagged2, a Gene Encoding a Ligand for the Notch1 Receptor," Molecular and Cellular Biology 17(10):6057-6067, American Society for Microbiology, United States (1997).
MacCallum, R.M., et al., "Antibody Antigen Interactions: Contact Analysis and Binding Site Topography," Journal of Molecular Biology 262(5):732-745, Elsevier, England (1996).
Maillard, I., et al., "Mastermind Critically Regulates Notch-Mediated Lymphoid Cell Fate Decisions," Blood 104(6):1696-1702, The American Society of Hematology, Unites States (2004).
Malecki, M.J., et al., "Leukemia-Associated Mutations within the Notch1 Heterodimerization Domain Fall into at Least Two Distinct Mechanistic Classes," Molecular arid Cellular Biology 26(12):4642-4651, American Society for Microbiology. United States (2006).
Mao., et al. Genbank Accession No. AY170508; Oct. 1, 2003.
Marks, J.D., et al., "By-Passing Immunization: Building High Affinity Human Antibodies by Chain Shuffling," Biotechnology 10(7):779-783, Nature Publishing Company, United States (1992).
Marks, J.D., et al., "By-passing immunization Human Antibodies from V-Gene Libraries Displayed on Phage," Journal of Molecular Biology 222(3):581-597, Academic Press Limited, United States (1991).

(56) References Cited

OTHER PUBLICATIONS

McCafferty, J., et al., "Phage antibodies: filamentous phage displaying antibody variable domains," Nature 348 (6301): 552-554, Macmillan Magazines Ltd, London (1990).
McCright, B., et al., "Defects in Development of the Kidney, Heart and Eye Vasculature in Mice Homozygous for a Hypomorphic Notch2 Mutation," Development 128(4):491-502, The Company of Biologists Limited, United Kingdom (2001).
McDaniell, R., et al., "NOTCH2 Mutations cause Alagille Syndrome, a Heterogeneous Disorder of the Notch Signaling Pathway," American Journal of Human Genetics 79(1):169-173, University of Chicago Press, United States (2006).
McKellar, S.H., et al., "Novel NOTCH1 Mutations in Patients with Bicuspid Aortic Valve Disease and Thoracic Aortic Aneurysms", Journal of Thoracic and Cardiovascular Surgery 134(2):290-296, St. Louis., United States (2007).
Miele, L. and Osborne, B., "Arbiter of Differentiation and Death: Notch Signaling Meets Apoptosis," Journal of Cellular Physiology 181(3):393-409, Wiley-Liss, Inc., United States (1999).
Miele, L., et al., "NOTCH Signaling as a Novel Cancer Therapeutic Target," Current Cancer Drug Targets 6(4):313-323, Bentham Science Publishers, Ltd., Netherlands (2006).
Miele, L., Gamma-Secretase and Notch Signaling: Novel Therapeutic Targets in Breast Cancer, DTIC (Online), accessed at http://www.dtic.mil/cgi-bin/GetTRDoc?Location=U2&doc=GetTRDoc.pdf&AD=ADA446389 (retrieved on Jan. 12, 2010).
Milstein, C., et al., "Hybrid hybridomas and their use in immunohistochemistry," Nature 305:537-540, Macmillan Magazines Ltd, London (1983).
Mohr, O.L. "Character Changes caused by Mutation of an Entire Region of a Chromosome in *Drosophila*," Genetics 4(3):275-282, The Genetics Society of America, United States (1919).
Monet-Lepretre, M., et al., "Distinct Phenotypic and Functional Features of CADASIL Mutations in the Notch3 Ligand Binding Domain," Brain 132(Pt 6):1601-1612, Oxford University Press, England (2009).
Mumm, J.S., et al., "A Ligand-induced Extracellular Cleavage Regulates Gamma-Secretase-Like Proteolytic Activation of Notch1," Molecular Cell 5(2):197-206, Cell Press, United States (2000).
Nam, Y., et al., "Notch Signaling as a Therapeutic Target," Current Opinion in Chemical Biology 6(4):501-509, Elsevier Science, United States (2002).
NCBI Entrez, GenBank Report, Accession No. AAA39140, Pennell, C.A., et al., Entry Date Apr. 27, 1993, accessed on Jun. 3, 2013.
NCBI Entrez, GenBank Report, Accession No. AAA60614, Elisen, L.W., et al., Entry Date Jan. 13, 1995, accessed on Jan. 4, 2013.
NCBI Entrez, GenBank Report, Accession No. P01724, Burstein, Y. and Schechter, I., Entry Date Jul. 21, 1986, last updated Nov. 4, 2008.
NCBI Entrez, GenBank Report, Accession No. Q8VDC9, Sembi, P., Entry Date Mar. 1, 2002, last updated Oct. 31, 2006.
Nelson, B.R., et al., "Transient inactivation of Notch Signaling Synchronizes Differentiation of Neural Progenitor Cells," Developmental Biology 304(2):479-498, Elsevier, United States (2007).
Nickoloff, B.J., et al., "Notch Signaling as a Therapeutic Target in Cancer: a New Approach to the Development of Cell Fate Modifying Agents," Oncogene 22(42):6598-6608, Nature Publishing Group, England (2003).
Notice of Opposition to European Patent 2152748 B2, Opponent OncoMed Pharmaceuticals, Inc., 55 pages, May 21, 2014.
Notice of Opposition to European Patent 2152748 B2, Opponent Pfizer, Inc., 18 pages, May 21, 2014.
Novus, "Biologicals Product: Mouse Monoclonal anti-Notch 1 (A6) antibody datasheet," XP008115324, accessed at http://www.novusbio.com/data_sheet/pdf_data_sheet/5985, 2006.
OncoMed Pharmaceuticals Press Release, "OncoMed Announces Abstracts Accepted at the 2014 ASCO Annual Meeting," Apr. 23, 2014, 2 pages.
OncoMed Pharmaceuticals Press Release, "OncoMed Begins Patient Dosing in Phase 2 Clinical Trial of Tarextumab (Anti-Notch 2/3, OMP-59R5) in Small Cell Lung Cancer," Dec. 1, 2014, 3 pages.
OncoMed Pharmaceuticals Press Release, "OncoMed Enrolls First Biomarker-Selected Patient in Expansion Stage of Anti-Notch1 Phase 1a Trial in Solid Tumors," Jan. 15, 2015, 2 pages.
OncoMed Pharmaceuticals Press Release, "OncoMed Pharmaceuticals Announces Presentations of Anti-Notch2/3 and Demcizumab Clinical Data at EORTC-NCI-AACR Meeting," Nov. 9, 2012, 3 pages.
OncoMed Pharmaceuticals Press Release, "OncoMed Pharmaceuticals Initiates Phase 1b/2 Clinical Trial of Anti-Cancer Stem Cell Therapeutic OMP-59R5 (Anti-Notch2/3) in Small Cell Lung Cancer (SCLC) and Amends Phase1b/2 Pancreatic Cancer Trial," May 14, 2013, 3 pages.
OncoMed Pharmaceuticals Press Release, "OncoMed Pharmaceuticals Initiates Randomized Phase 2 'ALPINE' Clinical Trial of Tarextumab (Anti-Notch 2/3, OMP-59R5) for Pancreatic Cancer," Jul. 16, 2014, 3 pages.
OncoMed Pharmaceuticals Press Release, "OncoMed Pharmaceuticals Presents Data From Clinical Trials of Four Novel Anti-Cancer Stem Cell (Anti-CSC) Therapeutics at the AACR-NCI-EORTC International Conference on Molecular Targets and Cancer Therapeutics in Boston, Oct. 19-23, 2013," Oct. 21, 2013, 4 pages.
OncoMed Pharmaceuticals Press Release, "OncoMed Pharmaceuticals Presents Data From the Phase 1b Portion of the ALPINE Clinical Study of OMP-59R5 in Pancreatic Cancer at the 2014 Gastrointestinal Cancers Symposium," Jan. 17, 2014, 3 pages.
OncoMed Pharmaceuticals Press Release, "OncoMed Pharmaceuticals Recaps New Data Presented at AACR," Apr. 3, 2012, 2 pages.
OncoMed Pharmaceuticals Press Release, "OncoMed Pharmaceuticals to Present Data From Clinical Trials of Four Novel Anti-Cancer Stem Cell (Anti-CSC) Therapeutics in Five Posters at the AACR-NCI-EORTC International Conference on Molecular Targets and Cancer Therapeutics in Boston, Oct. 19-23, 2013," Oct. 14, 2013, 4 pages.
OncoMed Pharmaceuticals Press Release, "OncoMed Pharmaceuticals to Present Data from Two Clinical Programs in Advanced Pancreatic Cancer at the 2014 Gastrointestinal Cancers Symposium," Jan. 9, 2014, 2 pages.
OncoMed Pharmaceuticals Press Release, "OncoMed Presents Biomarker-Focused Clinical Data From Phase 1a Trial of Anti-Notch1 (OMP-52M51) in Oral Plenary Session at the 26th EORTC-NCI-AACR Symposium," Nov. 19, 2014, 3 pages.
OncoMed Pharmaceuticals Press Release, "OncoMed Presents Data for Notch1 Diagnostic Assay at the 19th European Hematology Association Congress," Jun. 14, 2014, 3 pages.
OncoMed Pharmaceuticals Press Release, "OncoMed Presents Data on Multiple Anti-Cancer Stem Cell Programs at American Association for Cancer Research Annual Meeting," Apr. 8, 2014, 4 pages.
OncoMed Pharmaceuticals Press Release, "OncoMed Presents Encouraging Data From Clinical Trials of Tarextumab (Anti-Notch2/3) in Pancreatic Cancer and Small Cell Lung Cancer at the ESMO 2014 Congress," Sep. 29, 2014, 3 pages.
OncoMed Pharmaceuticals Press Release, "OncoMed Presents Final Phase 1b Safety, Efficacy and Biomarker Data for Tarextumab in Pancreatic Cancer at the 2015 Gastrointestinal Cancer Symposium," Jan. 16, 2015, 3 pages.
OncoMed Pharmaceuticals Press Release, "OncoMed Presents First-in-Human Phase I Data on Anti-Notch2/3 Antibody at ASCO," Jun. 2, 2012, 2 pages.
OncoMed Pharmaceuticals Press Release, "OncoMed Presents New Clinical and Biomarker Data From Its Tarextumab and Demcizumab Clinical Trials at the EORTC-NCI-AACR Symposium," Nov. 21, 2014, 3 pages.
OncoMed Pharmaceuticals Press Release, "OncoMed Presents New Data in Six Anti-Cancer Stem Cell Programs at AACR," Apr. 9, 2013, 3 pages.
OncoMed Pharmaceuticals Press Release, "OncoMed to Present Clinical and Preclinical Data at the 26th EORTC-NCI-AACR Symposium on Molecular Targets and Cancer Therapeutics Meeting," Oct. 30, 2014, 2 pages.

(56) References Cited

OTHER PUBLICATIONS

OncoMed Pharmaceuticals Press Release, "OncoMed to Present Clinical Data and Biomarker Analysis for Tarextumab at the 2015 Gastrointestinal Cancer Symposium," Jan. 13, 2015, 2 pages.
OncoMed Pharmaceuticals Press Release, "OncoMed to Present Data for Notch 1 Program at the 19th European Hematology Association Congress," Jun. 4, 2014, 2 pages.
OncoMed Pharmaceuticals Press Release, "OncoMed to Present Data From Three Clinical Studies at the 2014 ASCO Annual Meeting,'" May 14, 2014, 4 pages.
OncoMed Pharmaceuticals Press Release, "OncoMed to Present New and Emerging Data from Demcizumab (anti-DLL4, OMP-21M18) and Tarextumab (anti-Notch2/3, OMP-59R5) Clinical Studies at the European Society for Medical Oncology 2014 Congress," Sep. 17, 2014, 2 pages.
OncoMed Pharmaceuticals Press Release, "OncoMed to Present New Data in Six Anti-Cancer Stem Cell Programs at AACR," Apr. 2, 2013, 2 pages.
O'Reilly, E.M., et al.. "Final Results of Phase Ib of Anticancer Stem Cell Antibody Tarextumab (OMP-59R5, TRXT, anti-Notch 2/3) in Combination with Nab-Paclitaxel and Gemcitabine (Nab-P+Gem) in Patients (pts) with Untreated Metastatic Pancreatic Cancer (mPC)," 2015 Gastrointestinal Cancers Symposium, Abstract 278, 2 pages (2015).
Osbourn J., et al., "Current Methods for the Generation of Human Antibodies for the Treatment of Autoimmune Diseases," Drug Discovery Today 8(18):845-851, Elsevier Science Ltd, England (2003).
Panka, D.J., et al., "Variable region framework differences result in decreased or increased affinity of variant anti-digoxin antibodies," Proceedings of the National Academy of Sciences 85(9):3080-3084, National Academy of Sciences, United States (1988).
Parr, C., et al., "The Possible Correlation of Notch-1 and Notch-2 with Clinical Outcome and Tumour Clinicopathological Parameters in Human Breast Cancer," International Journal of Molecular Medicine 14(5):779-786, Spandidos Publications, Greece (2004).
Patnaik, A., et al., "Safety and Early Evidence of Activity of a First-in-Human Phase I Study of the Novel Cancer Stem Cell (CSC) Targeting Antibody OMP-52M51 (Anti-Notch1) Administered Intravenously to Patients with Certain Advanced Solid Tumors," Plenary Session 2 at the 26th EORTC-NCI-AACR Symposium, Nov. 19, 2014, Abstract 2, 1 page (2014).
Paul, W.E., Fundamental Immunology, Third Edition, pp. 292-295, Raven Press, United States (1993).
Paul, W.E., "Immunogenicity and Antigen Structure," in Fundamental Immunology, Third Edition, Chapter 8, p. 242, Raven Press, United States (1993).
Pear, W.S., et al., "T Cell Acute Lymphoblastic Leukemia/Lymphoma: a Human Cancer Commonly Associated with Aberrant NOTCH1 Signaling," Current Opinion in Hematology 11(6):426-433, Lippincott Williams & Wilkins, United States (2004).
Pei, Z. and Baker, N.E., "Competition between Delta and the Abruptex Domain of Notch," BMC Developmental Biology 8(4):1-14, BioMed Central, United Kingdom (2008).
Pelegrin, A., et al., "Immunotargeting of tumors: state of the art and prospects in 2000," Bull Cancer 87(11):777-791, John Libbey Eurotext, France (Nov. 2000) in the English language.
Pelegrin, A., et al., "Immunotargeting of tumors: state of the art and prospects in 2000," Bull Cancer 87(11):777-791, John Libbey Eurotext, France (Nov. 2000) in the French language.
Peters, N., et al., "CADASIL-Associated Notch3 Mutations have differential Effects both on Ligand Binding and Ligand-Induced Notch3 Receptor Signaling through RBP-Jk," Experimental Cell Research 299(2):454-464, Elsevier Science, United States (2004).
Pietanza, M.C., et al., "Phase 1b Trial of Anti-Notch 2/3 Antibody OMP-59R5 in Combination with Etoposide and Cisplatin (Ep) in Patients (Pts) with Untreated Extensive-Stage Small-Cell Lung Cancer (ED-SCLC): The Pinnacle Study," Annals of Oncology 25(Suppl 4), Published by Oxford University Press on behalf of the European Society for Medical Oncology, Abstract 1473P, 1 Page (2014).
Politi, K., et al., "Notch in Mammary Gland Development and Breast Cancer," Seminars in Cancer Biology 14(5):341-347, Academic Press, United States (2004).
Proprietor's Response to Notices of Opposition and Auxiliary Request During Opposition Procedure in European Patent 2152748 B2, 38 pages, Jan. 7, 2015.
Purow, B.W., et al., "Expression of Notch-1 and its Ligands, Delta-like-1 and Jagged-1, is Critical for Glioma Cell Survival and Proliferation," Cancer Research 65(6):2353-2363, American Association for Cancer Research, United States (2005).
Qin, J.Z., et al., "p53-Independent NOXA Induction Overcomes Apoptotic Resistance of Malignant Melanomas," Molecular Cancer Therapeutics 3(8):895-902, American Association for Cancer Research, United States (2004).
Rae, F.K., et al., "Novel Association of a Diverse Range of Genes with Renal Cell Carcinoma as Identified by differential Display," International Journal of Cance 88(5):726-732, John Wiley & Sons, Inc., United States (2000).
Rand, M.D., et al., "Calcium Binding to Tandem Repeats of EGF-like Modules. Expression and Characterization of the EGF-like Modules of Human Notch-1 Implicated in Receptor-Ligand Interactions," Protein Science 6(10):2059-2071, Cambridge University Press, United Kingdom (1997).
Rand, M.D., et al., "Calcium Depletion Dissociates and Activates Heterodimeric Notch Receptors," Molecular and Cellular Biology 20(5):1825-1835, American Society for Microbiology, United States (2000).
Real, P.J. and Ferrando, A.A., "NOTCH Inhibition and Glucocorticoid Therapy in T-Cell Acute Lymphoblastic Leukemia," Leukemia 23(8):1374-137, Macmillan Publishers Limited, United States (2009).
Rebay, I., et al., "Specific EGF Repeats of Notch Mediate Interactions with Delta and Serrate: Implications for Notch as a Multifunctional Receptor," Cell 67(4):687-699, Cell Press, United States (1991).
Reya T., et al., "Stem Cells, Cancer, and Cancer Stem Cells," Nature 414(6859):105-111, Nature Publishing Group, England (2001).
Riechmann, L., et al., "Reshaping Human Antibodies for Therapy," Nature 332(6162):323-327, Nature Publishing Group, United States (1988).
Robey, E., et al., "An Activated form of Notch Influences the Choice between CD4 and CD8 T Cell Lineages," Cell 87(3):483-492, Elsevier Science, United States (1996).
Roy, M., et al., "The Multifaceted Role of Notch in Cancer," Current Opinion in Genetics & Development 17(1):52-59, Elsevier Science, England (2007).
Rudikoff, S., et al., "Single Amino Acid Substitution Altering Antigen-Binding Specificity," Proceedings of the National Academy of Sciences 79(6):1979-1983, The National Academy of Sciences, United States (1982).
Rusanescu, G., et al., "Notch Signaling in Cardiovascular Disease and Calcification," Current Cardiology Reviews 4(3):148-156, Bentham Science Publishers, United Arab Emirates (2008).
Sakamoto, K., et al., "Distinct Roles of EGF Repeats for the Notch Signaling System," Experimental Cell Research 302(2):281-291, Elsevier Science, United States (2005).
Sambandam, A., et al., "Notch Signaling Controls the Generation and Differentiation of Early T Lineage Progenitors," Nature Immunology 6(7):663-670, Nature Publishing Group, England (2005).
Sanchez-Irizarry, C., et al., "Notch Subunit Heterodimerization and Prevention of Ligand-Independent Proteolytic Activation Depend, Respectively, on a Novel Domain and the LNR Repeats," Molecular and Cellular Biology 24(21):9265-9273, American Society for Microbiolog, United States (2004).
Sanchez-Irizarry, C., "Functional and Biochemical Characterization of the Negative Regulatory Region of Mammalian Notch," dissertation presented to The Division of Medical Sciences at Harvard University Nov. 2005.
Santa Cruz Biotechnology, Inc., "Notch 2 (25-255): sc-5545 datasheet," downloaded on Dec. 2, 2009.

(56) References Cited

OTHER PUBLICATIONS

Schroeter, E.H., et al., "Notch-1 Signalling Requires Ligand-Induced Proteolytic Release of Intracellular Domain," Nature 393(6683):382-386, Nature Publishing Group, England (1998).
Shalaby, M.R., et al., "Development of Humanized Bispecific Antibodies Reactive with Cytotoxic Lymphocytes and Tumor Cells Overexpressing the HER2 Protooncogene," The Journal of Experimental Medicine 175(1): 217-225, The Rockefeller University Press, United States (1992).
Shao, L., et al., "Fringe Modifies O-Fucose on Mouse Notch1 at Epidermal Growth Factor-like Repeats within the Ligand-Binding Site and the Abruptex Region," The Journal of Biological Chemistry 278(10):7775-7782, American Society for Biochemistry and Molecular, United States (2003).
Shawber, C., et al., "Notch Signaling Inhibits Muscle Cell Differentiation through a CBF1-Independent Pathway," Development 122(12):3765-3773, The Company of Biologists Limited, United Kingdom (1996).
Shedden.K., et al., "Characteristics of chronic lymphocytic leukemia with somatically acquired mutations in NOTCH1 exon 34", Leukemia 26(5):1108-1110, Nature Publishing Group, England (2012).
Sheets, M.D., et al., "Efficient Construction of a Large Nonimmune Phage Antibody Library: The Production of High-affinity Human Single-chain Antibodies to Protein Antigens," Proceedings of the National Academy of Sciences 95(11):6157-6162, The National Academy of Sciences, Unites States (1998).
Shimizu, K., et al., "Physical Interaction of Delta1, Jagged1, and Jagged2 with Notch1 and Notch3 Receptors," Biochemical and Biophysical Research Communications 276(1):385-389, Academic Press, United States (2000).
Shou, J., et al., "Dynamics of notch expression during murine prostate development and tumorigenesis," Cancer Research 61(19):7291-7297, American Association for Cancer Research, United States (2001).
Siebel, C.W., "PL07-04 Notch Antibody Antagonists for Cancer Therapy," Proceedings of the AACR-NCI-EORTC International Conference: Molecular Targets and Cancer Therapeutics, Oct. 22-26, 2007, Abstract nr PL07-04, 1 page, (2007).
Smith, D.C., et al., "A First-in-Human Phase I Study to Evaluate the Fully Human Monoclonal Antibody OMP-59R5 (Anti-Notch2/3) Administered Intravenously to Patients with Advanced Solid Tumors," 2012 ASCO Annual Meeting, Study 59R5-001, 18 pages (2012).
Smith, G.H., et al., "Constitutive Expression of a Truncated INT3 Gene in Mouse Mammary Epithelium Impairs Differentiation and Functional Development," Cell Growth & Differentiation 6(5):563-577, The American Association for Cancer Research, United States (1995).
Song, L.L. and Miele, L., "Cancer Stem cells—an Old Idea that's New Again: Implications for the Diagnosis and Treatment of Breast Cancer," Expert Opinion on Biological Therapy 7(4):431-438, Informa Healthcare, England (2007).
Soriano J.V., et al., "Expression of an activated Notch4(int-3) oncoprotein disrupts morphogenesis and induces an invasive phenotype in mammary epithelial cells in vitro," International Journal of Cancer 86(5):652-659, John Wiley & Sons, United States (2000).
Spigel, D.R., et al., "Phase 1b of Anticancer Stem Cell Antibody OMP-59R5 (Anti-Notch2/3) in Combination with Etoposide and Cisplatin (EP) in Patients (pts) with Untreated Extensive-Stage Small-Cell Lung Cancer (ED-SCLC)," 2014 ASCO Annual Meeting, Apr. 23, 2014, Abstract 7601, 2 Pages (2014).
Sriuranpong, V., et al., "Notch Signaling Induces Cell Cycle Arrest in Small Cell Lung Cancer Cells," Cancer Research 61(7):3200-3205, American Association for Cancer Research, United States (2001).
Sugaya, K., et al., "Gene Organization of Human NOTCH4 and (CTG)n Polymorphism in this Human Counterpart Gene of Mouse Proto-oncogene Int3," Gene 189(2):235-244, Elsevier Science B.V., Holland (1997).

Summons to attend oral proceedings pursuant to Rule 115(1) EPC for European Patent Application No. 05722705.0/2402/1718767, European Patent Office, Germany, mailed on Feb. 9, 2011.
Supplemental Data for Li, J., et al., "Modulation of Notch Signaling by Antibodies Specific for the Extracellular Negative Regulatory Region of NOTCH3," The Journal of Biological Chemistry 283:8046-8054, The American Society for Biochemistry and Molecular Biology, Inc., United States (2008), 9 pages.
Supplementary European Search Report for European Patent Application No. EP11733378, mailed on Apr. 26, 2013.
Supplementary European Search Report for European Patent Application No. EP 11733378, mailed on Apr. 17, 2013.
Supplementary European Search Report of European Application No. 08724737.5, European Patent Office, Munich Germany, mailed on Sep. 24, 2010.
Suresh, M.R., et al., "Bispecific Monoclonal Antibodies from Hybrid Hybridomas," Methods in Enzymology 121:210-228, Academic Press Inc., United States (1986).
Suzuki, T., et al.,"Imbalanced Expression of TAN-1 and Human Notch4 in Endometrial Cancers," International Journal of Oncology 17(6):1131-1139, Spandidos Publications, Greece (2000).
Swiatek, P.J., et al., "Notch1 is Essential for Postimplantation Development in Mice," Genes & Development 8(6):707-719, Cold Spring Harbor Laboratory Press, United States (1994).
Swiss-Prot_P01724. Ig lambda-1 chain V regions MOPC 104EIRPC20/J558/S104. Nov. 4, 2008. [Retrieved from the Internet on Apr. 26, 2011: <URL: http://www.ncbi.nlm.nih.gov/protein/126540?sat=OLD06&satkey=9150932>].
Swiss-Prot_Q8VDC9, Anti-MOG Z12 variable gamma 2a. Oct. 31, 2006. [Retrieved from the Internet on Jul. 11, 2011: <URL: http://www.ncbi.nlm.nih.gov/protein/Q8VDC9>].
Takebe, N., et al., "Targeting Notch Signaling Pathway in Cancer: Clinical Development Advances and Challenges," Pharmacology & therapeutics 141(2):140-149, Pergamon Press, England (2014).
Takeshita, K., et al., "Critical Role of Endothelial Notch1 Signaling in Postnatal Angiogenesis," Circulation Research 100(1):70-78, American Heart Association, United States (2007).
Talora, C., et al., "Constitutively active Notch1 induces growth arrest of HPV-positive cervical cancer cells via separate signaling pathways," Experimental Cell Research 305(2):343-354, Elsevier Science, United States (2005).
Talora, C., et al., "Specific Down-Modulation of Notch1 Signaling in Cervical Cancer Cells is Required for Sustained HPV-E6/E7 Expression and Late Steps of Malignant Transformation," Genes & Development 16(17):2252-2263, Cold Spring Harbor Laboratory Press, United States (2002).
Tanaka, M., et al., "Asymmetric Localization of Notch2 on the Microvillous Surface in Choroid Plexus Epithelial Cells," Histochemistry and Cell Biology 127(4):449-456, Springer Verlag, German (2007).
Tannock I.F. and Hill R.P., "The Basic Science of Oncology," 357-358, McGraw-Hill, United States (1998).
Tavares, M.J., et al., "Inhibition of Vascular Endothelium by the Notch-Ligand Delta-4 Unveils a Novel Therapeutic Target," Abstract#1944, Poster Board Session: 115-11, Blood 102(11):3 pages, American Society of Hematology, United States (2003).
The Extended European Search Report issued in European Application No. EP07777332.3, mailed on Aug. 11, 2009, 9 pages.
Thelu J., et al., "Notch Signalling is Linked to Epidermal Cell Differentiation Level in Basal Cell Carcinoma, Psoriasis and Wound Healing," BMC Dermatology 2(1):7, BioMed Central, England (2002).
Thermo Fisher Scientific: Notch1 Antibody (A6), Product Data Sheet, commercially available 2004, http://www.pierce-antibodies.com/products/printProductDetail/printProductDetails.cfm?js=1&format=extended&catnbr=MA1-91405.
Tolcher, A., et al., "Biomarker Analysis in the First-in-Human OMP-59R5 (Anti-Notch2/3) Phase I Study Demonstrates Pharmacodynamic (PD) Modulation of the Notch Pathway in Patients with Advanced Solid Tumors," European Journal of Cancer 48(Suppl 6):96, Elsevier, England (2012).
Tutt, A., et al., "Trispecific F(ab')3 Derivatives that use Cooperative Signaling Via the TCR/CD3 Complex and CD2 to Activate and

(56) References Cited

OTHER PUBLICATIONS

Redirect Resting Cytotoxic T Cells," The Journal of Immunology 147: 60-69, The American Association of Immunologists, United States (1991).
Uyttendaele, H., et al., "Notch4 and Wnt-1 Proteins Function to Regulate Branching Morphogeneses of Mammary Epithelial Cells in an Opposing Fashion," Developmental Biology 196(2):204-217, Elsevier Inc., Netherlands (1998).
Vajdos, F.F., et al., "Comprehensive Functional Maps of the Antigen-Binding Site of an Anti-ErbB2 Antibody obtained with Shotgun Scanning Mutagenesis," Journal of Molecular Biology 320(2):415-428, Elsevier Science, United States (2002).
Van Es, J.H., and Clevers, H., "Notch and Wnt Inhibitors as Potential New Drugs for Intestinal Neoplastic Disease," Trends in Molecular Medicine 11(11):496-502, Elsevier Inc., Netherlands (2005).
Van Es, J.H., et al., "Notch/Gamma-Secretase Inhibition Turns Proliferative Cells in Intestinal Crypts and Adenomas into Goblet Cells," Nature 435(7044):959-963, Macmillan Journals ltd, England (2005).
Van Limpt, V., et al., "SAGE Analysis of Neuroblastoma Reveals a High Expression of the Human Homologue of the Drosophila Delta Gene," Medical and Pediatric Oncology 35(6):554-558, Wiley-Liss, Inc., United States (2000).
Vardar, D., et al., "Nuclear Magnetic Resonance Structure of a Prototype Lin12-Notch Repeat Module from Human Notch1," Biochemistry 42(23):7061-7067, American Chemical Society, United States (2003).
Varnum-Finney, B., et al., "Pluripotent, Cytokine-Dependent, Hematopoietic Stem Cells are Immortalized by Constitutive Notch1 Signaling," Nature Medicine 6(11):1278-1281, Nature Publishing Group, United States (2000).
Varnum-Finney, B., et al., "The Notch Ligand, Jagged-1, Influences the Development of Primitive Hematopoietic Precursor Cells," Blood 91(11):4084-4091 , The American Society of Hematology, United States (1998).
Vaughan, T.J., et al., "Human Antibodies with Sub-nanomolar Affinities Isolated from a Large non-Immunized Phage Display Library," Nature Biotechnology 14(3):309-314, Nature Publishing Co., United States (1996).
Wallace, B., et al., "Novel NOTCH3 Activating Mutations Identified in Tumors Sensitive to OMP-59R5, a Monoclonal Antibody Targeting the Notch2 and Notch3 receptors," Proceedings of the 104th Annual Meeting of the American Association for Cancer Research, Apr. 6-10, 2013, Abstract 213, 2 pages (2013).
Weijzen, S., et al., "Activation of Notch-1 Signaling Maintains the Neoplastic Phenotype in Human Ras-Transformed Cells," Nature Medicine 8(9):979-986, Nature Publishing Group, United States (2002).
Weng, A.P. and Aster, J.C., "Multiple Niches for Notch in Cancer: Context is Everything," Current Opinion in Genetics & Development 14(1):48-54, Elsevier Science, England (2004).
Weng, A.P., et al., "Activating Mutations of NOTCH1 in Human T Cell Acute Lymphoblastic Leukemia," Science 306(5694):269-271, American Association for the Advancement of Science, United States (2004).
Weng, A.P., et al., "Growth Suppression of Pre-T Acute Lymphoblastic Leukemia Cells by Inhibition of Notch Signaling," Molecular and Cellular Biology 23(2):655-664, American Society for Microbiology, United States (2003).

Wharton, K.A., et al., "Nucleotide Sequence from the Neurogenic Locus Notch Implies a Gene Product that Shares Homology with Proteins Containing EGF-like Repeats," Cell 43(3Pt2):567-581, Cell Press, United States (1985).
Written Opinion of the International Searching Authority for International Application No. PCT/US11/21135, International Searching Authority, Alexandria, Virginia, United States, mailed Jul. 20, 2011.
Wu, H., et al., "Humanization of a Murine Monoclonal Antibody by Simultaneous Optimization of Framework and CDR Residues," Journal of Molecular Biology 294(1):151-162, Elsevier, England (1999).
Wu, Y., et al., "Therapeutic Antibody Targeting of Individual Notch Receptors," Nature 464(7291):1052-1057, Nature Publishing Group, England (2010).
Xu, A., et al., "Regions of *Drosophila* Notch that Contribute to Ligand Binding and the Modulatory Influence of Fringe," The Journal of Biological Chemistry 280(34):30158-30165, American Society for Biochemistry and Molecular Biology, United States (2005).
Xue., et al., "Embryonic Lethality and Vascular Defects in Mice Lacking the Notch Ligand Jagged1," Human Molecular Genetics 8(5):723-730, Oxford University Press, United States (1999).
Zagouras, P., et al., "Alterations in Notch Signaling in Neoplastic Lesions of the Human Cervix," Proceedings of the National Academy of Sciences 92(14):6414-6418, National Academy of Sciences, United States (1995).
Office Action mailed Nov. 20, 2013, in U.S. Appl. No. 13/773,921, inventors Lewicki, J.A., et al., filed Feb. 22, 2013.
Summons to attend oral proceedings pursuant to Rule 115(1) EPC for European Patent Application No. 08768087.2-1403/2152748, European Patent Office, Germany, mailed on Apr. 2, 2015 (R017646).
International Preliminary Report on Patentability for Application No. PCT/US2013/060878, International Bureau of WIPO, Switzerland, mailed on Mar. 24, 2015, 11 pages.
Decision Revoking European Patent for European Patent No. EP 2152748 (EP Application No. 08768087.2), European Patent Office, Rijswijk, Netherlands, dated Jul. 26, 2016, 20 pages.
Declaration by Austin Gurney, Ph.D., including Exhibits 1, 2, 3, for European Patent No. 2152748 B2 (European Patent Application No. 08768087.2), dated Apr. 20, 2016, 28 pages.
OncoMed Pharmaceuticals Press Release, "OncoMed Provides Update on Tarextumab Phase 2 Pancreatic Cancer ALPINE Trial," Jan. 25, 2016, 2 pages.
OncoMed Pharmaceuticals Press Release, "OncoMed Provides Update on Tarextumab Phase 2 Programs," Feb. 8, 2016, 3 pages.
Opponent 1's Written Submissions for Oral Proceedings, Opposition to European Patent No. 2152748 B2 (European Patent Application No. 08768087.2), dated Apr. 20, 2016, 34 pages.
Proprietor's further written submissions in response to the summons to oral proceedings dated Jun. 2, 2015 and in advance of the oral proceedings scheduled for May 20, 2016, including Annex I, Auxiliary Request 4, and Auxiliary Request 5, for European Patent No. 2152748 B2 (European Patent Application No. 08768087.2), dated May 18, 2016, 15 pages.
Westhoff, B., et al., "Alterations of the Notch Pathway in Lung Cancer," *Proceedings of the National Academy of Sciences USA* 106(52):22293-22298, National Academy of Sciences, United States (2009).

* cited by examiner

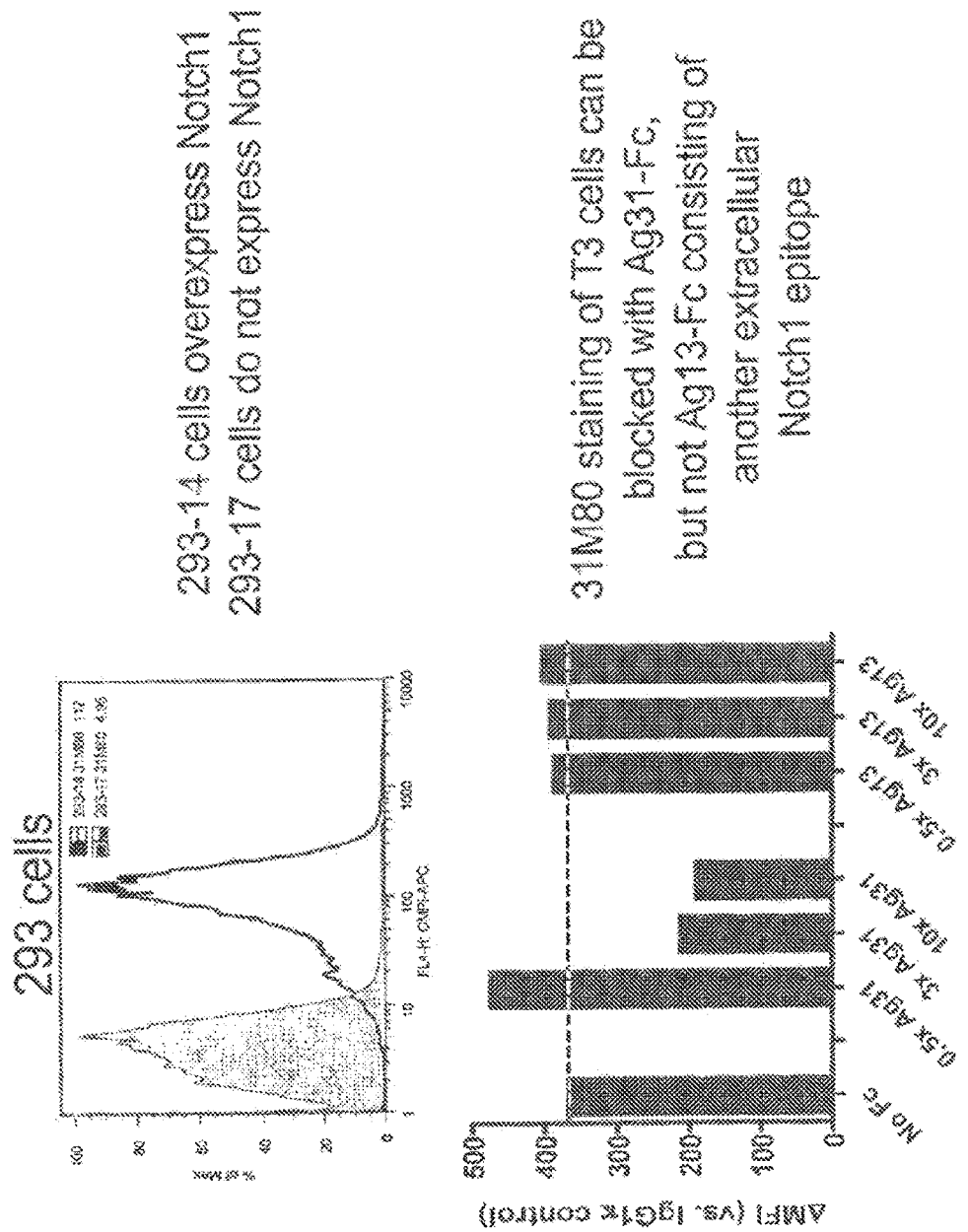

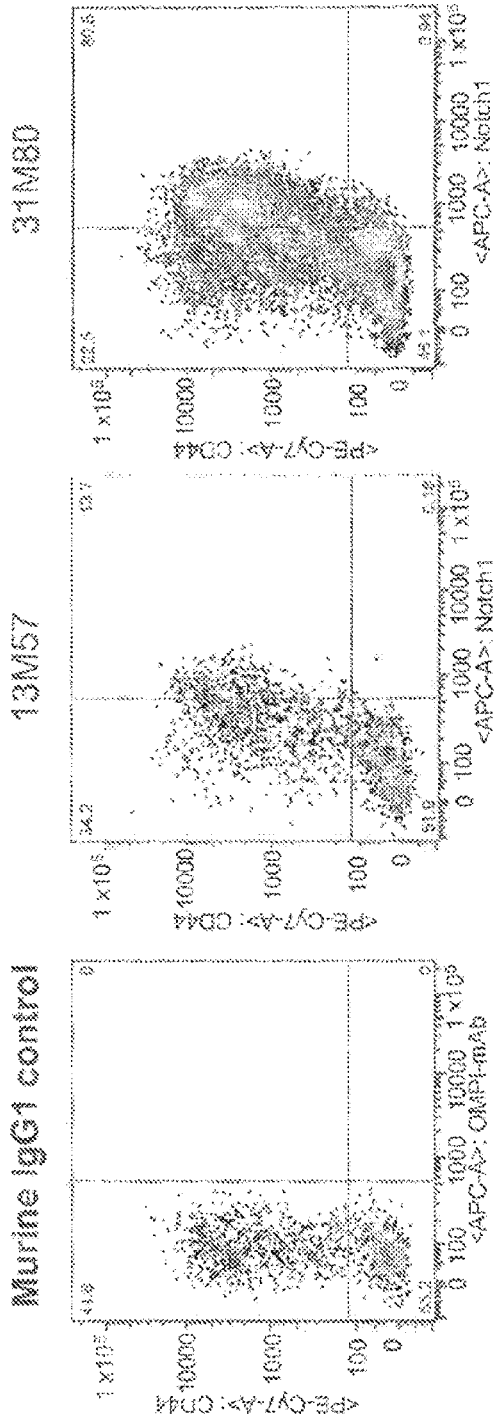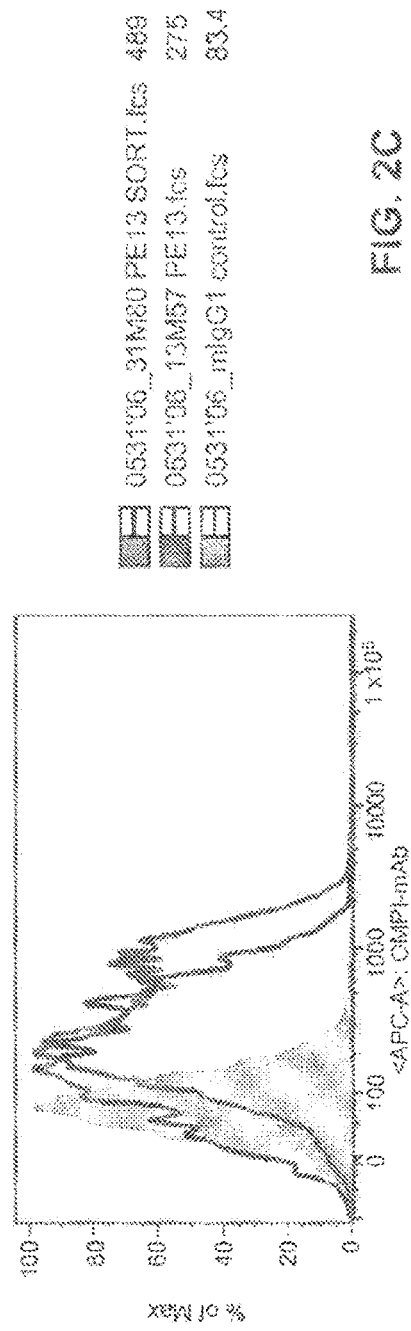
FIG. 2C

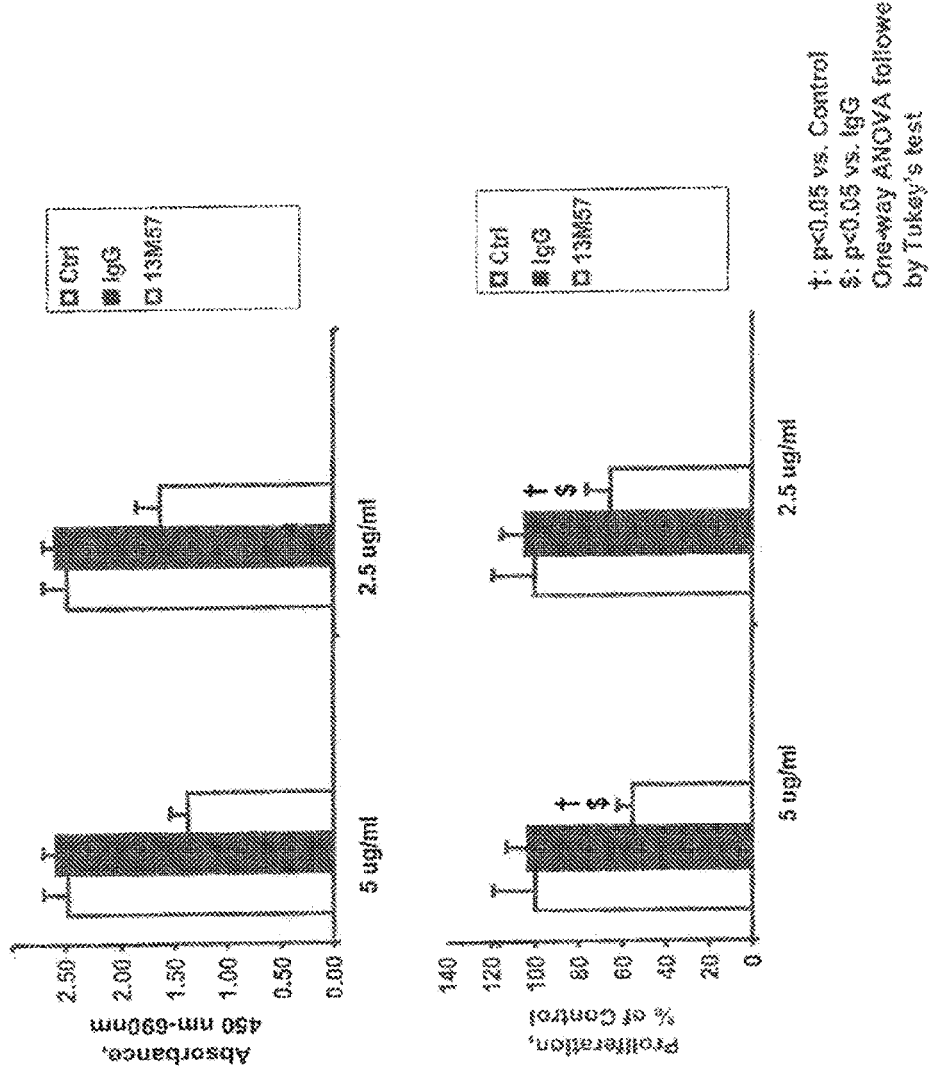
Fig. 4 Effect of Notch1 mAB on UM-T3 growth in vitro (BrdU)

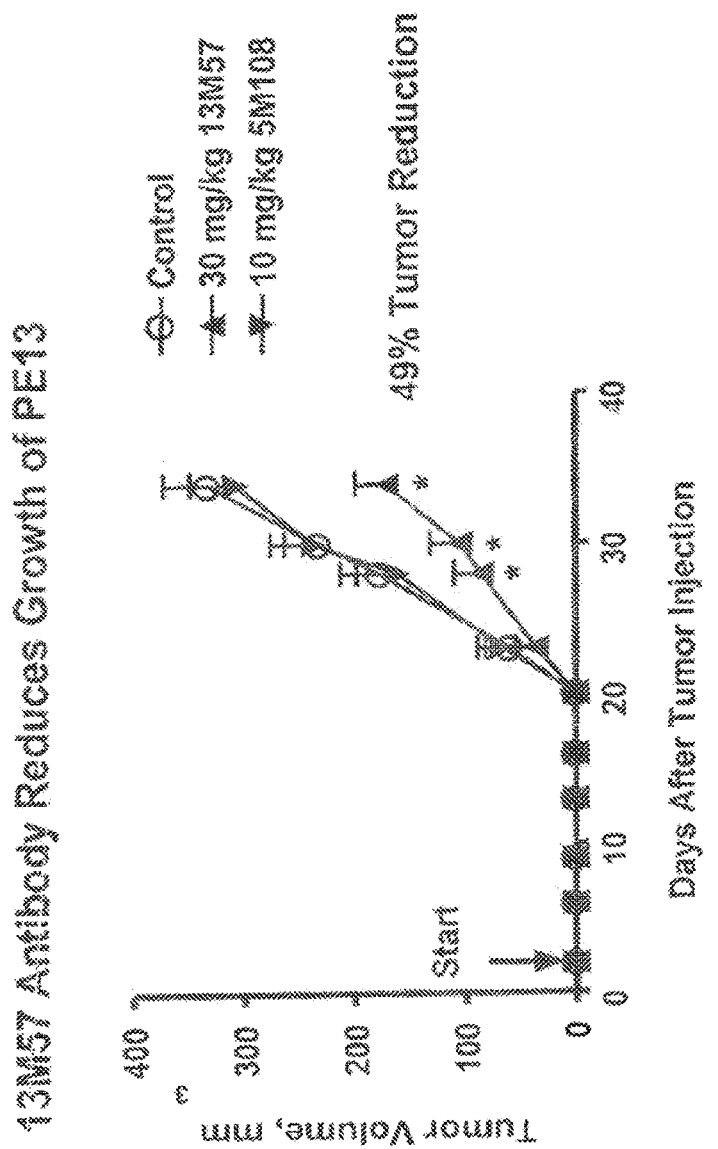

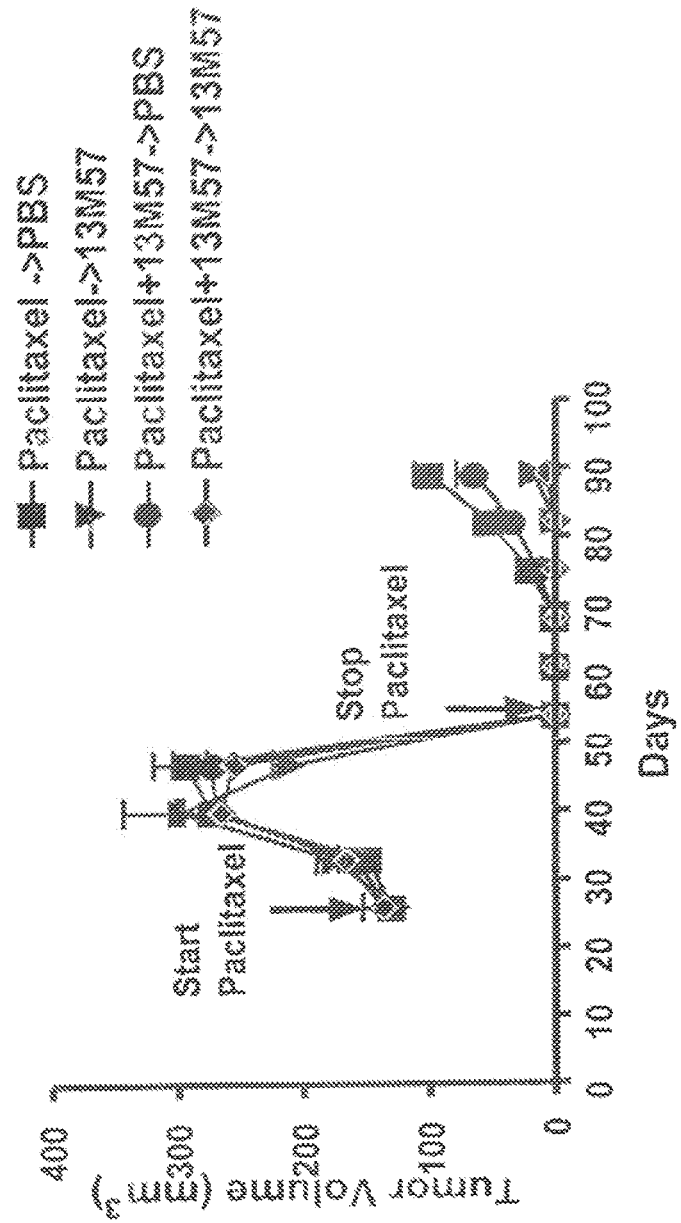

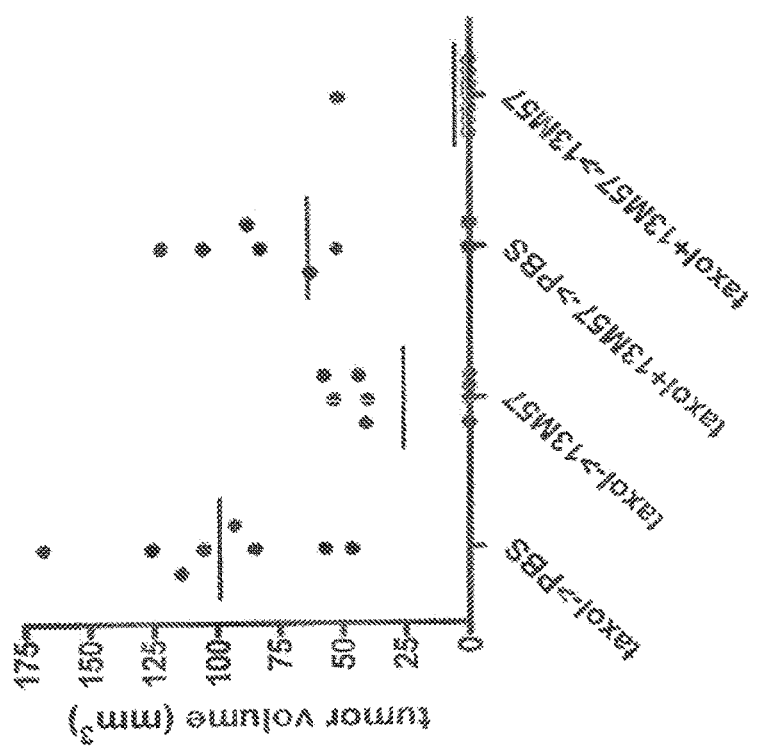

Synergy of 13M57 Anti-Notch1 and Irinotecan in C8 Colon Tumor

Synergy of 13M57 Anti-Notch1 and Irinotecan in C8 Colon Tumor

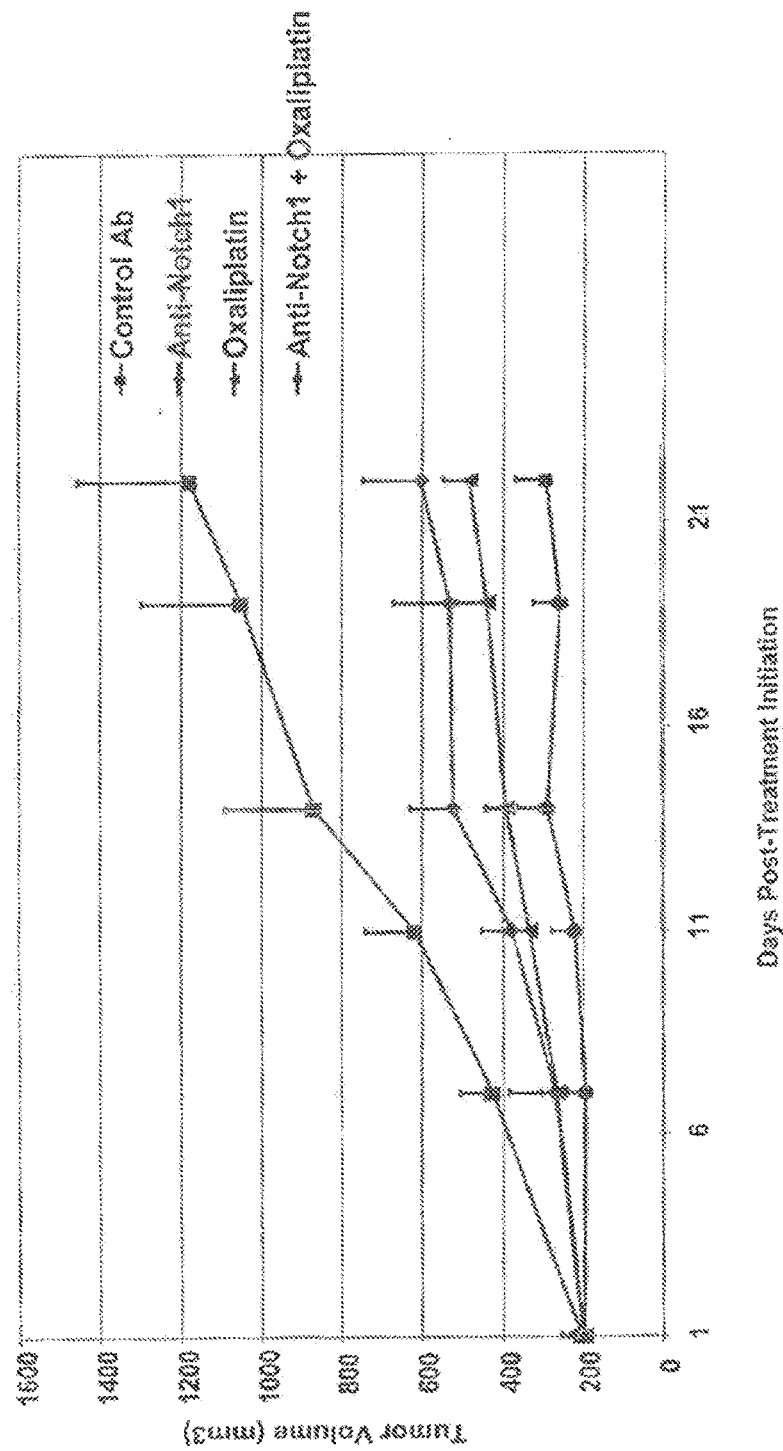
Fig. 11 Anti-Notch1 Synergizes with Oxaliplatin to Inhibit Established Colon Tumors

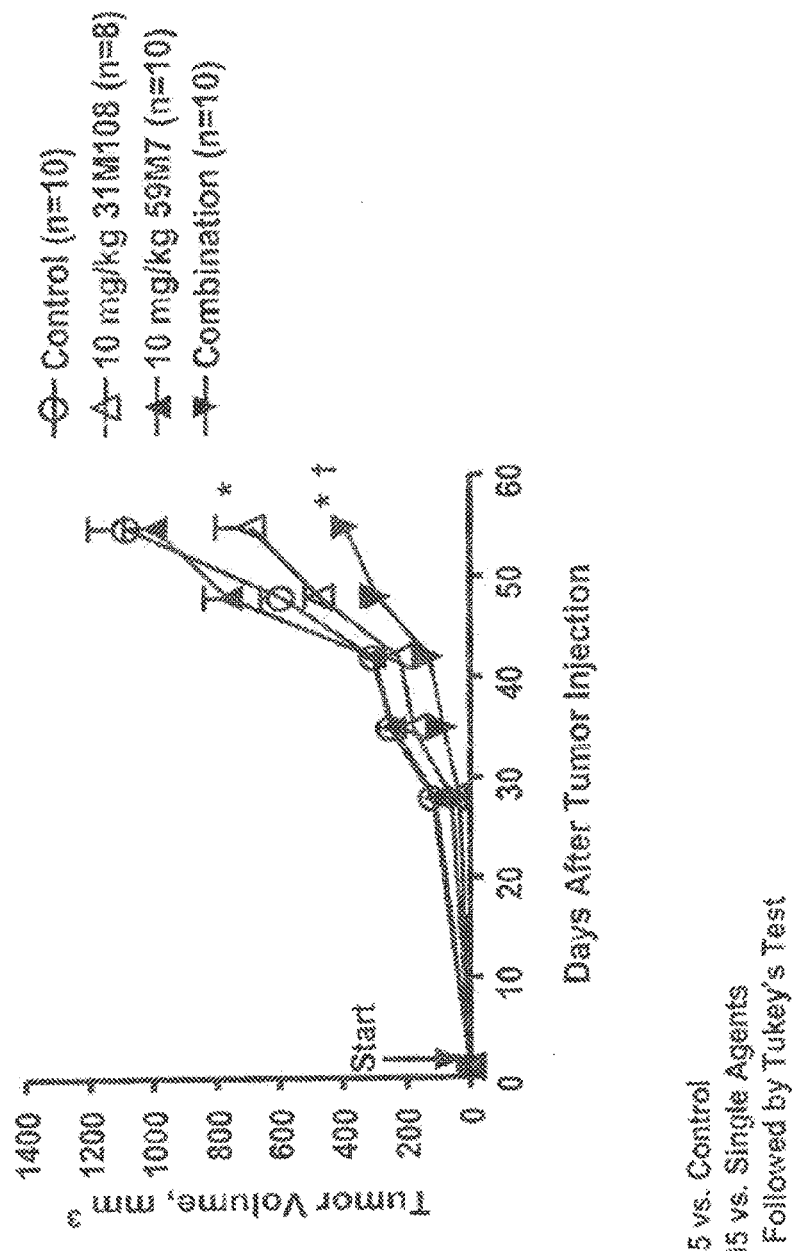

SEQUENCE LISTING

```
<160> NUMBER OF SEQ ID NOS: 19

<210> SEQ ID NO 1
<211> LENGTH: 660
<212> TYPE: DNA
<213> ORGANISM: Artificial Sequence
<220> FEATURE:
<223> OTHER INFORMATION: Synthetic NOTCH1 Polynucleotide to EGF repeats
      1-5
```

<400> SEQUENCE: 1

```
atgccgccgc tcctggcgcc cctgctctgc ctggcgctgc tgcccgcgct cgccgcacga      60
ggcccgcgat gctcccagcc cggtgagacc tgcctgaatg gcgggaagtg tgaagcggcc     120
aatggcacgg aggcctgcgt ctgtggcggg gccttcgtgg gccgcgatgc caggaccccc     180
aacccgtgcc tcagcacccc ctgcaagaac gccgggacat gccacgtggt ggaccgcaga     240
ggcgtggcag actatgcctg cagctgtgcc ctgggcttct ctgggcccct ctgcctgaca     300
cccctggaca tgcctgcct caccaacccc tgccgcaacg ggggcacctg cgacctgctc     360
acgctgacgg agtacaagtg ccgctgcccg cccggctggt cagggaaatc gtgccagcag     420
gctgacccgt gcgcctccaa ccctgcgcc aacggtggcc agtgcctgcc cttcgaggcc     480
tcctacatct gccactgccc acccagcttc catggcccca cctgccggca ggatgtcaac     540
gagtgtggcc agaagcccgg gctttgccgc cacggaggca cctgccacaa cgaggtcggc     600
tcctaccgct gcgtctgccg cgccacccac actggcccca ctgcgagcg ccctacgtg      660
```

<210> SEQ ID NO 2
<211> LENGTH: 220
<212> TYPE: PRT
<213> ORGANISM: Artificial Sequence
<220> FEATURE:
<223> OTHER INFORMATION: Synthetic NOTCH1 Polypeptide of EGF repeats 1-5

<400> SEQUENCE: 2

```
Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
            180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val
    210                 215                 220
```

<210> SEQ ID NO 3
<211> LENGTH: 202

<212> TYPE: PRT
<213> ORGANISM: Artificial Sequence
<220> FEATURE:
<223> OTHER INFORMATION: Synthetic NOTCH1 Polypeptide after putative
      signal sequence cleavage

<400> SEQUENCE: 3

```
Ala Arg Gly Pro Arg Cys Ser Gln Pro Gly Glu Thr Cys Leu Asn Gly
1               5                   10                  15

Gly Lys Cys Glu Ala Ala Asn Gly Thr Glu Ala Cys Val Cys Gly Gly
            20                  25                  30

Ala Phe Val Gly Pro Arg Cys Gln Asp Pro Asn Pro Cys Leu Ser Thr
        35                  40                  45

Pro Cys Lys Asn Ala Gly Thr Cys His Val Val Asp Arg Arg Gly Val
50                  55                  60

Ala Asp Tyr Ala Cys Ser Cys Ala Leu Gly Phe Ser Gly Pro Leu Cys
65                  70                  75                  80

Leu Thr Pro Leu Asp Asn Ala Cys Leu Thr Asn Pro Cys Arg Asn Gly
                85                  90                  95

Gly Thr Cys Asp Leu Leu Thr Leu Thr Glu Tyr Lys Cys Arg Cys Pro
            100                 105                 110

Pro Gly Trp Ser Gly Lys Ser Cys Gln Gln Ala Asp Pro Cys Ala Ser
        115                 120                 125

Asn Pro Cys Ala Asn Gly Gly Gln Cys Leu Pro Phe Glu Ala Ser Tyr
130                 135                 140

Ile Cys His Cys Pro Pro Ser Phe His Gly Pro Thr Cys Arg Gln Asp
145                 150                 155                 160

Val Asn Glu Cys Gly Gln Lys Pro Gly Leu Cys Arg His Gly Gly Thr
                165                 170                 175

Cys His Asn Glu Val Gly Ser Tyr Arg Cys Val Cys Arg Ala Thr His
            180                 185                 190

Thr Gly Pro Asn Cys Glu Arg Pro Tyr Val
        195                 200
```

<210> SEQ ID NO 4
<211> LENGTH: 1383
<212> TYPE: DNA
<213> ORGANISM: Artificial Sequence
<220> FEATURE:
<223> OTHER INFORMATION: Synthetic Nucleotide sequence of cDNA encoding
      anti-NOTCH1 monoclonal antibody 13M57 heavy chain

<400> SEQUENCE: 4

```
atgaacttcg ggctcagctt ggttttcctt gtccttattt taaagggtgt cctgtgtgag    60
gtgaacctgg tggagtctgg gggagattta gtgcagcctg agggtccct  gagactctcc   120 tgtgcagcct ctggattcac tttcagtagc tatactatgt cttgggttcg ccagactcca   180
gagaagaggc tggagtgggt cgcatacatt gattatggtg gtgatttcac ctcctattca   240
gacgctataa ggggccgatt caccatctcc agagacaatg ccaagaacac cctgtacctg   300
caaatgagca gtctgaagtc tgaggacacg gccatttatt actgttcaag acggaggtac   360
gatgctatgg actactgggg tcaaggaacc tcagtcatcg tctcttcagc caaaacgaca   420
cccccatctg tctatccact ggcccctgga tctgctgccc aaactaactc catggtgacc   480
ctgggatgcc tggtcaaggg ctatttccct gagccagtga cagtgacctg gaactctgga   540
tccctgtcca gcggtgtgca caccttccca gctgtcctgc agtctgacct ctacactctg   600
agcagctcag tgactgtccc ctccagcacc tggcccagcg agaccgtcac ctgcaacgtt   660
```

```
gcccacccgg ccagcagcac caaggtggac aagaaaattg tgcccaggga ttgtggttgt    720
aagccttgca tatgtacagt cccagaagta tcatctgtct tcatcttccc cccaaagccc    780
aaggatgtgc tcaccattac tctgactcct aaggtcacgt gtgttgtggt agacatcagc    840
aaggatgatc ccgaggtcca gttcagctgg tttgtagatg atgtggaggt gcacacagct    900
cagacgcaac cccggggagga gcagttcaac agcactttcc gctcagtcag tgaacttccc    960
atcatgcacc aggactggct caatggcaag gagttcaaat gcagggtcaa cagtgcagct   1020
ttccctgccc ccatcgagaa aaccatctcc aaaaccaaag cagaccgaa ggctccacag    1080 gtgtacacca ttccacctcc caaggagcag atggccaagg ataaagtcag tctgacctgc   1140
atgataacag acttcttccc tgaagacatt actgtggagt ggcagtggaa tgggcagcca   1200
gcggagaact acaagaacac tcagcccatc atggacacag atggctctta cttcgtctac   1260
agcaagctca atgtgcagaa gagcaactgg gaggcaggaa atactttcac ctgctctgtg   1320
ttacatgagg gcctgcacaa ccaccatact gagaagagcc tctcccactc tcctggtaaa   1380
tga                                                                  1383

<210> SEQ ID NO 5
<211> LENGTH: 460
<212> TYPE: PRT
<213> ORGANISM: Artificial Sequence
<220> FEATURE:
<223> OTHER INFORMATION: Synthetic predicted protein sequence of anti-
      NOTCH1 monoclonal antibody 13M57 IgG1 heavy chain

<400> SEQUENCE: 5

Met Asn Phe Gly Leu Ser Leu Val Phe Leu Val Leu Ile Leu Lys Gly
1               5                   10                  15

Val Leu Cys Glu Val Asn Leu Val Glu Ser Gly Gly Asp Leu Val Gln
            20                  25                  30

Pro Gly Gly Ser Leu Arg Leu Ser Cys Ala Ala Ser Gly Phe Thr Phe
        35                  40                  45

Ser Ser Tyr Thr Met Ser Trp Val Arg Gln Thr Pro Glu Lys Arg Leu
    50                  55                  60

Glu Trp Val Ala Tyr Ile Asp Tyr Gly Gly Asp Phe Thr Ser Tyr Ser
65                  70                  75                  80

Asp Ala Ile Arg Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Ile
            100                 105                 110

Tyr Tyr Cys Ser Arg Arg Arg Tyr Asp Ala Met Asp Tyr Trp Gly Gln
        115                 120                 125

Gly Thr Ser Val Ile Val Ser Ser Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Glu Thr Val Thr Cys Asn Val Ala His Pro Ala
    210                 215                 220
```

```
Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
            245                 250                 255

Pro Pro Lys Pro Lys Asp Val Leu Thr Ile Thr Leu Thr Pro Lys Val
        260                 265                 270

Thr Cys Val Val Val Asp Ile Ser Lys Asp Asp Pro Glu Val Gln Phe
    275                 280                 285

Ser Trp Phe Val Asp Asp Val Glu Val His Thr Ala Gln Thr Gln Pro
290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
        355                 360                 365

Glu Gln Met Ala Lys Asp Lys Val Ser Leu Thr Cys Met Ile Thr Asp
370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                405                 410                 415

Tyr Phe Val Tyr Ser Lys Leu Asn Val Gln Lys Ser Asn Trp Glu Ala
            420                 425                 430

Gly Asn Thr Phe Thr Cys Ser Val Leu His Glu Gly Leu His Asn His
        435                 440                 445

His Thr Glu Lys Ser Leu Ser His Ser Pro Gly Lys
    450                 455                 460

<210> SEQ ID NO 6
<211> LENGTH: 705
<212> TYPE: DNA
<213> ORGANISM: Artificial Sequence
<220> FEATURE:
<223> OTHER INFORMATION: Synthetic nucleotide sequence of cDNA encoding
      anti-NOTCH1 monoclonal antibody 13M57 light chain

<400> SEQUENCE: 6
atggtgtcct cagctcagtt ccttggtctc ctgttgctct gttttcaagg taccagatgt      60
gatatccaga tgacacagag tacctcctcc ctgtctgcct ctctgggaga cagagtcacc     120
gtcagttgca gtgcaagtca ggccattagc aattatttaa actggtatca gcagaaacca     180
gatggaactc ttaaactcct gatctattat acaacaaatt tacactcagg agtcccatca     240
aggttcagtg gcagtgggtc tgggacagat tattctctca ccatcagcaa cctggaacct     300
gaagacattg ccacttacta ttgtcaacaa tatagtaagt ttccgtggac gttcggtgga     360
ggcaccaagt tggaaatcaa acgggctgat gctgcaccaa ctgtatccat cttcccacca     420
tccagtgagc agttaacatc tggaggtgcc tcagtcgtgt gcttcttgaa caacttctac     480
cccaaagaca tcaatgtcaa gtggaagatt gatggcagtg aacgacaaaa tggcgtcctg     540
aacagttgga ctgatcagga cagcaaagac agcacctaca gcatgagcag caccctcacg     600
ttgaccaagg acgagtatga acgacataac agctatacct gtgaggccac tcacaagaca     660
```
tcaacttcac ccattgtcaa gagcttcaac aggaatgagt gttag       705

<210> SEQ ID NO 7
<211> LENGTH: 234
<212> TYPE: PRT
<213> ORGANISM: Artificial Sequence
<220> FEATURE:
<223> OTHER INFORMATION: Synthetic predicted protein sequence of anti-
      NOTCH1 monoclonal antibody 13M57 kappa light chain

<400> SEQUENCE: 7

Met Val Ser Ser Ala Gln Phe Leu Gly Leu Leu Leu Cys Phe Gln
1               5                   10                  15

Gly Thr Arg Cys Asp Ile Gln Met Thr Gln Ser Thr Ser Ser Leu Ser
            20                  25                  30

Ala Ser Leu Gly Asp Arg Val Thr Val Ser Cys Ser Ala Ser Gln Ala
        35                  40                  45

Ile Ser Asn Tyr Leu Asn Trp Tyr Gln Gln Lys Pro Asp Gly Thr Leu
    50                  55                  60

Lys Leu Leu Ile Tyr Tyr Thr Thr Asn Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Pro Glu Asp Ile Ala Thr Tyr Tyr Cys Gln Gln Tyr Ser
            100                 105                 110

Lys Phe Pro Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 8
<211> LENGTH: 38
<212> TYPE: PRT
<213> ORGANISM: Artificial Sequence
<220> FEATURE:
<223> OTHER INFORMATION: Synthetic NOTCH1 EGF repeat 4

<400> SEQUENCE: 8

Gln Ala Asp Pro Cys Ala Ser Asn Pro Cys Ala Asn Gly Gly Gln Cys
1               5                   10                  15

Leu Pro Phe Glu Ala Ser Tyr Ile Cys His Cys Pro Pro Ser Phe His
            20                  25                  30

Gly Pro Thr Cys Arg Gln
        35

<210> SEQ ID NO 9

```
<211> LENGTH: 37
<212> TYPE: PRT
<213> ORGANISM: Artificial Sequence
<220> FEATURE:
<223> OTHER INFORMATION: Synthetic NOTCH2 EGF repeat 4

<400> SEQUENCE: 9

Thr Asp Ala Cys Leu Ser His Pro Cys Ala Asn Gly Ser Thr Cys Thr
1               5                   10                  15

Thr Val Ala Asn Gln Phe Ser Cys Lys Cys Leu Thr Gly Phe Thr Gly
            20                  25                  30

Gln Lys Cys Glu Thr
        35

<210> SEQ ID NO 10
<211> LENGTH: 40
<212> TYPE: PRT
<213> ORGANISM: Artificial Sequence
<220> FEATURE:
<223> OTHER INFORMATION: Synthetic NOTCH3 EGF repeat 4

<400> SEQUENCE: 10

Ser Asp Val Asp Glu Cys Arg Val Gly Glu Pro Cys Arg His Gly Gly
1               5                   10                  15

Thr Cys Leu Asn Thr Pro Gly Ser Phe Arg Cys Gln Cys Pro Ala Gly
            20                  25                  30

Tyr Thr Gly Pro Leu Cys Glu Asn
        35                  40

<210> SEQ ID NO 11
<211> LENGTH: 37
<212> TYPE: PRT
<213> ORGANISM: Artificial Sequence
<220> FEATURE:
<223> OTHER INFORMATION: Synthetic NOTCH4 EGF repeat 4

<400> SEQUENCE: 11

Arg Asp Phe Cys Ser Ala Asn Pro Cys Val Asn Gly Gly Val Cys Leu
1               5                   10                  15

Ala Thr Tyr Pro Gln Ile Gln Cys His Cys Pro Pro Gly Phe Glu Gly
            20                  25                  30

His Ala Cys Glu Arg
        35

<210> SEQ ID NO 12
<211> LENGTH: 6
<212> TYPE: PRT
<213> ORGANISM: Artificial Sequence
<220> FEATURE:
<223> OTHER INFORMATION: Synthetic heavy chain CDR1

<400> SEQUENCE: 12

Ser Ser Tyr Thr Met Ser
1               5

<210> SEQ ID NO 13
<211> LENGTH: 17
<212> TYPE: PRT
<213> ORGANISM: Artificial Sequence
<220> FEATURE:
<223> OTHER INFORMATION: Synthetic heavy chain CDR2
```

-continued

<400> SEQUENCE: 13

Tyr Ile Asp Tyr Gly Gly Asp Phe Thr Ser Tyr Ser Asp Ala Ile Arg
1               5                   10                  15

Gly

<210> SEQ ID NO 14
<211> LENGTH: 8
<212> TYPE: PRT
<213> ORGANISM: Artificial Sequence
<220> FEATURE:
<223> OTHER INFORMATION: Synthetic heavy chain CDR3

<400> SEQUENCE: 14

Arg Arg Tyr Asp Ala Met Asp Tyr
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic light chain CDR1

<400> SEQUENCE: 15

Ser Ala Ser Gln Ala Ile Ser Asn Tyr Leu Asn
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Synthetic light chain CDR2

<400> SEQUENCE: 16

Tyr Thr Thr Asn Leu His Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic light chain CDR3

<400> SEQUENCE: 17

Gln Gln Tyr Ser Lys Phe Pro Trp Thr
1               5

<210> SEQ ID NO 18
<211> LENGTH: 681
<212> TYPE: DNA
<213> ORGANISM: Artificial Sequence
<220> FEATURE:
<223> OTHER INFORMATION: Synthetic NOTCH1 Polynucleotide to EGF repeats
      10-15

<400> SEQUENCE: 18
gcatgcatca gcaacccctg taacgagggc tccaactgcg acaccaaccc tgtcaatggc        60
aaggccatct gcacctgccc ctcggggtac acgggcccgg cctgcagcca ggacgtggat       120

```
gagtgctcgc tgggtgccaa ccccctgcgag catgcgggca agtgcatcaa cacgctgggc      180
tccttcgagt gccagtgtct gcagggctac acgggccccc gatgcgagat cgacgtcaac      240
gagtgcgtct cgaacccgtg ccagaacgac gccacctgcc tggaccagat tggggagttc      300
cagtgcatct gcatgcccgg ctacgagggt gtgcactgcg aggtcaacac agacgagtgt      360
gccagcagcc cctgcctgca caatggccgc tgcctggaca agatcaatga gttccagtgc      420
gagtgcccca cgggcttcac tgggcatctg tgccagtacg atgtggacga gtgtgccagc      480
accccctgca agaatggtgc aagtgcctg acggaccca acacttacac ctgtgtgtgc      540
acggaagggt acacggggac gcactgcgag gtggacatcg atgagtgcga ccccgacccc      600
tgccactacg gctcctgcaa ggacggcgtc gccaccttca cctgcctctg ccgcccaggc      660
tacacgggcc accactgcga g                                                681
```

<210> SEQ ID NO 19
<211> LENGTH: 227
<212> TYPE: PRT
<213> ORGANISM: Artificial Sequence
<220> FEATURE:
<223> OTHER INFORMATION: Synthetic NOTCH1 Polynucleotide to EGF repeats
      10-15

<400> SEQUENCE: 19

```
Ala Cys Ile Ser Asn Pro Cys Asn Glu Gly Ser Asn Cys Asp Thr Asn
1               5                   10                  15

Pro Val Asn Gly Lys Ala Ile Cys Thr Cys Pro Ser Gly Tyr Thr Gly
            20                  25                  30

Pro Ala Cys Ser Gln Asp Val Asp Glu Cys Ser Leu Gly Ala Asn Pro
        35                  40                  45

Cys Glu His Ala Gly Lys Cys Ile Asn Thr Leu Gly Ser Phe Glu Cys
    50                  55                  60

Gln Cys Leu Gln Gly Tyr Thr Gly Pro Arg Cys Glu Ile Asp Val Asn
65                  70                  75                  80

Glu Cys Val Ser Asn Pro Cys Gln Asn Asp Ala Thr Cys Leu Asp Gln
                85                  90                  95

Ile Gly Glu Phe Gln Cys Ile Cys Met Pro Gly Tyr Glu Gly Val His
            100                 105                 110

Cys Glu Val Asn Thr Asp Glu Cys Ala Ser Ser Pro Cys Leu His Asn
        115                 120                 125

Gly Arg Cys Leu Asp Lys Ile Asn Glu Phe Gln Cys Glu Cys Pro Thr
    130                 135                 140

Gly Phe Thr Gly His Leu Cys Gln Tyr Asp Val Asp Glu Cys Ala Ser
145                 150                 155                 160

Thr Pro Cys Lys Asn Gly Ala Lys Cys Leu Asp Gly Pro Asn Thr Tyr
                165                 170                 175

Thr Cys Val Cys Thr Glu Gly Tyr Thr Gly Thr His Cys Glu Val Asp
            180                 185                 190

Ile Asp Glu Cys Asp Pro Asp Pro Cys His Tyr Gly Ser Cys Lys Asp
        195                 200                 205

Gly Val Ala Thr Phe Thr Cys Leu Cys Arg Pro Gly Tyr Thr Gly His
    210                 215                 220

His Cys Glu
225
```

ANTIBODIES TO A NON-LIGAND BINDING REGION OF AT LEAST TWO NOTCH RECEPTORS

CROSS-REFERENCE TO RELATED APPLICATIONS

This application is a divisional of U.S. application Ser. No. 13/773,921, filed Feb. 22, 2013, now U.S. Pat. No. 8,784,811, which is a divisional of U.S. application Ser. No. 13/472,301, filed May 15, 2012, now U.S. Pat. No. 8,404,237, which is a divisional of U.S. application Ser. No. 13/010,486, filed Jan. 20, 2011, now U.S. Pat. No. 8,206,713, which is a divisional of U.S. application Ser. No. 11/806,472, filed on May 31, 2007, now U.S. Pat. No. 7,919,092, and claims the benefit of U.S. Prov. Appl. No. 60/812,955, filed Jun. 13, 2006; U.S. Prov. Appl. No. 60/879,336, filed Jan. 9, 2007; and U.S. Prov. Appl. No. 60/878,661, filed Jan. 5, 2007; each of which are herein incorporated by reference in their entirety.

BACKGROUND OF THE INVENTION

Field of the Invention

The present invention relates to compositions and methods for characterizing, diagnosing, and treating cancer. In particular, the invention provides the means and methods for diagnosis, characterization, prognosis, and treatment of cancer and specifically targeting cancer stem cells. The present invention provides an antibody that specifically binds to a non-ligand binding region of the extracellular domain of a human NOTCH receptor and inhibits growth of tumor cells. The present invention further provides a method of treating cancer, the method comprising administering a therapeutically effective amount of an antibody that specifically binds to a non-ligand binding region of the extracellular domain of a human NOTCH receptor protein and inhibits growth of tumor cells.

Background Art

Cancer is one of the leading causes of death in the developed world, resulting in over 500,000 deaths per year in the United States alone. Over one million people are diagnosed with cancer in the U.S. each year, and overall it is estimated that more than 1 in 3 people will develop some form of cancer during their lifetime. Though there are more than 200 different types of cancer, four of them—breast, lung, colorectal, and prostate account for over half of all new cases (Jemal et al., *Cancer J. Clin.* 53:5-26 (2003)).

Breast cancer is the most common cancer in woman, with an estimate 12% of women at risk of developing the disease during their lifetime. Although mortality rates have decreased due to earlier detection and improved treatments, breast cancer remains a leading cause of death in middle-aged women. Furthermore, metastatic breast cancer is still an incurable disease. On presentation, most patients with metastatic breast cancer have only one or two organ systems affected, but as the disease progresses, multiple sites usually become involved. The most common sites of metastatic involvement are locoregional recurrences in the skin and soft tissues of the chest wall, as well as in axilla and supraclavicular areas. The most common site for distant metastasis is the bone (30 40% of distant metastasis), followed by the lungs and liver. And although only approximately 1-5% of women with newly diagnosed breast cancer have distant metastasis at the time of diagnosis, approximately 50% of patients with local disease eventually relapse with metastasis within five years. At present the median survival from the manifestation of distant metastases is about three years.

Current methods of diagnosing and staging breast cancer include the tumor-node-metastasis (TNM) system that relies on tumor size, tumor presence in lymph nodes, and the presence of distant metastases as described in the American Joint Committee on Cancer: AJCC Cancer Staging Manual. Philadelphia, Pa.: Lippincott-Raven Publishers, 5th ed., 1997, pp 171-180, and in Harris. J R: "Staging of breast carcinoma" in Harris, J. R., Hellman, S., Henderson, t. C., Kinne D. W. (eds.): Breast Diseases. Philadelphia, Lippincott, 1991. These parameters are used to provide a prognosis and select an appropriate therapy. The morphologic appearance of the tumor may also be assessed but because tumors with similar histopathologic appearance can exhibit significant clinical variability, this approach has serious limitations. Finally assays for cell surface markers can be used to divide certain tumor types into subclasses. For example, one factor considered in the prognosis and treatment of breast cancer is the presence of the estrogen receptor (ER) as ER-positive breast cancers typically respond more readily to hormonal therapies such as tamoxifen or aromatase inhibitors than ER-negative tumors. Yet these analyses, though useful, are only partially predictive of the clinical behavior of breast tumors, and there is much phenotypic diversity present in breast cancers that current diagnostic tools fail to detect and current therapies fail to treat.

Prostate cancer is the most common cancer in men in the developed world, representing an estimated 33% of all new cancer cases in the U.S., and is the second most frequent cause of death (Jemal et al., 2003, CA Cancer J. Clin. 53:5-26). Since the introduction of the prostate specific antigen (PSA) blood test, early detection of prostate cancer has dramatically improved survival rates, and the five year survival rate for patients with local and regional stage prostate cancers at the time of diagnosis is nearing 100%. Yet more than 50% of patients will eventually develop locally advanced or metastatic disease (Muthuramalingam et al., 2004, Clin. Oncol. 16:505-16).

Currently radical prostatectomy and radiation therapy provide curative treatment for the majority of localized prostate tumors. However, therapeutic options are very limited for advanced cases. For metastatic disease, androgen ablation with luteinising hormone-releasing hormone (LHRH) agonist alone or in combination with anti-androgens is the standard treatment. Yet despite maximal androgen blockage, the disease nearly always progresses with the majority developing androgen-independent disease. At present there is no uniformly accepted treatment for hormone refractory prostate cancer, and chemotherapeutic regimes are commonly used (Muthuramalingam et al., 2004, Clin. Oncol. 16:505-16; Trojan et al., 2005, Anticancer Res. 25:551-61).

Colorectal cancer is the third most common cancer and the fourth most frequent cause of cancer deaths worldwide (Weitz et al., 2005, Lancet 365:153-65). Approximately 5-10% of all colorectal cancers are hereditary with one of the main forms being familial adenomatous polyposis (FAP), an autosomal dominant disease in which about 80% of affected individuals contain a germline mutation in the adenomatous polyposis coli (APC) gene. Colorectal carcinoma has a tendency to invade locally by circumferential growth and elsewhere by lymphatic, hematogenous, transperitoneal, and perineural spread. The most common site of extralymphatic involvement is the liver, with the lungs the most frequently affected extra-abdominal organ. Other sites of hematogenous spread include the bones, kidneys, adrenal glands, and brain.

The current staging system for colorectal cancer is based on the degree of tumor penetration through the bowel wall and the presence or absence of nodal involvement. This staging system is defined by three major Duke's classifications: Duke's A disease is confined to submucosa layers of colon or rectum; Duke's B disease has tumors that invade through the muscularis propria and may penetrate the wall of the colon or rectum; and Duke's C disease includes any degree of bowel wall invasion with regional lymph node metastasis. While surgical resection is highly effective for early stage colorectal cancers, providing cure rates of 95% in Duke's A patients, the rate is reduced to 75% in Duke's B patients and the presence of positive lymph node in Duke's C disease predicts a 60% likelihood of recurrence within five years. Treatment of Duke's C patients with a post surgical course of chemotherapy reduces the recurrence rate to 40%-50%, and is now the standard of care for these patients.

Lung cancer is the most common cancer worldwide, the third most commonly diagnosed cancer in the United States, and by far the most frequent cause of cancer deaths (Spiro et al., 2002, Am. J. Respir. Crit. Care Med. 166:1166-96; Jemal et al., 2003, CA Cancer J. Clin. 53:5-26). Cigarette smoking is believed responsible for an estimated 87% of all lung cancers, making it the most deadly preventable disease. Lung cancer is divided into two major types that account for over 90% of all lung cancers: small cell lung cancer (SCLC) and non-small cell lung cancer (NSCLC). SCLC accounts for 15-20% of cases and is characterized by its origin in large central airways and histological composition of sheets of small cells with little cytoplasm. SCLC is more aggressive than NSCLC, growing rapidly and metastasizing early and often. NSCLC accounts for 80-85% of all cases and is further divided into three major subtypes based on histology: adenocarcinoma, squamous cell carcinoma (epidermoid carcinoma), and large cell undifferentiated carcinoma.

Lung cancer typically presents late in its course, and thus has a median survival of only 6-12 months after diagnosis and an overall 5 year survival rate of only 5-10%. Although surgery offers the best chance of a cure, only a small fraction of lung cancer patients are eligible with the majority relying on chemotherapy and radiotherapy. Despite attempts to manipulate the timing and dose intensity of these therapies, survival rates have increased little over the last 15 years (Spiro et al., 2002, Am. J. Respir. Crit. Care Med. 166:1166-96).

Cancer arises from dysregulation of the mechanisms that control normal tissue development and maintenance, and increasingly stem cells are thought to play a central role (Beachy et al., 2004, Nature 432:324). During normal animal development, cells of most or all tissues are derived from normal precursors, called stem cells (Morrison et al., 1997, Cell 88:287-98; Morrison et al., 1997, Curr. Opin. Immunol. 9:216-21; Morrison et al., 1995, Annu. Rev. Cell. Dev. Biol. 11:35-71). Stem cells are cell that: (1) have extensive proliferative capacity; 2) are capable of asymmetric cell division to generate one or more kinds of progeny with reduced proliferative and/or developmental potential; and (3) are capable of symmetric cell divisions for self-renewal or self-maintenance. The best-known example of adult cell renewal by the differentiation of stem cells is the hematopoietic system where developmentally immature precursors (hematopoietic stem and progenitor cells) respond to molecular signals to form the varied blood and lymphoid cell types. Other cells, including cells of the gut, breast ductal system, and skin are constantly replenished from a small population of stem cells in each tissue, and recent studies suggest that most other adult tissues also harbor stem cells, including the brain.

Solid tumors are composed of heterogeneous cell populations. For example, breast cancers are a mixture of cancer cells and normal cells, including mesenchymal (stromal) cells, inflammatory cells, and endothelial cells. Classic models of cancer hold that phenotypically distinct cancer cell populations all have the capacity to proliferate and give rise to a new tumor. In the classical model, tumor cell heterogeneity results from environmental factors as well as ongoing mutations within cancer cells resulting in a diverse population of tumorigenic cells. This model rests on the idea that all populations of tumor cells would have some degree of tumorigenic potential. (Pandis et al 1998, Genes, Chromosomes & Cancer 12:122-129; Kuukasjrvi et al., 1997, Cancer Res. 57:1597-1604; Bonsing et al., 1993, Cancer 71:382-391; Bonsing et al., 2000, Genes Chromosomes & Cancer 82: 173-183; Beerman H et al., 1991, Cytometry. 12:147-54; Aubele M &. Werner M, 1999, Analyt. Cell. Path. 19:53; Shen L et al., 2000, Cancer Res. 60:3884).

An alternative model for the observed solid tumor cell heterogeneity is that solid tumors result from a "solid tumor stem cell" (or "cancer stem cell" from a solid tumor) that subsequently undergoes chaotic development through both symmetric and asymmetric rounds of cell divisions. In this stem cell model, solid tumors contain a distinct and limited (possibly even rare) subset of cells that share the properties of normal "stem cells", in that they extensively proliferate and efficiently give rise both to additional solid tumor stem cells (self-renewal) and to the majority of tumor cells of a solid tumor that lack tumorigenic potential. Indeed, mutations within a long-lived stem cell population may initiate the formation of cancer stem cells that underlie the growth and maintenance of tumors and whose presence contributes to the failure of current therapeutic approaches.

The stem cell nature of cancer was first revealed in the blood cancer, acute myeloid leukemia (AML) (Lapidot et al., 1994, Nature 17:645-8). More recently it has been demonstrated that malignant human breast tumors similarly harbor a small, distinct population of cancer stem cells enriched for the ability to form tumors in immunodeficient mice. An ESA+, CD44+, CD24–/low, Lin-cell population was found to be 50-fold enriched for tumorigenic cells compared to unfractionated tumor cells (Al-Hajj et al., 2003, PNAS 100:3983-8). The ability to prospectively isolate the tumorigenic cancer cells has permitted investigation of critical biological pathways that underlie tumorigenicity in these cells, and thus promises the development of better diagnostic assays and therapeutics for cancer patients. It is toward this purpose that this invention is directed.

BRIEF SUMMARY OF THE INVENTION

The present invention provides a method of treating cancer, wherein the cancer comprises cancer stem cells, comprising administering to the subject a therapeutically effective amount of an antibody which binds a cancer stem cell marker. In a more particular aspect, the present invention provides a method of treating cancer, wherein the cancer comprises stem cells expressing one or more Notch receptor family members, comprising administering to the subject a therapeutically effective amount of an antibody that binds those Notch receptor family members or the ligands to those Notch receptors. The present invention for the first time identifies antibodies that bind to the non-ligand binding domain of the extracellular domain of a human NOTCH receptor as therapeutically effective against cancer. Thus in certain embodiments the present invention provides an antibody that specifically binds to a non-ligand binding region of the extracellular domain of a human NOTCH receptor and inhibits growth of tumor cells. In certain embodiments, the present invention further provides a method of treating cancer, the method comprising administering a therapeutically effective amount of an antibody that specifically binds to a non-ligand binding region of the extracellular domain of a human NOTCH receptor protein and inhibits growth of tumor cells.

Various advantages in using an antibody that binds Notch receptor family members or the ligands to those Notch receptors to treat such cancer are contemplated herein. In particular, certain Notch receptors are highly expressed in certain solid tumors, for example, breast and colon, and this provides a sink for active drug where the drug binds to the Notch receptor. Antibodies that bind overexpressed Notch receptors are anticipated to have a better safety profile than currently available chemotherapeutic drugs.

The invention further provides a method of treating cancer in a human, wherein the cancer comprising cancer stem cells is not characterized by overexpression by the cancer stem cell of one or more Notch receptors, comprising administering to the human a therapeutically effective amount of an antibody which binds to a Notch receptor and blocks ligand activation of a Notch receptor.

The invention further provides a method of treating cancer in a human comprising administering to the human therapeutically effective amounts of (a) a first antibody which binds a Notch receptor and inhibits growth of cancer stem cells which overexpress Notch receptors; and (h) a second antibody which binds a Notch receptor and blocks ligand activation of a Notch receptor.

The invention also provides a method of treating cancer, wherein the cancer is selected from the group consisting of breast, colon, rectal and colorectal cancer, comprising administering a therapeutically effective amount of an antibody which binds Notch. The invention also provides another method of treating cancer, wherein the cancer is selected from the group consisting of breast, colon, pancreatic, prostate, lung, rectal and colorectal cancer, comprising administering a therapeutically effective amount of an antibody that blocks ligand activation of a Notch receptor. The invention also provides still another method of treating cancer, wherein the cancer is selected from the group consisting of breast, colon, pancreatic, prostate, lung, rectal and colorectal cancer, comprising administering a therapeutically effective amount of an antibody that binds Notch and an antibody that blocks ligand activation of a Notch receptor.

In further embodiments, the invention provides articles of manufacture for use (among other things) in the above methods. For example, the invention provides an article of manufacture comprising a container and a composition contained therein, wherein the composition comprises an antibody that binds Notch, and further comprises a package insert indicating that the composition can be used to treat cancer comprising cancer stem cells. Another example, the invention provides an article of manufacture comprising a container and a composition contained therein, wherein the composition comprises an antibody that binds Notch, and further comprises a package insert indicating that the composition can be used to treat cancer comprising cancer stem cells that express one or more Notch receptors.

The invention additionally pertains to an article of manufacture comprising container and a composition contained therein, wherein the composition comprises an antibody which binds a Notch receptor and blocks ligand activation of a Notch receptor, and further comprises a package insert indicating that the composition can be used to treat cancer, wherein the cancer comprises cancer stem cells that are not characterized by overexpression of the Notch receptor.

In certain embodiments, an article of manufacture is provided which comprises (a) a first container with a composition contained therein, wherein the composition comprises a first antibody that binds a Notch receptor and inhibits growth of cancer cells comprising cancer stem cells overexpressing Notch; and (b) a second container with a composition contained therein, wherein the composition comprises a second antibody which binds Notch and blocks ligand activation of a Notch receptor.

A further article of manufacture is provided which comprises a container and a composition contained therein, wherein the composition comprises an antibody which hinds Notch and blocks ligand activation of a Notch receptor, and further comprises a package insert indicating that the composition can be used to treat a cancer selected from the group consisting of colon, pancreatic, prostate, lung, rectal and colorectal cancer.

The invention additionally provides: a humanized antibody which binds Notch and blocks ligand activation of a Notch receptor; a composition comprising the humanized antibody and a pharmaceutically acceptable carrier; and an immunoconjugate comprising the humanized antibody conjugated with a cytotoxic agent.

Moreover, the invention provides isolated nucleic acid encoding the humanized antibody; a vector comprising the nucleic acid; a host cell comprising the nucleic acid or the vector; as well as a process of producing the humanized antibody comprising culturing a host cell comprising the nucleic acid so that the nucleic acid is expressed and, optionally, further comprising recovering the humanized antibody from the host cell culture (e.g. from the host cell culture medium).

The invention further pertains to an immunoconjugate comprising an antibody that binds Notch conjugated to one or more calicheamicin molecules, and the use of such conjugates for treating Notch expressing cancer, e.g.; a cancer in which cancer stem cells overexpress Notch.

In another aspect, the present invention provides a method of treating cancer, wherein the cancer comprises cancer stem cells, comprising administering to the subject a therapeutically effective amount of a receptor fusion protein which binds a ligand to a cancer stem cell marker. In a more particular aspect, the present invention provides a method of treating cancer, wherein the cancer comprises stem cells overexpressing one or more Notch receptor family members, comprising administering to the subject a therapeutically effective amount of a receptor fusion protein that binds one or more ligands to those Notch receptor family members.

The invention further provides a method of treating cancer in a human, wherein the cancer comprising cancer stem cells is not characterized by overexpression by the cancer stem cell of one or more Notch receptors, comprising administering to the human a therapeutically effective amount of a receptor fusion protein which binds to one or more ligands to Notch receptor.

The invention further provides a method of treating cancer a human comprising administering to the human therapeutically effective amounts of (a) a receptor fusion protein which binds ligand to a Notch receptor and blocks ligand activation of a Notch receptor; and (b) an antibody which binds a Notch receptor and inhibits growth of cancer stem cells which overexpress Notch receptors.

The invention also provides a method of treating cancer, wherein the cancer is selected from the group consisting of breast, colon, pancreatic, rectal and colorectal cancer, comprising administering a therapeutically effective amount of a receptor fusion protein which binds one or more ligands to a Notch receptor. The invention also provides still another method of treating cancer, wherein the cancer is selected from the group consisting of breast, colon, pancreatic, rectal and colorectal cancer, comprising administering a therapeutically effective amount of a receptor fusion protein that blocks ligand activation of a Notch receptor and an antibody that binds a Notch receptor and inhibits growth of cancer stem cells which overexpress Notch receptors.

In further embodiments, the invention provides articles of manufacture for use (among other things) in the above methods. For example, the invention provides an article of manufacture comprising a container and a composition contained therein, wherein the composition comprises a receptor fusion protein that blocks ligand activation of a Notch receptor, and further comprising a package insert indicating that the composition can be used to treat cancer comprising cancer stem cells. Another example, the invention provides an article of manufacture comprising a container and a composition contained therein, wherein the composition comprises a receptor fusion protein that blocks ligand activation of a Notch receptor, and further comprising a package insert indicating that the composition can be used to treat cancer comprising cancer stem cells that express one or more Notch receptors.

The invention additionally pertains to an article of manufacture comprising a container and a composition contained therein, wherein the composition comprises a receptor fusion protein which blocks ligand activation of a Notch receptor, and further comprises a package insert indicating that the composition can be used to treat cancer, wherein the cancer comprises cancer stem cells that are not characterized by overexpression of the Notch receptor.

In a further embodiment, an article of manufacture is provided which comprises (a) a first container with a composition contained therein, wherein the composition comprises a receptor fusion protein which blocks ligand activation of a Notch receptor; and (b) a second container with a composition contained therein, wherein the composition comprises an antibody that binds a Notch receptor and inhibits growth of cancer cells comprising cancer stem cells overexpressing Notch.

A further article of manufacture is provided which comprises a container and a composition contained therein, wherein the composition comprises a receptor fusion protein that blocks ligand activation of a Notch receptor, and further comprises a package insert indicating that the composition can be used to treat a cancer selected from the group consisting of colon, pancreatic, prostate, lung, rectal and colorectal cancer.

Examples of solid tumors that can be treated using a therapeutic composition of the instant invention, for example, an antibody that binds Notch or a receptor fusion protein that blocks ligand activation of a Notch receptor include, but are not limited to, sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. The invention is applicable to sarcomas and epithelial cancers, such as ovarian cancers and breast cancers.

BRIEF DESCRIPTION OF THE DRAWINGS/FIGURES

Figure 1B:
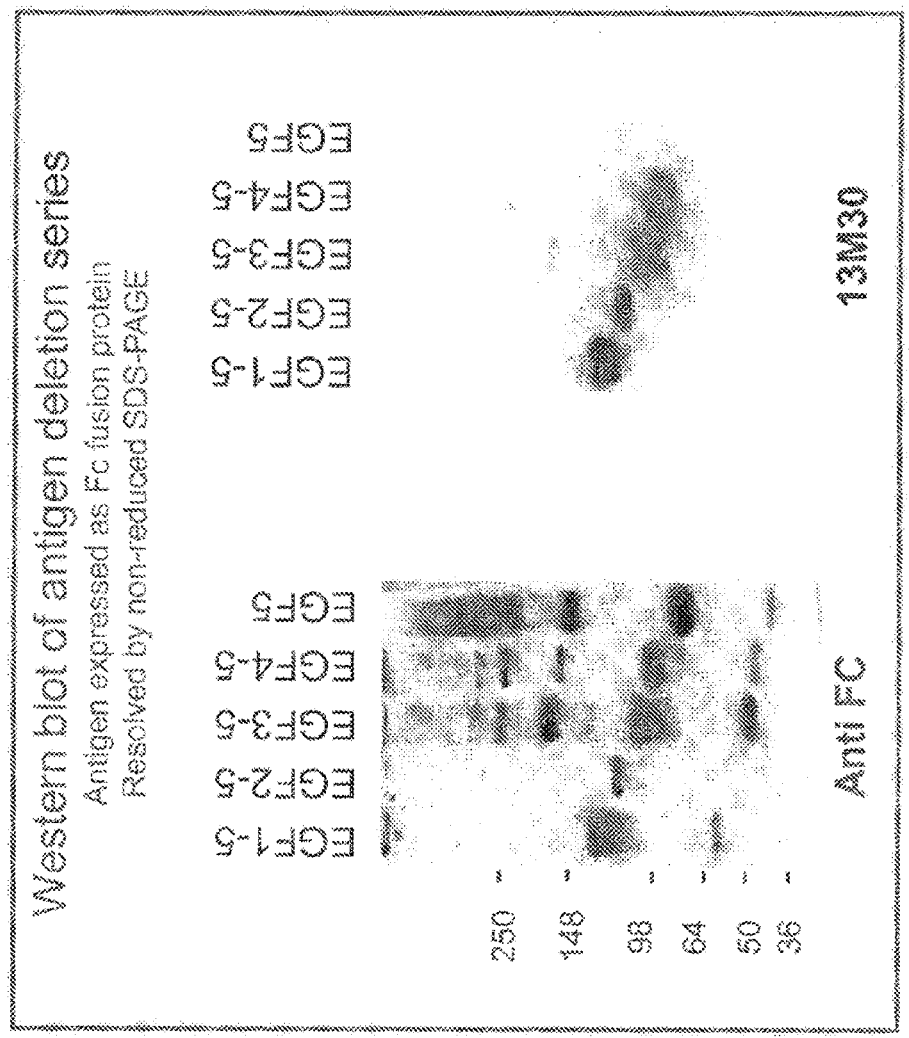
Figure 1C:
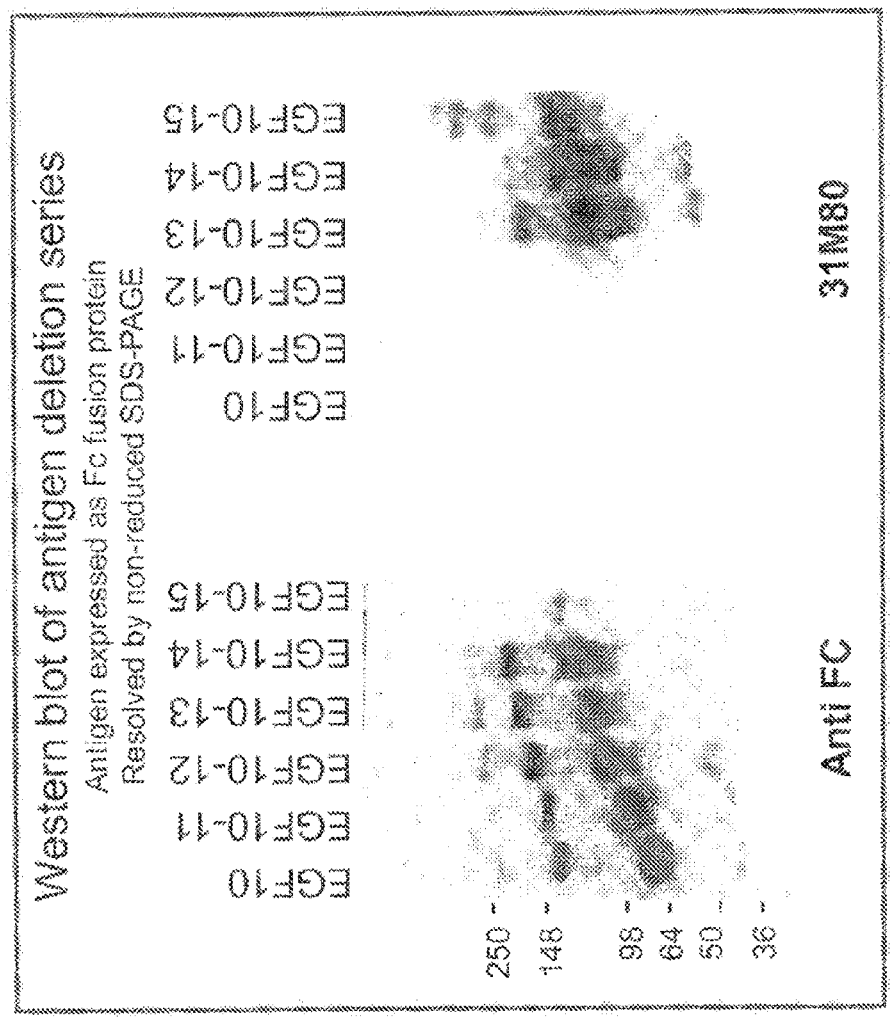

FIGS. 1A, 1B, and 1C: Epitope mapping of anti-NOTCH1 monoclonal antibodies that bind to non-ligand binding domains. Fe fusion proteins containing a deletion series of NOTCH1 EGF domains 1-5 (A, B) or 10-15 (C) were separated by SDS-PAGE and blotted with monoclonal antibody 13M57 (A, B) or 31M80 (C). In contrast to anti-Fe antibodies that detected fusion proteins in all lanes, antibody 13M57 only detected fusion proteins containing EGF repeat 4 including EGF 1-4 and EGF 1-5 but not EGF 1-3 (A); and FOE 4-5 but not EGF 5 alone (B). Similarly, antibody 31M80 only detected fusion proteins containing EGF repeat 13 (C).

FIGS. 2A, 2B, 2C, and 2D: Binding of anti-NOTCH1 monoclonal antibody 13M57 and 31M80 to cell surface expressed NOTCH1. (A) FACS analysis of cells co-expressing full length NOTCH1 receptor and GFP incubated with, from left to right, IgG1 control antibodies, 13M57 and anti-human NOTCH1 EGF 1-5 antisera, (B) FAC analysis of mock transfected cells or cells expressing full length NOTCH1 receptor incubated with anti-NOTCH1 receptor antibody 31M80 demonstrates that 31M80 specifically recognizes NOTCH1 receptor. Antibody binding relative to an NG control antibody is inhibited by increasing amounts of antigen protein containing EGF repeats 10-16 linked to human Fc (0.5×, 3×, and 10×Ag31) but not antigen protein containing EGF repeats 1-5 linked to Fc (0.5×, 3×, and 10×Ag13). (C) Anti-NOTCH1 antibodies 13M57 and 31M80 showed increased binding to PE13 breast tumor cells compared to an isotype control antibody (bottom) and this binding corresponded to cells that express high levels of ESA and CD44 (top: CD44 x-axis and NOTCH1 y-axis). Cells isolated for a tumorigenicity study are indicated in the flow cytometry results for antibody 31M80. (D) Anti-NOTCH1 antibody 31M80 showed increased binding to dissociated colon tumor cells from two different patients compared to an isotype antibody control.

Figure 3:
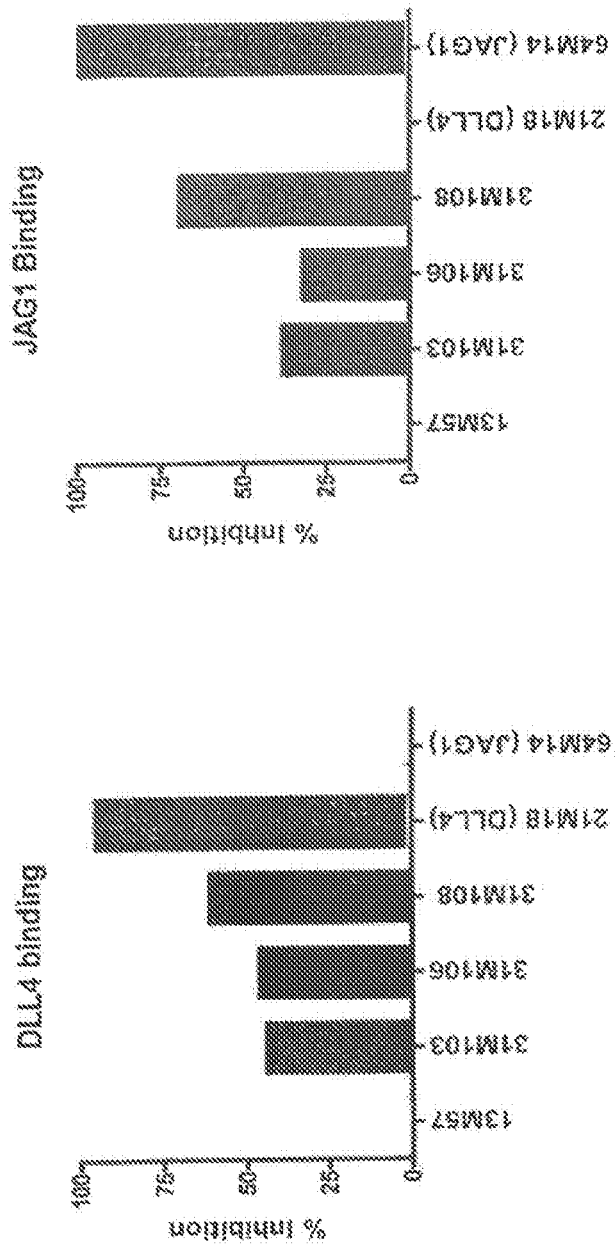

FIG. 3: Antibodies Against NOTCH1 EGF13 and EGF4 Fail to Effectively Block Ligand Binding. NOTCH1 expressing HEK 293 cells were incubated with either DLL4-Fc (left) or JAG1-Fc (right) in the presence of anti-NOTCH1 antibodies (13M57, 31M103, 31M106, or 31M108) or control anti-DLL4 (21M18) or anti-JAG1 (64M14) antibodies. Binding of Fe fusion proteins to NOTCH1-expressing cells was detected by a PE-conjugated goat anti-Fe antibody and flow cytometry. Inhibition of ligand binding by anti-NOTCH1 antibodies was expressed as a percentage of inhibition by the control ligand antibodies. Anti-NOTCH1 antibodies 31M103, 31M106, and 31M108, all of which specifically bind to EGF13, only partially inhibit ligand binding. 31M108 showed between 50-75% inhibition compared to the ligand antibodies. Similarly, 31M103 and 31M106 showed only between 25-50% inhibition. In contrast, 13M57 showed no inhibition of ligand binding when compared to inhibition by anti-DLL4 or anti-JAG1 antibodies.

FIG. 4: Effect of NOTCH1 Monoclonal Antibodies against EGF4 on Breast Tumor Cell Growth In Vitro. Breast tumor cells were cultured in the presence of 2.5 ug/mL or 5 ug/mL anti-NOTCH1 antibody, control murine IgG or no antibody for three days followed by 18 hours of BrdU labeling. As shown on the top graphs, breast tumor cells cultured in the presence of anti-NOTCH1 antibody 13M57 showed a decreased 450 nm/690 nm absorbance ratio compared to controls. As a percentage of no antibody control, the presence of anti-NOTCH1 antibodies resulted in a statistically significant decrease by one-way ANOVA followed by Tukey's test in the proliferation of breast tumor cells compared to no antibody control ($p<0.5$) or control IgG ($p<0.05$) (bottom).

FIG. 5: Effect of NOTCH1 Monoclonal Antibody 13M57 on PE-13 Tumor Cells In Vivo. NOD/SCID mice injected with PE-13 tumor cells were treated with PBS or anti-NOTCH1 antibodies 3 days after cell injection, and the growth of tumor cells was determine twice a week. Total tumor volume was significantly reduced by 49% ($p<0.05$) in animals treated with anti-NOTCH antibodies 13M57 compared to PBS injected controls.

Figure 6A:
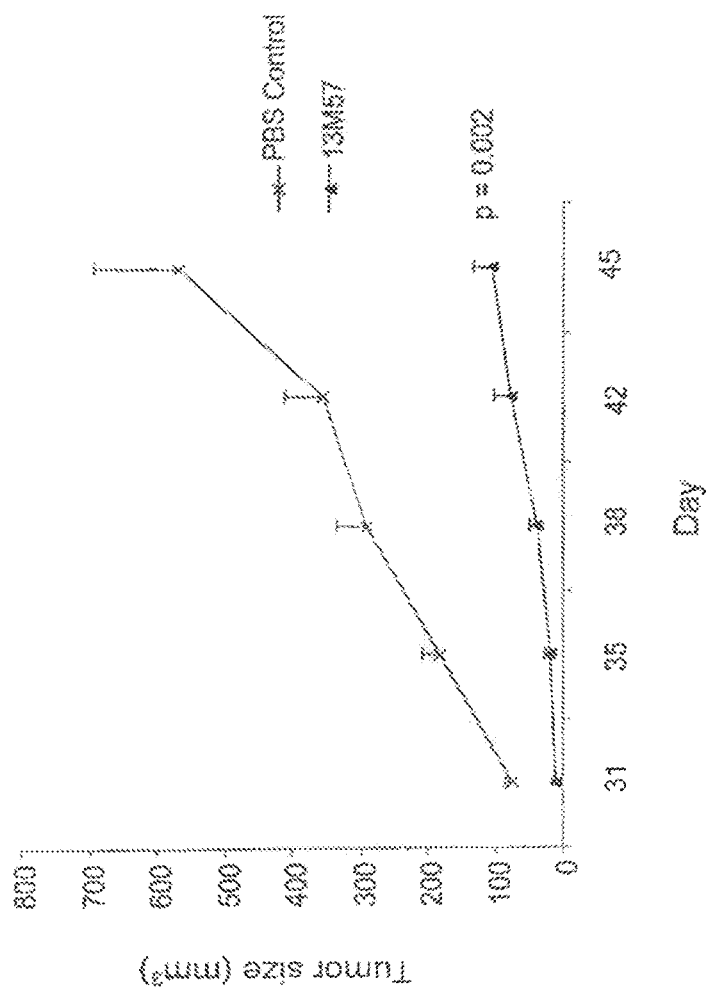
Figure 6B:
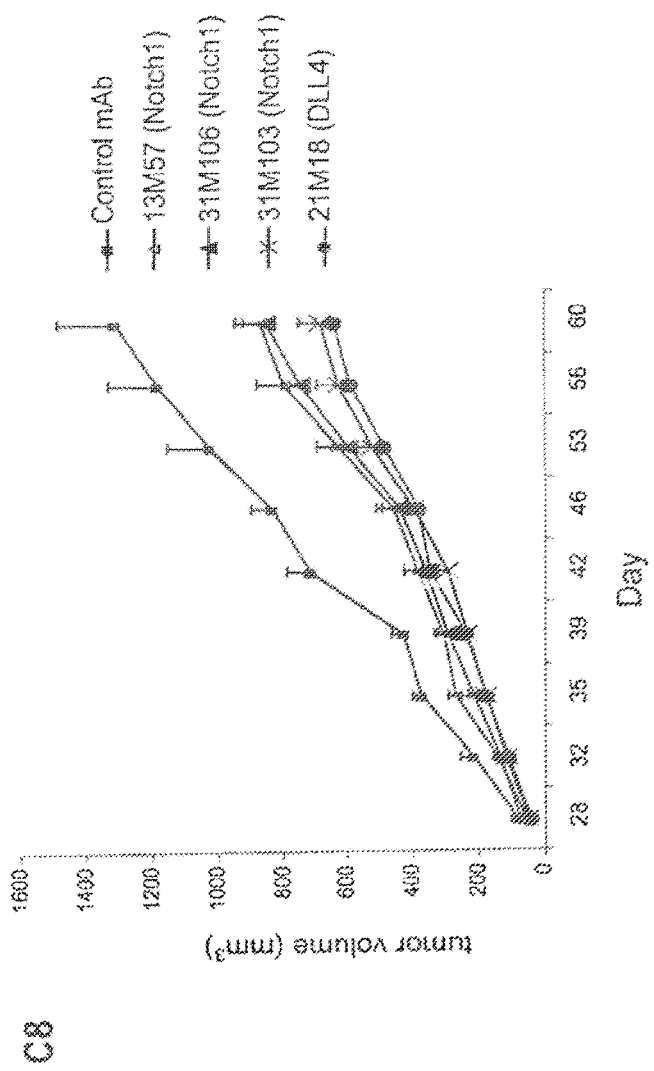

FIGS. 6A and 6B: Effect of NOTCH1 Monoclonal Antibodies on Colon Tumor Cells In Vivo. NOD/SCID mice injected with OMP-C9 (A) or OMP-C8 (B) colon tumor cells were treated with PBS or anti-NOTCH1 13M57 antibodies (A) or 13M57, 31M106, and 31M103 (B) three days after cell injection, and the growth of tumor cells was determine twice a week. Total tumor volume was significantly reduced in animals treated with anti-NOTCH antibodies compared to PBS injected controls in both tumor models. Antibodies against EGF4 and EGF13 were all equally effective against C8 colon tumors (B).

Figure 7A:
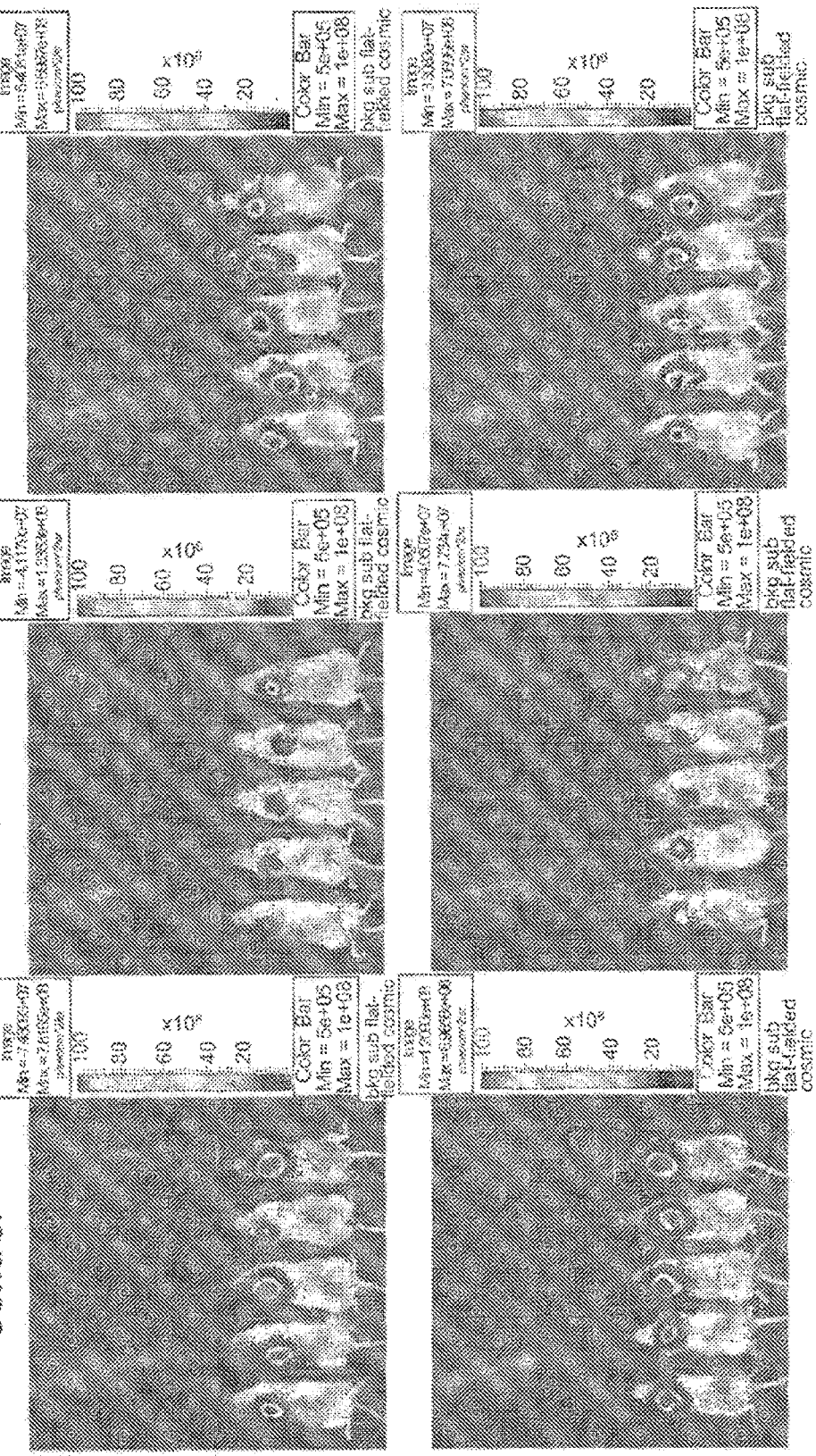
Figure 7B:
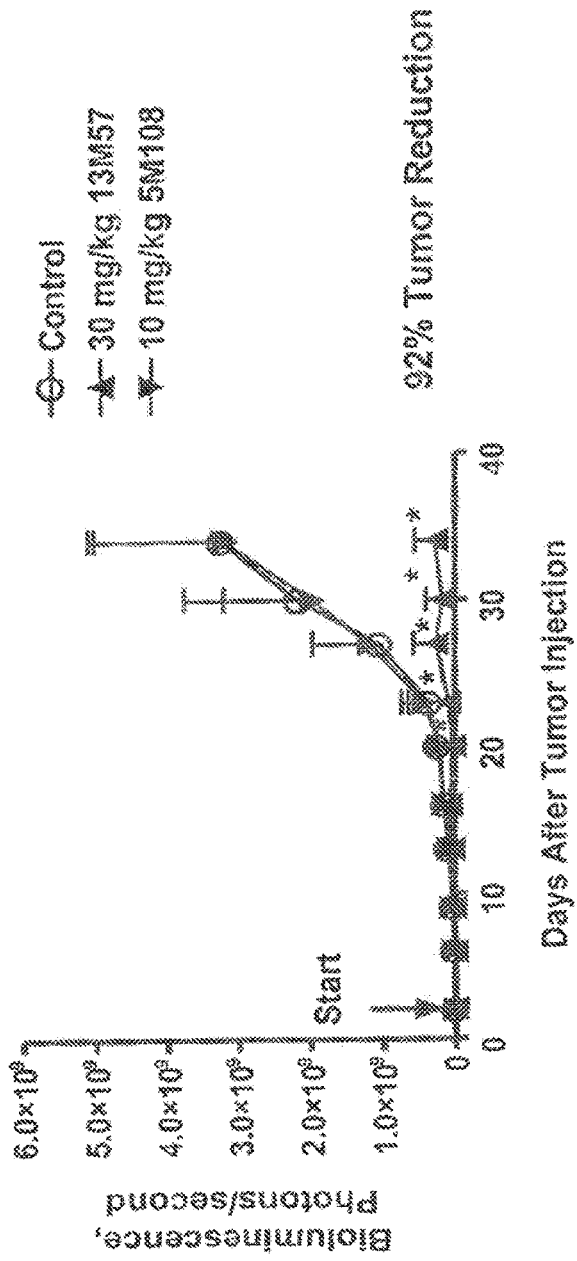

FIGS. 7A and 7B: Effect of NOTCH1 Monoclonal Antibody 13M57 on PE-13 Tumor Cells Expressing Luciferase. NOD/SCID mice injected with PE-13 tumor cells were treated with anti-NOTCH1 antibodies, control 5M108 control antibodies, or PBS. A scale of luciferase activity is provided at the right of each picture with upper dark indicating the highest activity (100 or higher×$10^6$) and lower levels (<30×$10^6$) indicating low luciferase signal. (A) Animals treated with PBS or 5M108 controls antibodies have tumors detected in the upper dark region of the scale. In contrast, tumors in animals treated with anti-Notch antibodies show luciferase activity mainly in the lower region of the scale. (B) Quantification of luciferase signal shows total tumor volume was significantly reduced ($p=0.04$) in animals treated with anti-NOTCH1 antibodies 13M57 compared to PBS and 5M108 injected controls.

Figure 8:
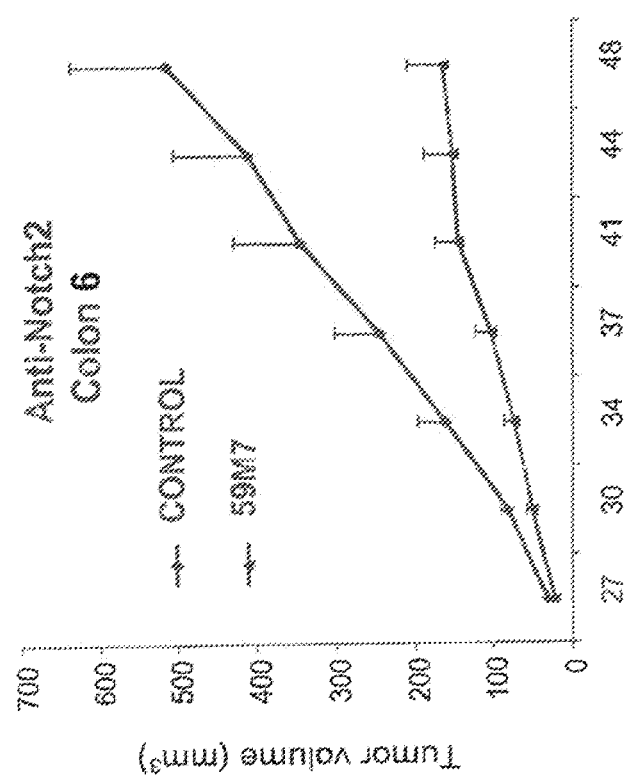

FIG. 8: Effect of NOTCH2 Monoclonal Antibody 59M07 on Colon Tumor Growth. NOD/SOD mice injected with C6 colon tumor cells were treated with anti-NOTCH2 antibodies or PBS vehicle as a control. Animals treated with anti-NOTCH2 59M07 (triangles) showed significant reduction in tumor growth over 48 days compared to control treated animals (diamonds).

FIGS. 9A and 9B: Effect of anti-NOTCH1 Antibody 13M57 and Chemotherapy Combination Therapy on Breast Tumor Reoccurrence. (A) Graph of the response of UM-PE13 tumors to four different treatment regimes: Group 1: paclitaxel followed by PBS (squares); Group 2: paclitaxel followed by 13M57 (inverted triangles); Group 3 paclitaxel+13M57 followed by PBS (circles); and Group 4: paclitaxel+13M57 followed by 13M57 (diamonds). Initial treatments commenced when the average tumor volume per group (n=10) was 130 mm$^3$ (Arrow: Start Paclitaxel). Paclitaxel (or Paclitaxel+13M57) treatments were stopped at day 52 after the tumors had regressed and were undetectable (Arrow: Stop Paclitaxel). (B) Both the individual animal tumor volumes (dots) and average (lines) tumor volumes for each treatment group are graphed. Concurrent combination treatment followed by continual treatment with anti-NOTCH1 13M57 antibodies (far right) had the greatest effect on inhibiting tumor recurrence following the cessation of paclitaxel treatment.

Figure 10A:
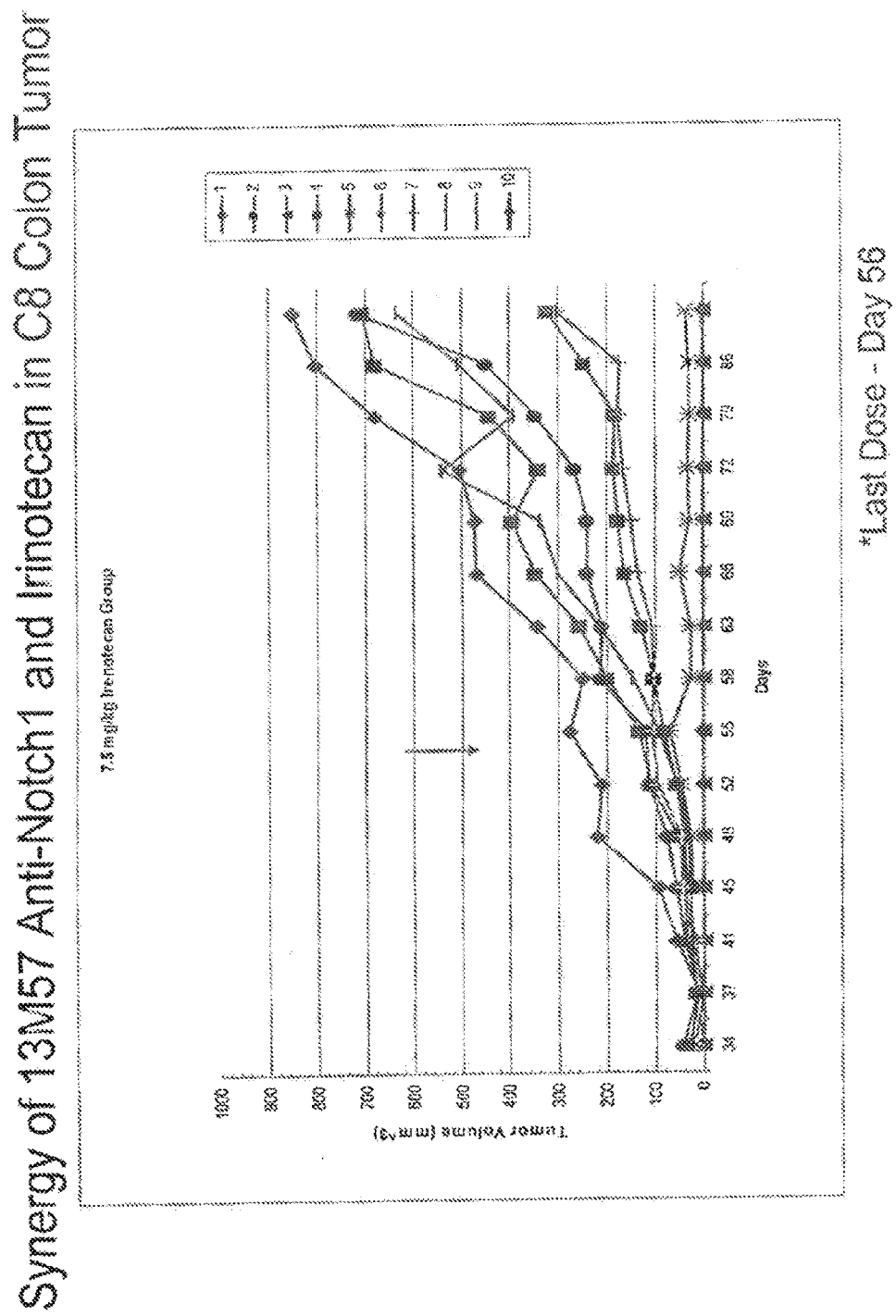
Figure 10B:
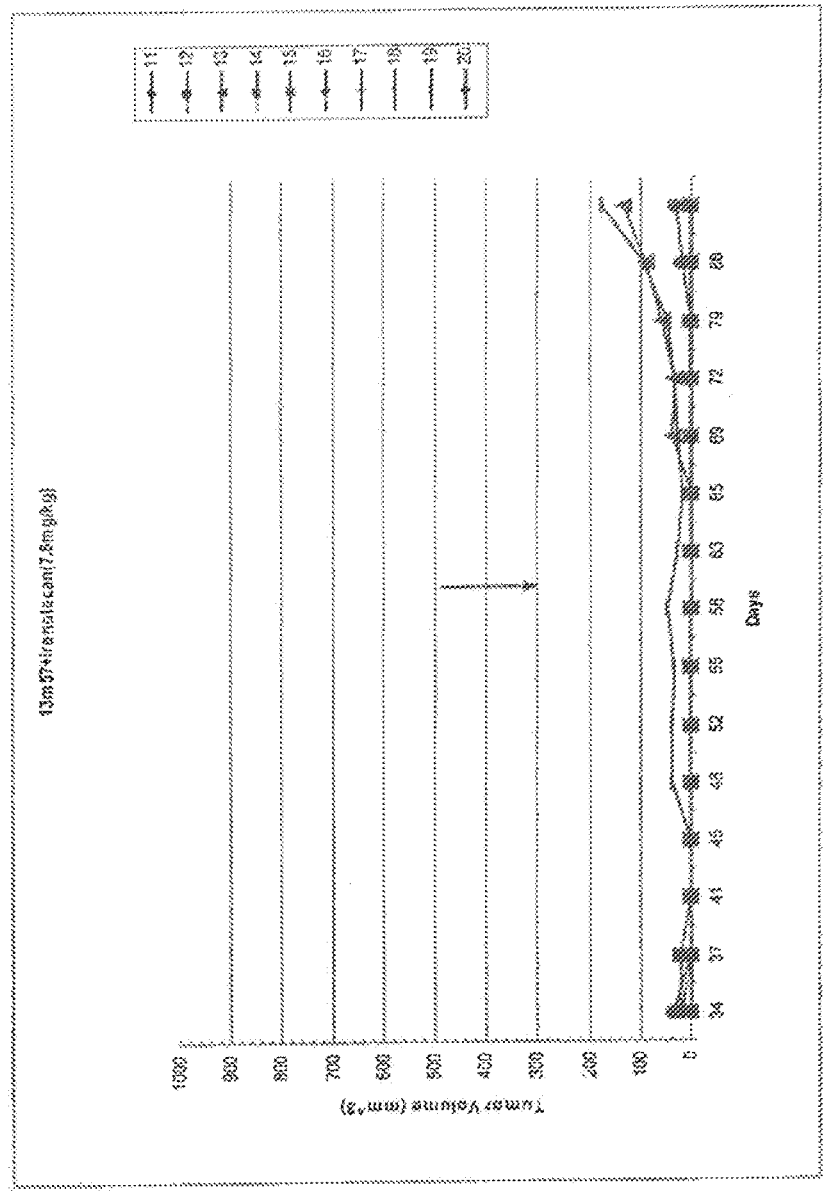

FIGS. 10A and 10B: Effect of anti-NOTCH1 Antibody 13M57 and Chemotherapy Combination Therapy on Colon Tumor Growth. (A) A graph of C8 colon tumor volume during and after twice weekly treatment with 7.5 mg/kg irinotecan, or with 10 mg/kg of the anti-NOTCH1 antibody 13M57 plus 7.5 mg/kg irinotecan (n=10). The tumor volume of ten animals was assessed twice per week. The last treatment dose was given on day 56 (*). (B) A graph of C8 colon tumor volume during and after twice weekly treatment with 7.5 mg/kg irinotecan plus 10 mg/kg 13M57. The tumor volume of ten animals was assessed twice per week. The last treatment dose was given on day 56 (*). Concurrent combination treatment of irinotecan and 13M57 prevented colon tumor growth and also maintained tumor cells in this non-proliferative state for up to thirty days post-treatment.

FIG. 11: Effect of anti-NOTCH1 Antibody 13M57 and Chemotherapy Combination Therapy on Established Colon Tumor Growth. A graph shows C8 colon tumor volume over the course of treatment with either oxaliplatin (triangles), 10 mg/kg 13M57 (diamonds), a combination of oxaliplatin and 13M57 (circles), or a control antibody (squares). Treatment with either anti-NOTCH1 13M57 or oxaliplatin significantly reduced tumor growth ($p=0.04$ vs. control), but combination treatment further reduced growth compared to treatment with either agent alone ($p=0.03$ vs. single agent).

Figure 12A:
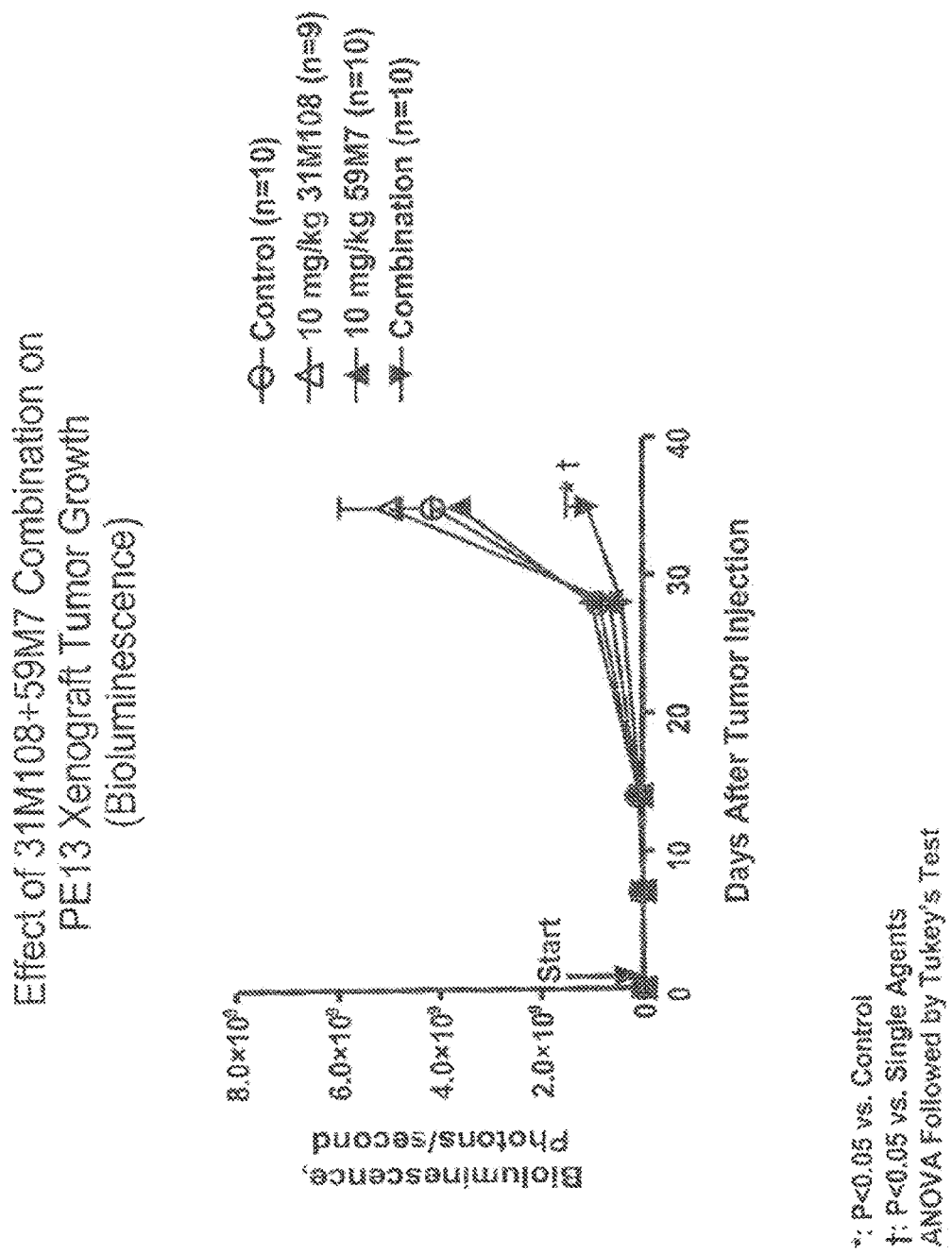

FIGS. 12A and 12B: Effect of NOTCH1 and NOTCH2 Antibody Combination Therapy on Breast Tumor Growth. (A) A graph of bioluminescence imaging of animals treated either with 10 mg/kg anti-NOTCH1 31M108 (open triangles), 10 mg/kg 59M07 anti-NOTCH2 (filled triangles), a combination of anti-NOTCH1 and NOTCH2 antibodies (filled inverted triangles), or a control antibody (open circles). Animals were imaged twice weekly. Combination treatment with anti-NOTCH1 and NOTCH2 antibodies significantly reduced growth of luciferase expressing PE13 tumor cells. (B) A graph of total tumor volume of animals treated either with 10 mg/kg anti-NOTCH1 31M108 (open triangles), 10 mg/kg 59M07 anti-NOTCH2 (filled triangles), a combination of anti-NOTCH1 and NOTCH2 antibodies (filled inverted triangles), or a control antibody (open circles). Tumor volume was assessed twice per week. Animals treated with 31M108 antibodies showed a significant reduction in total tumor volume compared to control treated animals ($p<0.05$). A further reduction of breast tumor growth was observed in animals treated with a combination of anti-NOTCH1 and anti-NOTCH2 antibodies as compared to treatment with either antibody alone (p<0.05).

DETAILED DESCRIPTION OF THE INVENTION

Definitions

The term "antagonist" includes any molecule that partially or fully blocks, inhibits, or neutralizes a biological activity of the Notch pathway. Suitable antagonist molecules specifically include antagonist antibodies or antibody fragments, fragments or amino acid sequence variants of native Notch receptors. The term "antagonist" is used herein to include any molecule that partially or fully blocks, inhibits, or neutralizes the expression of or the biological activity of a cancer stem cell marker disclosed herein and such biological activity includes, but is not limited to, inhibition of tumor growth.

The term "antibody" is used to mean an immunoglobulin molecule that recognizes and specifically binds to a target, such as a protein, polypeptide, peptide, carbohydrate, polynucleotide, lipid, or combinations of the foregoing etc., through at least one antigen recognition site within the variable region of the immunoglobulin molecule. As used herein, the term encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, fusion proteins comprising an antibody portion, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha., delta, epsilon, gamma, and mu, respectively. The different classes of immunoglobulins have different and well known subunit structures and three-dimensional configurations. Antibodies can be naked or conjugated to other molecules such as toxins, radioisotopes, etc.

As used herein, the term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

An "Fv antibody" refers to the minimal antibody fragment that contains a complete antigen-recognition and -binding site either as two-chains, in which one heavy and one light chain variable domain form a non-covalent dimer, or as a single-chain (scFv), in which one heavy and one light chain variable domain are covalently linked by a flexible peptide linker so that the two chains associate in a similar dimeric structure. In this configuration the complementary determining regions (CDRs) of each variable domain interact to define the antigen-binding specificity of the Fv dimer. Alternatively a single variable domain (or half of an Fv) can be used to recognize and bind antigen, although generally with lower affinity.

A "monoclonal antibody" as used herein refers to homogenous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

As used herein, the term "humanized antibody" refers to forms of non-human (e.g. murine) antibodies that are specific immunoglobulin chains, chimeric immunoglobulins, or fragments thereof that contain minimal non-human sequences. Typically, humanized antibodies are human immunoglobulins in which residues from the complementary determining region (CDR) are replaced by residues from the CDR of a non-human species (e.g. mouse, rat, rabbit, hamster, etc.) that have the desired specificity, affinity, and capability. In some instances, the Fv framework region (FR) residues of a human immunoglobulin are replaced with the corresponding residues in an antibody from a non-human species that has the desired specificity, affinity, and capability. The humanized antibody can be further modified by the substitution of additional residue either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fe), typically that of a human immunoglobulin. Examples of methods used to generate humanized antibodies are described in U.S. Pat. No. 5,225,539, herein incorporated by reference.

The term "human antibody" as used herein means an antibody produced by a human or an antibody having an amino acid sequence corresponding to an antibody produced by a human made using any of the techniques known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

"Hybrid antibodies" are immunoglobulin molecules in which pairs of heavy and light chains from antibodies with different antigenic determinant regions are assembled together so that two different epitopes or two different antigens can be recognized and bound by the resulting tetramer.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals mouse, rat, rabbit, etc.) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

Competition between antibodies is determined by an assay in which the if immunoglobulin under test inhibits specific binding of a reference antibody to a common antigen. Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242-253 (1983)); solid phase direct biotin-avidin EIA (see. Kirkland et al., J. Immunol, 137:3614-3619 (1986)); solid phase direct labeled assay, solid phase direct labeled sandwich assay (see Harlow and Lane, "Antibodies, A Laboratory Manual." Cold Spring Harbor Press (1988)); solid phase direct label RIA using 1-125 label (see Morel et al., Molec. Immunol. 25(1):7-15 (1988)); solid phase direct biotin-avidin EIA (Cheung et al., Virology 176; 546-552 (1990)); and direct labeled RIA (Moldenhauer et al., Scand. J. Immunol. 32:77-82 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present excess, it will inhibit specific binding of a reference antibody to a common antigen by at least 50 or 75%.

That an antibody "selectively binds" or "specifically binds" to an epitope or receptor means that the antibody reacts or associates more frequently, more rapidly, with greater duration, with greater affinity, or with some combination of the above to the epitope or receptor than with alternative substances, including unrelated proteins. "Selectively binds" or "specifically binds" means, for instance, that an antibody binds to a protein with a KD of at least about 0.1 mM, more usually at least about 1 uM. "Selectively binds" or "specifically binds" means at times that an antibody binds to a protein at times with a KD of at least about 0.1 mM or better, and at other times at least about 0.01 uM or better. Because of the sequence identity between homologous proteins in different species, specific binding can include an antibody that recognizes a cancer stem cell marker in more than one species.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

The terms "isolated" or "purified" refer to material that is substantially or essentially free from components that normally accompany it in its native state. Purity and homogeneity are typically determined using analytical chemistry techniques such as polyacrylamide gel electrophoresis or high performance liquid chromatography. A protein (e.g. an antibody) or nucleic acid that is the predominant species present in a preparation is substantially purified. In particular, an isolated nucleic acid is separated from open reading frames that naturally flank the gene and encode proteins other than protein encoded by the gene. An isolated antibody is separated from other non-immunoglobulin proteins and from other immunoglobulin proteins with different antigen binding specificity. It can also mean that the nucleic acid or protein is at least 85% pure, at least 95% pure, and in some embodiments, at least 99% pure.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

The terms "proliferative disorder" and "proliferative disease" refer to disorders associated with abnormal cell proliferation such as cancer.

"Tumor" and "neoplasm" as used herein refer to any mass of tissue that result from excessive cell growth or proliferation, either benign (noncancerous) or malignant (cancerous) including pre-cancerous lesions.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The terms "cancer stem cell", "tumor stem cell", or "solid tumor stem cell" are used interchangeably herein and refer to a population of cells from a solid tumor that: (1) have extensive proliferative capacity; 2) are capable of asymmetric cell division to generate one or more kinds of differentiated progeny with reduced proliferative or developmental potential; and (3) are capable of symmetric cell divisions for self-renewal or self-maintenance. These properties of "cancer stem cells", "tumor stem cells" or "solid tumor stem cells" confer on those cancer stem cells the ability to form palpable tumors upon serial transplantation into an immunocompromised mouse compared to the majority of tumor cells that fail to form tumors. Cancer stem cells undergo self-renewal versus differentiation in a chaotic manner to form tumors with abnormal cell types that can change over time as mutations occur. The solid tumor stem cells of the present invention differ from the "cancer stem line" provided by U.S. Pat. No. 6,004,528. In that patent, the "cancer stem line" is defined as a slow growing progenitor cell type that itself has few mutations but which undergoes symmetric rather than asymmetric cell divisions as a result of tumorigenic changes that occur in the cell's environment. This "cancer stem line" hypothesis thus proposes that highly mutated, rapidly proliferating tumor cells arise largely as a result of an abnormal environment, which causes relatively normal stem cells to accumulate and then undergo mutations that cause them to become tumor cells. U.S. Pat. No. 6,004,528 proposes that such a model can be used to enhance the diagnosis of cancer. The solid tumor stem cell model is fundamentally different than the "cancer stem line" model and as a result exhibits utilities not offered by the "cancer stem line" model. First, solid tumor stem cells are not "mutationally spared". The "mutationally spared cancer stem line" described by U.S. Pat. No. 6,004,528 can be considered a pre-cancerous lesion, while the solid tumor stem cells described by this invention are cancer cells that themselves contain the mutations that are responsible for tumorigenesis. That is, the solid tumor stem cells ("cancer stein cells") of the invention would be included among the highly mutated cells that are distinguished from the "cancer stem line" in U.S. Pat. No. 6,004,528. Second, the genetic mutations that lead to cancer can be largely intrinsic within the solid tumor stem cells as well as being environmental. The solid tumor stem cell model predicts that isolated solid tumor stem cells can give rise to additional tumors upon transplantation (thus explaining metastasis) while the "cancer stem line" model would predict that transplanted "cancer stem line" cells would not be able to give rise to a new tumor, since it was their abnormal environment that was tumorigenic. Indeed, the ability to transplant dissociated, and phenotypically isolated human solid tumor stem cells to mice (into an environment that is very different from the normal tumor environment), where they still form new tumors, distinguishes the present invention from the "cancer stem line" model. Third, solid tumor stem cells likely divide both symmetrically and asymmetrically, such that symmetric cell division is not an obligate property. Fourth, solid tumor stem cells can divide rapidly or slowly, depending on many variables, such that a slow proliferation rate is not a defining characteristic.

The terms "cancer cell", "tumor cell" and grammatical equivalents refer to the total population of cells derived from a tumor including both non-tumorigenic cells, which comprise the bulk of the tumor cell population, and tumorigenic stem cells (cancer stem cells).

As used herein "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor.

As used herein, the terms "stem cell cancer marker(s)", "cancer stem cell marker(s)", "tumor stem cell marker(s)", or "solid tumor stem cell marker(s)" refer to a gene or genes or a protein, polypeptide, or peptide expressed by the gene or genes whose expression level, alone or in combination with other genes, is correlated with the presence of tumorigenic cancer cells compared to non-tumorigenic cells. The correlation can relate to either an increased or decreased expression of the gene (e.g. increased or decreased levels of mRNA or the peptide encoded by the gene).

The terms "cancer stein cell gene signature", "tumor stem cell gene signature" or "cancer stem cell signature" are used interchangeably herein to refer to gene signatures comprising genes differentially expressed in cancer stem cells compared to other cells or population of cells, for example normal breast epithelial tissue. In some embodiments the cancer stem cell gene signatures comprise genes differentially expressed in cancer stem cells versus normal breast epithelium by a fold change, for example by 2 fold reduced and/or elevated expression, and further limited by using a statistical analysis such as, for example, by the P value of a t-test across multiple samples. In another embodiment, the genes differentially expressed in cancer stem cells are divided into cancer stem cell gene signatures based on the correlation of their expression with a chosen gene in combination with their fold or percentage expression change. Cancer stem cell signatures are predictive both retrospectively and prospectively of an aspect of clinical variability, including but not limited to metastasis and death.

The term "genetic test" as used herein refers to procedures whereby the genetic make-up of a patient or a patient tumor sample is analyzed. The analysis can include detection of DNA, RNA, chromosomes, proteins or metabolites to detect heritable or somatic disease-related genotypes or karyotypes for clinical purposes.

As used herein, the terms "biopsy" or "biopsy tissue" refer to a sample of tissue or fluid that is removed from a subject for the purpose of determining if the sample contains cancerous tissue. In some embodiments, biopsy tissue or fluid is obtained because a subject is suspected of having cancer. The biopsy tissue or fluid is then examined for the presence or absence of cancer.

As used herein an "acceptable pharmaceutical carrier" refers to any material that, when combined with an active ingredient of a pharmaceutical composition such as an antibody, allows the antibody, for example, to retain its biological activity. In addition, an "acceptable pharmaceutical carrier" does not trigger an immune response in a recipient subject. Examples include, but are not limited to, any of the standard pharmaceutical carriers such as a phosphate buffered saline solution, water, and various oil/water emulsions. Some diluents for aerosol or parenteral administration are phosphate buffered saline or normal (0.9%) saline.

The term "therapeutically effective amount" refers to an amount of an antibody, polypeptide, polynucleotide, small organic molecule, or other drug effective to "treat" a disease or disorder in a subject or mammal. In the case of cancer, the therapeutically effective amount of the drug can reduce the number of cancer cells; reduce the tumor size; inhibit or stop cancer cell infiltration into peripheral organs; inhibit and stop tumor metastasis; inhibit and stop tumor growth; relieve to some extent one or more of the symptoms associated with the cancer, or a combination of such effects on cancer cells. To the extent the drug prevents growth and/or kills existing cancer cells, it can be referred to as cytostatic and/or cytotoxic.

As used herein, "providing a diagnosis" or "diagnostic information" refers to any information that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis refers to providing any type of diagnostic information, including, but not limited to, whether a subject is likely to have a condition (such as a tumor), information related to the nature or classification of a tumor as for example a high risk tumor or a low risk tumor, information related to prognosis and/or information useful in selecting an appropriate treatment. Selection of treatment can include the choice of a particular chemotherapeutic agent or other treatment modality such as surgery or radiation or a choice about whether to withhold or deliver therapy.

As used herein, the terms "providing a prognosis", "prognostic information", or "predictive information" refer to providing information regarding the impact of the presence of cancer (e.g., as determined by the diagnostic methods of the present invention) on a subject's future health (e.g., expected morbidity or mortality, the likelihood of getting cancer, and the risk of metastasis).

Terms such as "treating" or "treatment" or "to treat" or "alleviating" or "to alleviate" refer to both 1) therapeutic measures that cure, slow down, lessen symptoms of and/or halt progression of a diagnosed pathologic condition or disorder and 2) prophylactic or preventative measures that prevent or slow the development of a targeted pathologic condition or disorder. Thus those in need of treatment include those already with the disorder; those prone to have the disorder; and those in whom the disorder is to lie prevented. A subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including the spread of cancer into soft tissue and bone: inhibition of or an absence of tumor metastasis; inhibition or an absence of tumor growth; relief of one or more symptoms associated with the specific cancer; reduced morbidity and mortality; and improvement in quality of life.

As used herein, the terms "polynucleotide" or "nucleic acid" refer to a polymer composed of a multiplicity of nucleotide units (ribonucleotide or deoxyribonucleotide or related structural variants) linked via phosphodiester bonds, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl 2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl guanine, 2-methyladenine, 2-methylguanine, 3-methylcytosine, 5-methylcytosine, N6-methyladenine, 7-methylguanine, 5-methylaminomethyluracil, 5-methoxyaminomethyl 2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2 thiouracil, 2-thiouracil, 4-thiouracil, 5-methyluracil, N-uracil-5-oxyacetic acid methylester, uracil-5-oxyacetic acid, pseudouracil, queosine, 2-thiocytosine and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns can contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. In addition to containing introns, genomic forms of a gene can also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region can contain regulatory sequences such as promoters and enhancers that control or influence the transcription of the gene. The 3° flanking region can contain sequences that direct the termination of transcription, post transcriptional cleavage and polyadenylation.

The term "recombinant" when used with reference to a cell, nucleic acid, protein or vector indicates that the cell, nucleic acid, protein or vector has been modified by the introduction of a heterologous nucleic acid or protein, the alteration of a native nucleic acid or protein, or that the cell is derived from a cell so modified. Thus, e.g., recombinant cells express genes that are not found within the native (non-recombinant) form of the cell or express native genes that are overexpressed or otherwise abnormally expressed such as, for example, expressed as non-naturally occurring fragments or splice variants. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention, it is understood that once a recombinant nucleic acid is made and introduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "vector" is used in reference to nucleic acid molecules that, transfer DNA segment(s) from one cell to another. The term "vehicle" is sometimes used interchangeably with "vector." Vectors are often derived from plasmids, bacteriophages, or plant or animal viruses.

"Ligation" refers to the process of forming phosphodiester bonds between two double stranded nucleic acid fragments. Unless otherwise provided, ligation can be accomplished using known buffers and conditions with 10 units to T4 DNA ligase ("ligase") per 0.5 ug of approximately equimolar amounts of the DNA fragments to be ligated. Ligation of nucleic acid can serve to link two proteins together in-frame to produce a single protein, or fusion protein.

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Upregulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

The terms "polypeptide," "peptide," "protein", and "protein fragment" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

"Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, CCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. It is recognized that in certain contexts each codon in a nucleic acid (except AUG, which is ordinarily the only codon for methionine, and TOG, which is ordinarily the only codon for tryptophan) can be modified to yield a functionally identical molecule. Accordingly, silent variations of a nucleic acid which encodes a polypeptide is implicit in a described sequence with respect to the expression product, but not with respect to actual probe sequences. As to amino acid sequences, it will be recognized that individual substitutions, deletions or additions to a nucleic acid, peptide, polypeptide, or protein sequence which alters, adds or deletes a single amino acid or a small percentage of amino acids in the encoded sequence is a "conservatively modified variant" including where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The term "epitope tagged" as used herein refers to a chimeric polypeptide comprising a cancer stem cell marker protein, or a domain sequence or portion thereof, fused to an "epitope tag". The epitope tag polypeptide comprises enough amino acid residues to provide an epitope for recognition by an antibody, yet is short enough such that it does not interfere with the activity of the cancer stem cell marker protein. Suitable epitope tags generally have at least six amino acid residues, usually between about 8 to about 50 amino acid residues, and at times between about 10 to about 20 residues. Commonly used epitope tags include Fc, HA, His, and FLAG tags.

Certain Embodiments of the Present Invention

The present invention provides compositions and methods for studying, diagnosing, characterizing, and treating cancer. In particular, the present invention provides antagonists against solid tumor stem cell markers and methods of using these antagonists to inhibit tumor growth and treat cancer in human patients. Several antagonists include antibodies that specifically recognize solid tumor stem cell marker proteins.

The present invention further identifies molecules (e.g. antibodies) that specifically bind to a non-ligand binding region of the extracellular domain of a human NOTCH receptor and inhibit tumor growth in vivo. The ligand binding region of Notch, which is necessary and sufficient for ligand binding, has been identified as FOE repeats 11 and 12, suggesting this region of the Notch receptor is important in Notch signaling and tumorigenesis (Rebay et al., 1991, Cell 67:687; Lei et al., 2003, Dev. 130:6411; Hambleton et al., 2004, Structure 12:2173). Unexpectedly and for the first time, antibodies that bind outside the ligand binding domain of the extracellular domain of human Notch receptor were found to inhibit tumor cell growth in vivo. One such antibody to an epitope within EGF repeat 4 of NOTCH1 inhibited tumor cell growth in an animal model. These results suggest that antibodies that bind outside the ligand binding domain of the extracellular domain of one or more of the human Notch receptors—NOTCH1, NOTCH2, NOTCH3, and NOTCH4—have value as potential cancer therapeutics.

In certain embodiments, the present invention provides an antibody that specifically binds to a non-ligand binding region of the extracellular domain of a human NOTCH receptor and inhibits growth of tumor cells. In certain embodiments, the antibody binds to a non-ligand binding region of the extracellular domain of NOTCH1 receptor. In certain embodiments, the antibody that specifically binds to a non-ligand binding region of the extracellular domain of a human NOTCH receptor and inhibits growth of tumor cells specifically binds to a non-ligand binding region of the extracellular domain of at least two Notch receptor family members.

In certain embodiments, the antibody that specifically binds to a non-ligand binding region of the extracellular domain of a human NOTCH receptor and inhibits growth of tumor cells is a monoclonal antibody. In certain embodiments, the antibody that specifically binds to a non-ligand binding region of the extracellular domain of a human NOTCH receptor and inhibits growth of tumor cells is a chimeric antibody. In certain embodiments, the antibody that specifically binds to a non-ligand binding region of the extracellular domain of a human NOTCH receptor and inhibits growth of tumor cells is a humanized antibody. In certain embodiments, the antibody that specifically binds to a non-ligand binding region of the extracellular domain of a human NOTCH receptor and inhibits growth of tumor cells is a human antibody. In certain embodiments, the present invention provides a hybridoma producing an antibody that specifically binds to a non-ligand binding region of the extracellular domain of a human NOTCH receptor and inhibits growth of tumor cells.

In certain embodiments the present invention provides an antibody that specifically binds to a non-ligand binding region comprising EGF repeats 1-10 of the extracellular domain of a human NOTCH receptor and inhibits growth of tumor cells. In certain embodiments the present invention provides an antibody that specifically binds to a non-ligand binding region comprising EGF repeats 13-36 of the extracellular domain of a human NOTCH receptor and inhibits growth of tumor cells. Certain embodiments provide an antibody that specifically binds to a non-ligand binding region comprising EGF repeats 4 of the extracellular domain of a human NOTCH receptor and inhibits growth of tumor cells. Certain embodiments provide an antibody that specifically binds to a non-ligand binding region comprising EGF repeats 13 of the extracellular domain of a human NOTCH receptor and inhibits growth of tumor cells.

In certain embodiments, the present invention provides an isolated polypeptide that specifically binds to a non-ligand binding region of an extracellular domain of a human NOTCH receptor comprising: (a) a heavy chain variable region having CDR sequences set forth in SEQ. ID NOS: 12, 13, and 14; and (b) a light chain variable region having CDR sequences set forth in SEQ ID NOS: 15, 16, and 17. In certain embodiments, the isolated polypeptide that specifically binds to a non-ligand binding region of an extracellular domain of a human NOTCH receptor comprises: (a) heavy chains set forth in SEQ. ID NOS: 4 and 5; and (b) light chains set forth in SEQ ID NOS: 6 and 7.

In certain embodiments the present invention provides a method of treating cancer to a subject in need thereof comprising administering a therapeutically effective amount of an antibody that specifically binds to a non-ligand binding region of the extracellular domain of a human NOTCH receptor protein to the subject and inhibits growth of tumor cells in the subject. In certain embodiments, the method of treating cancer in a subject in need thereof comprises administering a therapeutically effective amount of an antibody to the subject that specifically binds to a non-ligand binding region of the extracellular domain of NOTCH1 receptor and inhibits growth of tumor cells. In certain embodiments, the method of treating cancer comprises administering a therapeutically effective amount of an antibody that specifically binds to at least two Notch receptor family members and inhibits growth of tumor cells.

In certain embodiments, the method of treating cancer comprises administering a therapeutically effective amount of a monoclonal antibody that specifically binds to a non-ligand binding region of the extracellular domain of a human NOTCH receptor and inhibits growth of tumor cells. In certain embodiments, the method of treating cancer comprises administering a therapeutically effective amount of a chimeric antibody that specifically binds to a non-ligand binding region of the extracellular domain of a human NOTCH receptor and inhibits growth of tumor cells. In certain embodiments, the method of treating cancer comprises administering a therapeutically effective amount of a humanized antibody that specifically binds to a non-ligand binding region of the extracellular domain of a human NOTCH receptor and inhibits growth of tumor cells. In certain embodiments, the method of treating cancer comprises administering a therapeutically effective amount of a human antibody that specifically binds to a non-ligand binding region of the extracellular domain of a human NOTCH receptor and inhibits growth of tumor cells.

In certain embodiments, the method of treating cancer comprises administering a therapeutically effective amount of an antibody that specifically binds to a non-ligand binding region of the extracellular domain of a human NOTCH receptor comprising EGF repeats 1-10 and inhibits growth of tumor cells. In certain embodiments, the method of treating cancer comprises administering a therapeutically effective amount of an antibody that specifically binds to a non-ligand binding region of the extracellular domain of a human NOTCH receptor comprising EGF repeats 13-36 and inhibits growth of tumor cells. In certain embodiments, the method of treating cancer comprises administering a therapeutically effective amount of an antibody that specifically binds to a non-ligand binding region of the extracellular domain of a human NOTCH receptor comprising EGF repeats 4 and inhibits growth of tumor cells. In certain embodiments, the method of treating cancer comprises administering a therapeutically effective amount of an antibody that specifically binds to a non-ligand binding region of the extracellular domain of a human NOTCH receptor comprising EGF repeats 4 and inhibits growth of tumor cells.

In certain embodiments, the method of treating cancer comprises administering a therapeutically effective amount of an isolated polypeptide that specifically binds to a non-ligand binding region of the extracellular domain of a human NOTCH receptor comprising: (a) a heavy chain variable region having CDR sequences set forth in SEQ ID NOS: 12, 13, and 14; and (b) a light chain variable region having CDR sequences set forth in SEQ ID NOS: 15, 16, and 17 and inhibits growth of tumor cells. In certain embodiments, the method of treating cancer comprises administering a therapeutically effective amount of an antibody that specifically binds to a non-ligand binding region of the extracellular domain of a human NOTCH receptor comprising (a) heavy chains set forth in SEQ ID NOS: 4 and 5; and (b) light chains set forth in SEQ ID NOS: 6 and 7.

In certain embodiments, the method of treating cancer comprises administering a therapeutically effective amount of an antibody conjugated to a cytotoxic moiety that specifically binds to a non-ligand binding region of the extracellular domain of a human NOTCH receptor and inhibits growth of tumor cells, in certain embodiments, the method of treating cancer comprises administering a therapeutically effective amount of an antibody that specifically binds to a non-ligand binding region of the extracellular domain of a human NOTCH receptor and inhibits growth of tumor cells in combination with radiation therapy. In certain embodiments, the method of treating cancer comprises administering a therapeutically effective amount of an antibody that specifically binds to a non-ligand binding region of the extracellular domain of a human NOTCH receptor and inhibits growth of tumor cells in combination with chemotherapy. In certain embodiments, the method of treating cancer comprises administering a therapeutically effective amount of an antibody that specifically binds to a non-ligand binding region of the extracellular domain of a human NOTCH receptor and inhibits growth of tumor cells that are from a breast tumor, colorectal tumor, lung tumor, pancreatic tumor, prostate tumor, or a head and neck tumor.

In certain embodiments, the method of treating cancer comprises identifying patients using a genetic test for treatment with the antibody that specifically binds to a non-ligand binding region of the extracellular domain of a human NOTCH receptor; and administering a therapeutically effective amount of an antibody that specifically binds to a non-ligand binding region of the extracellular domain of a human NOTCH receptor and inhibits growth of tumor cells. In certain embodiments, the method of treating cancer comprises identify patients for treatment with the antibody that specifically binds to a non-ligand binding region of the extracellular domain of a human NOTCH receptor using a genetic test that detects a cancer stem cell signature; and administering a therapeutically effective amount of an antibody that specifically binds to a non-ligand binding region of the extracellular domain of a human NOTCH receptor and inhibits growth of tumor cells.

In certain embodiments, the present invention provides a method of identifying a molecule that binds to a non-ligand binding region of an extracellular domain of a human NOTCH receptor and inhibits growth of tumor cells, the method comprising: i) incubating the molecule with the non-ligand binding domain of the extracellular domain of a human Notch receptor; ii) determining if the molecule binds to the non-ligand binding region of the extracellular domain of the human Notch receptor; and iii) determining if the molecule inhibits growth of tumor cells. In certain embodiments, the invention provides a method of identifying a molecule that binds to a non-ligand binding region of an extracellular domain of a human NOTCH receptor and inhibits growth of tumor cells, the method comprising: i) incubating the molecule with the non-ligand binding domain of the extracellular domain of a human Notch receptor comprising EGF repeats 1-10; ii) determining if the molecule binds to the non-ligand binding region of the extracellular domain of the human Notch receptor comprising EGF repeats 1-10; and iii) determining if the molecule inhibits growth of tumor cells. In certain embodiments, the invention provides a method of identifying a molecule that binds to a non-ligand binding region of an extracellular domain of a human NOTCH receptor and inhibits growth of tumor cells, the method comprising: i) incubating the molecule with the non-ligand binding domain of the extracellular domain of a human Notch receptor comprising EGF repeats 13-36; ii) determining if the molecule binds to the non-ligand binding region of the extracellular domain of the human Notch receptor comprising EGF repeats 13-36; and iii) determining if the molecule inhibits growth of tumor cells.

In certain embodiments, the present invention provides a pharmaceutical composition comprising an antibody that specifically binds to a non-ligand binding region of the extracellular domain of a human NOTCH receptor and inhibits growth of tumor cells.

In certain embodiments, the present invention provides a method of making an antibody that specifically binds to a non-ligand binding region of the extracellular domain of a human NOTCH receptor and inhibits growth of tumor cells.

In certain embodiments, the present invention provides an isolated nucleic acid that encodes an antibody that specifically binds to a non-ligand binding region of the extracellular domain of a human NOTCH receptor and inhibits growth of tumor cells.

Stem Cells and Solid Tumor Stem Cells

Common cancers arise in tissues that contain a subpopulation of proliferating cells that are responsible for replenishing the short-lived mature cells. In such organs, cell maturation is arranged in a hierarchy in which a rare population of stem cells give rise both to the more differentiated cells and perpetuate themselves through a process called self renewal (Akashi & Weissman, Developmental Biology of Hematopoiesis, Oxford Univ. Press, N Y, 2001; Spangrude et al., 1988, Science 241:58-61; Baum et al., 1992, PNAS 89:2804-8; Morrison et al., 1995, PNAS 92:10302-6; Morrison et al., 1996, Immunity 5:207-16; Morrison et al., 1995, Annu. Rev. Cell Dev. Biol. 11:35-71; Morrison et al., 1997, Dev. 124:1929-39; Morrison & Weissman, 1994, Immunity 1:661; Morrison et al., 1997, Cell 88:287-98; Uchida et al 2000, PNAS 97:14720-5; Morrison et at, 2000. Cell 101:499-510). Although it is likely that most tissues contain stem cells, due to their rarity these cells have been rigorously identified and purified to study their biological, molecular, and biochemical properties in only a few tissues. The best characterized stem cells are those that give rise to the hematopoietic system, called hematopoietic stem cells (HSCs). The utility of HSCs has been demonstrated in cancer therapy with their extensive use for bone marrow transplantation to regenerate the hematolymphoid system following myeloablative protocols (Baum et al., Bone Marrow Transplantation, Blackwell Scientific Publications, Boston, 1994). Understanding the cellular biology of the tissues in which cancers arise, and specifically of the stem cells residing in those tissues, promises to provide new insights into cancer biology.

Like the tissues in which they originate, solid tumors consist of a heterogeneous population of cells. That the majority of these cells lack tumorigenicity suggested that the development and maintenance of solid tumors also relies on a small population of stem cells (i.e., tumorigenic cancer cells) with the capacity to proliferate and efficiently give rise both to additional tumor stem cells (self-renewal) and to the majority of more differentiated tumor cells that lack tumorigenic potential (i.e., non-tumorigenic cancer cells). The concept of cancer stem cells was first introduced soon after the discovery of HSC and was established experimentally in acute myelogenous leukemia (AML) (Park et 1971, J. Natl. Cancer Inst. 46:411-22; Lapidot et al., 1994. Nature 367: 645-8; Bonnet & Dick, 1997, Nat. Med. 3:730-7; Hope et al., 2004, Nat. Immunol. 5:738-43). Stem cells from solid tumors have more recently been isolated based on their expression of a unique pattern of cell-surface receptors and on the assessment of their properties of self-renewal and proliferation in culture and in xenograft animal models. An ESA+ CD44+ CD24−/low Lineage-population greater than 50-fold enriched for the ability to form tumors relative to unfractionated tumor cells was discovered (Al-Hajj et al., 2003, PNAS 100:3983-8). The ability to isolate tumorigenic cancer stem cells from the bulk of non-tumorigenic tumor cells has led to the identification of cancer stem cell markers, genes with differential expression in cancer stem cells compared to non-tumorigenic tumor cells or normal breast epithelium, using microarray analysis. The present invention employs the knowledge of these identified cancer stem cell markers to study, characterize, diagnosis and treat cancer.

Cancer Stem Cell Marker Protein

Normal stem cells and cancer stem cells share the ability to proliferate and self-renew, thus it is not surprising that a number of genes that regulate normal stem cell development contribute to tumorigenesis (reviewed in Reya et al., 2001, Nature 414:105-111 and Taipale & Beachy, 2001, Nature 411:349-354). The present invention identifies Notch receptor, for example, Notch1 as a marker of cancer stem cells, implicating the Notch signaling pathway in the maintenance of cancer stem cells and as a target for treating cancer via the elimination of these tumorigenic cells.

The Notch signaling pathway is one of several critical regulators of embryonic pattern formation, post-embryonic tissue maintenance, and stem cell biology. More specifically, Notch signaling is involved in the process of lateral inhibition between adjacent cell fates and plays an important role in cell fate determination during asymmetric cell divisions. Unregulated Notch signaling is associated with numerous human cancers where it can alter the developmental fate of tumor cells to maintain them in an undifferentiated and proliferative state (Brennan and Brown, 2003, Breast Cancer Res. 5:69). Thus carcinogenesis can proceed by usurping homeostatic mechanisms controlling normal development and tissue repair by stem cell populations (Beachy et al., 2004, Nature 432:324).

The Notch receptor was first identified in *Drosophila* mutants with haploinsufficiency resulting in notches at the wing margin whereas loss-of-function producing an embryonic lethal "neurogenic" phenotype where cells of the epidermis switch fate to neural tissue (Moohr, 1919; Genet. 4:252; Poulson, 1937, PNAS 23:133; Poulson, 1940, J. Exp. Zool. 83:271). The Notch receptor is a single-pass transmembrane receptor containing numerous tandem epidermal growth factor (EGF)-like repeats and cysteine-rich Notch/LIN-12 repeats within a large extracellular domain (Wharton et al., 1985, Cell 43:567; Kidd et al., 1986, Mol. Cell Biol. 6:3094; reviewed in Artavanis et al., 1999, Science 284:770). Four mammalian Notch proteins have been identified (NOTCH1, NOTCH2, NOTCH3, and NOTCH4), and mutations in these receptors invariably result in developmental abnormalities and human pathologies including several cancers as described in detail below (Gridley, 1997, Mol. Cell Neurosci. 9:103; Joutel & Tournier-Lasserve, 1998, Semin. Cell Dev. Biol. 9:619-25).

The Notch receptor is activated by single-pass transmembrane ligands of the Delta, Serrated, Lag-2 (DSL) family. There are five known Notch ligands in mammals: Delta-like 1 (Dll1), Delta-like 3 (Dll3), Delta-like 4 (Dll4), Jagged 1 and Jagged 2 characterized by a DSL domain and tandem EGF-like repeats within the extracellular domain. The extracellular domain of the Notch receptor interacts with that of its ligands, typically on adjacent cells, resulting in two proteolytic cleavages of Notch, one extracellular mediated by an ADAM protease and one within the transmembrane domain mediated by gamma secretase. This latter cleavage generates the Notch intracellular domain (NICD), which then enters the nucleus where it activates the CBF1, Suppressor of Hairless [Su(H)], Lag-2 (CSL) family of transcription factors as the major downstream effectors to increase transcription of nuclear basic helix-loop-helix transcription factors of the Hairy and Enhancer of Split [E(spl)] family (Artavanis et al., 1999, Science 284:770; Brennan and Brown, 2003, Breast Cancer Res. 5:69; Iso et al., 2003, Arterioscler. Thromb. Vasc. Biol. 23:543). Alternative intracellular pathways involving the cytoplasmic protein Deltex identified in *Drosophila* may also exist in mammals (Martinez et al., 2002, Curr. Opin. Genet. Dev. 12:524-33), and this Deltex-dependent pathway may act to suppress expression of Wnt target genes (Brennan et al., 1999, Curr. Biol. 9:707-710; Lawrence et al., 2001, Curr. Biol. 11:375-85).

Hematopoietic stem cells (HSCs) are the best understood stem cells in the body, and Notch signaling is implicated both in their normal maintenance as well as in leukemic transformation (Kopper & Hajdu, 2004, Pathol. Oncol. Res. 10:69-73). HSCs are a rare population of cells that reside in a stromal niche within the adult bone marrow. These cells are characterized both by a unique gene expression profile as well as an ability to continuously give rise to more differentiated progenitor cells to reconstitute the entire hematopoietic system. Constitutive activation of Notch1 signaling in HSCs and progenitor cells establishes immortalized cell lines that generate both lymphoid and myeloid cells in vitro and in long-term reconstitution assays (Varnum-Finney et al., 2000, Nat. Med. 6:1278-81), and the presence of Jagged 1 increases engraftment of human bone marrow cell populations enriched for HSCs (Karanu et al., 2000, J. Exp. Med. 192:1365-72). More recently, Notch signaling has been demonstrate in HSCs in vivo and shown to be involved in inhibiting HSC differentiation. Furthermore, Notch signaling appears to be required for Wnt-mediated HSC self-renewal (Duncan et al., 2005, Nat. Immunol. 6:314).

The Notch signaling pathway also plays a central role in the maintenance of neural stem cells is implicated both in their normal maintenance as well as in brain cancers (Kopper & Hajdu, 2004, Pathol. Oncol. Res. 10:69-73; Purow et al., 2005, Cancer Res. 65:2353-63; Hallahan et al., 2004, Cancer Res. 64:7794-800). Neural stem cells give rise to all neuronal and glial cells in the mammalian nervous system during development, and more recently have been identified in the adult brain (Gage, 2000, Science 287:1433-8). Mice deficient for Notch1; the Notch target genes Hes1, 3, and 5; and a regulator of Notch signaling presenilin1 (PS1) show decreased numbers of embryonic neural stem cells. Furthermore, adult neural stem cells are reduced in the brains of PS1 heterozygote mice (Nakamura et al., 2000, J. Neurosci. 20:283-93; Hitoshi et al., 2002, Genes Dev. 16:846-58). The reduction in neural stem cells appears to result from their premature differentiation into neurons (Hatakeyama et al., 2004, Dev. 131:5539-50) suggesting that Notch signaling regulates neural stem cell differentiation and self-renewal.

Aberrant Notch signaling is implicated in a number of human cancers. The NOTCH1 gene in humans was first identified in a subset of T-cell acute lymphoblastic leukemias as a translocated locus resulting in activation of the Notch pathway (Ellisen et al., 1991, Cell 66:649-61). Constitutive activation of Notch1 signaling in T-cells in mouse models similarly generates T-cell lymphomas suggesting a causative role (Robey et al., 1996, Cell 87:483-92; Pear et al., 1996, J. Exp. Med. 183:2283-91; Yan et al., 2001, Blood 98:3793-9; Bellavia et al., 2000, EMBO J. 19:3337-48). Recently NOTCH1 point mutations, insertions, and deletions producing aberrant NOTCH1 signaling have been found to be frequently present in both childhood and adult T-cell acute lymphoblastic leukemia/lymphoma (Pear & Aster, 2004, Curr. Opin. Hematol. 11:416-33).

The frequent insertion of the mouse mammary tumor virus into both the Notch1 and Notch4 locus in mammary tumors and the resulting activated Notch protein fragments first implicated Notch signaling in breast cancer (Gallahan & Callahan, 1987, J. Virol. 61:66-74; Brennan & Brown, 2003, Breast Cancer Res. 5:69; Politi et al., 2004, Semin. Cancer Biol. 14:341-7). Further studies in transgenic mice have confirmed a role for Notch in ductal branching during normal mammary gland development, and a constitutively active form of Notch4 in mammary epithelial cells inhibits epithelial differentiation and results in tumorigenesis (Jhappan et al., 1992, Genes & Dev. 6:345-5; Callahan et al., 1996, Cancer Res. 56:1775-85; Smith et al., 1995, Cell Growth Differ, 6:563-77; Soriano et al., 2000. Int. J. Cancer 86:652-9; Uyttendaele et al, 1998, Dev. Biol. 196:204-17; Politi et al., 2004, Semin. Cancer Biol. 14:341-7). Currently the evidence for a role for Notch in human breast cancer is limited to the expression of Notch receptors in breast carcinomas and their correlation with clinical outcome (Weijzen et al., 2002, Nat. Med. 8:979-86; Parr et al., 2004, Int. J. Mol. Med. 14:779-86). Furthermore, overexpression of the Notch pathway has been observed in cervical cancers (Zagouras et al., 1995, PNAS 92:6414-8), renal cell carcinomas (Rae et al., 2000, Int. J. Cancer 88:726-32), head and neck squamous cell carcinomas (Leethanakul et al, 2000. Oncogene 19:3220-4), endometrial cancers (Suzuki et al., 2000, Int. J. Oncol. 17:1131-9), and neuroblastomas (van Limpt et al., 2000, Med. Pediatr. Oncol. 35; 554-8) suggestive of a potential role for Notch in the development of a number of neoplasms. Interestingly, Notch signaling might play a role in the maintenance of the undifferentiated state of Ape-mutant neoplastic cells of the colon (van Es & Clevers, 2005, Trends in Mol. Med. 11:496-502).

The Notch pathway is also involved in multiple aspects of vascular development including proliferation, migration, smooth muscle differentiation, angiogenesis and arterialvenous differentiation (iso et al., 2003, Arterioscler. Thromb. Vase. Biol. 23:543). For example, homozygous null mutations in Notch-1/4 and Jagged-1 as well as heterozygous loss of Dll4 result in severe though variable defects in arterial development and yolk sac vascularization. Furthermore, Dll1-deficient and Notch-2-hypomorphic mice embryos show hemorrhage that likely results from poor development of vascular structures (Gale et al., 2004, PNAS, 101:15949-54; Krebs et al., 2000. Genes Dev. 14:1343-52; Xue et al., 1999, Hum. Mel Genet. 8:723-30; Hrabe de Angelis et al., 1997, Nature 386:717-21; McCright et al., 2001, Dev. 128: 491-502). In human, mutations in JAGGED1 are associated with Alagille syndrome, a developmental disorder that includes vascular defects, and mutations in NOTCH3 are responsible for an inherited vascular dementia (CADASIL) in which vessel homeostasis is defective (Joutel et al., 1996, Nature 383:707-1.0).

The identification of NOTCH1, NOTCH4, DLL1 and DLL4 as genes expressed in cancer stem cells compared to normal breast epithelium suggests that targeting the Notch pathway can help eliminate not only the majority of nontumorigenic cancer cells, but the tumorigenic cells responsible for the formation and reoccurrence of solid tumors. Furthermore, because of the prominent role of angiogenesis in tumor formation and maintenance, targeting the Notch pathway can also effectively inhibit angiogenesis, starving a cancer of nutrients and contributing to its elimination.

Diagnostic Assays

The present invention provides a cancer stem cell marker the expression of which can be analyzed to detect, characterize, diagnosis or monitor a disease associated with expression of a cancer stem cell marker. In some embodiments, expression of a cancer stem cell marker is determined by polynucleotide expression such as, for example, mRNA encoding the cancer stem cell marker. The polynucleotide can be detected and quantified by any of a number of means well known in the art. In some embodiments, mRNA encoding a cancer stem cell marker is detected by in situ hybridization of tissue sections from, from example, a patient biopsy. Alternatively, RNA can be isolated from a tissue and detected by, for example, Northern blot, quantitative RT-PCR or microarrays. For example, total RNA can be extracted from a tissue sample and primers that specifically hybridize and amplify a cancer stem cell marker can be used to detect expression of a cancer stem cell marker polynucleotide using RT-PCR.

In other embodiments, expression of a cancer stem cell marker can be determined by detection of the corresponding polypeptide. The polypeptide can be detected and quantified by any of a number of means well known in the art. In some embodiments, a cancer stem cell marker polypeptide is detected using analytic biochemical methods such as, for example, electrophoresis, capillary electrophoresis, high performance liquid chromatography (HPLC) or thin layer chromatography (TLC). The isolated polypeptide can also be sequenced according to standard techniques. In some embodiments, a cancer stem cell marker protein is detected with antibodies raised against the protein using, for example, immunofluorescence or immunohistochemistry on tissue sections. Alternatively antibodies against a cancer stem cell marker can detect expression using, for example, ELISA, FACS, Western blot, immunoprecipitation or protein microarrays. For example, cancer stem cells can be isolated from a patient biopsy and expression of a cancer stem cell marker protein detected with fluorescently labeled antibodies using FACS. In another method, the cells expressing a cancer stem cell marker can be detected in vivo using labeled antibodies in typical imaging system. For example, antibodies labeled with paramagnetic isotopes can be used for magnetic resonance imaging (MRI).

In some embodiments of the present invention, a diagnostic assay comprises determining the expression or not of a cancer stem cell marker in tumor cells using, for example, immunohistochemistry, in situ hybridization, or RT-PCR. In other embodiments, a diagnostic assay comprises determining expression levels of a cancer stem cell marker using, for example, quantitative RT-PCR. In some embodiments, a diagnostic assay further comprises determining expression levels of a cancer stem cell marker compared to a control tissue such as, for example, normal epithelium.

Detection of a cancer stem cell marker expression can then be used to provide a prognosis and select a therapy. A prognosis can be based on any known risk expression of a cancer stem cell marker indicates. Furthermore, detection of a cancer stem cell marker can be used to select an appropriate therapy including, for example, treatment with an antagonist against the detected cancer stem cell marker. In certain embodiments, the antagonist is an antibody that specifically binds to the extracellular domain of a cancer stem cell marker protein such as a human NOTCH receptor selected from the group consisting of NOTCH1, NOTCH2, NOTCH3 and NOTCH4.

In other embodiments of the present invention, diagnosis of a patient is made by detection of a cancer stem cell gene signature as provided in U.S. patent application No. 60/690, 003. In certain embodiments, a patient is screened for the presence of a tumor or benign adenoma or polyps that indicate a pre-disposition to cancer. A biopsy from a patient is then analyzed for the presence of a cancer stem cell gene signature. In some embodiments, expression of a cancer stem cell gene signature is determined by polynucleotide expression such as, for example, mRNA encoding the cancer stem cell gene signature. The polynucleotides of a cancer gene signature can be detected and quantified by any of a number of means well known in the art. In other embodiments, expression of a cancer stem cell gene signature can be determined by detection of the corresponding polypeptides. The polypeptides can be detected and quantified by any of a number of means well known in the art.

Detection of a cancer stem cell gene signature can then be used to provide a prognosis and select a treatment. A prognosis can be based on the expression of any risk known at the time as reflected in the cancer stem cell gene signature. Furthermore, detection of a cancer stem cell gene signature can be used to select an appropriate therapy including, for example, treatment with an antagonist against a detected cancer stem cell marker. In some embodiments, the antagonist is an antibody that specifically binds to the extracellular domain of a cancer stem cell marker protein such as NOTCH'.

In other embodiments of the present invention, patients screened for the presence of colon adenomas or polyps are tested for allelic loss and somatic mutations via a genetic test. In some embodiments the genetic test screens for loss or mutations in the Wnt pathway including, for example, APC, Axin2 or beta-catenin. Notch signaling can play a role in maintenance of the undifferentiated state of neoplastic cells activated by unregulated Wnt signaling (van Es & Clevers, 2005, Trends in Mol. Med. 11:496-502), thus antagonists against the cancer stem cell marker NOTCH1 can be used as a treatment for Wnt-activated colon cancers. In some embodiments, the antagonist is an antibody that specifically binds to the extracellular domain of NOTCH1.

Cancer Stem Cell Marker Antagonists

In the context of the present invention, a suitable antagonist is an agent that can have one or more of the following effects, for example: interfere with the expression of a cancer stem cell marker; interfere with activation of a cancer stem cell signal transduction pathway by, for example, sterically inhibiting interactions between a cancer stem cell marker and its ligand, receptor or co-receptors; or bind to a cancer stem cell marker and trigger cell death or inhibit cell proliferation.

In certain embodiments, antagonists against a cancer stem cell marker act extracellularly to act upon or inhibit the function of a cancer stem cell marker. In certain embodiments, an antagonist is a small molecule that binds to the extracellular domain of a cancer stein cell marker protein. In certain embodiments, an antagonist of a cancer stem cell marker is proteinaceous. In some embodiments, proteinaceous antagonists of a cancer stem cell marker are antibodies that specifically bind to an extracellular epitope of a cancer stem cell marker protein. Extracellular binding of an antagonist against a cancer stem cell marker can inhibit the signaling of a cancer stem cell marker protein by inhibiting intrinsic activation (e.g. kinase activity) of a cancer stem cell marker and/or by sterically inhibiting the interaction, for example, of a cancer stem cell marker with its ligand, of a cancer stem cell marker with its receptor, of a cancer stem cell marker with a co-receptor, or of a cancer stem cell marker with the extracellular matrix. Furthermore, extracellular binding of an antagonist against a cancer stem cell marker can downregulate cell-surface expression of a cancer stem cell marker such as, for example, by internalization of a cancer stem cell marker protein and/or decreasing cell surface trafficking of a cancer stem cell marker.

In some embodiments, antagonists against a cancer stem cell marker bind to a cancer stem cell marker and have one or more of the following effects: inhibit proliferation of tumor cells, trigger cell death directly in tumor cells, or prevent metastasis of tumor cells. In certain embodiments, antagonists of a cancer stem cell marker trigger cell death via a conjugated toxin, chemotherapeutic agent, radioisotope, or other such agent. For example, an antibody against a cancer stem cell marker is conjugated to a toxin that is activated in tumor cells expressing the cancer stem cell marker by protein internalization. In other embodiments, antagonists of a cancer stem cell marker mediate cell death of a cell expressing the cancer stem cell marker protein via antibody-dependent cellular cytotoxicity (ADCC). ADCC involves cell lysis by effector cells that recognize the Fc portion of an antibody. Many lymphocytes, monocytes, tissue macrophages, granulocytes and eosinophils, for example, have Fc receptors and can mediate cytolysis (Dillman, 1994, J. Clin. Oncol. 12:1497). In some embodiments, an antagonist of a cancer stem cell marker is an antibody that triggers cell death of cell expressing a cancer stein cell marker protein by activating complement-dependent cytotoxicity (CDC). CDC yes binding of serum complement to the Fc portion an antibody and subsequent activation of the complement protein cascade, resulting in cell membrane damage and eventual cell death. Biological activity of antibodies is known to be determined, to a large extent, by the constant domains or Fc region of the antibody molecule (Uananue and Benacerraf, Textbook of Immunology, 2nd Edition, Williams & Wilkins, p. 218 (1984)). Antibodies of different classes and subclasses differ in this respect, as do antibodies of the same subclass but from different species. Of human antibodies, IgM is the most efficient class of antibodies to bind complement, followed by IgG1, IgG3, and IgG2 whereas IgG4 appears quite deficient in activating the complement cascade (Dillman, 1994, J. Clin. Oncol. 12:1497; Jefferis et al., 1998, Immunol. Rev. 163:59-76). According to the present invention, antibodies of those classes having the desired biological activity are prepared.

The ability of any particular antibody against a cancer stem cell to mediate lysis of the target cell by complement activation and/or ADCC can be assayed. The cells of interest are grown and labeled in vitro; the antibody is added to the cell culture in combination with either serum complement or immune cells which can be activated by the antigen antibody complexes. Cytolysis of the target cells is detected, for example, by the release of label from the lysed cells. In fact, antibodies can be screened using the patient's own serum as a source of complement and/or immune cells. The antibody that is capable of activating complement or mediating ADCC in the in vitro test can then be used therapeutically in that particular patient.

In other embodiments, antagonists of a cancer stem cell marker can trigger cell death indirectly by inhibiting angiogenesis. Angiogenesis is the process by which new blood vessels form from pre-existing vessels and is a fundamental process required for normal growth, for example, during embryonic development, wound healing and in response to ovulation. Solid tumor growth larger than 1-2 mm$^2$ also requires angiogenesis to supply nutrients and oxygen without which tumor cells die. Thus in certain embodiments, an antagonist of a cancer stem cell marker targets vascular cells that express the cancer stem cell marker including, for example, endothelial cells, smooth muscle cells or components of the extracellular matrix required for vascular assembly. In other embodiments, an antagonist of a cancer stem cell marker inhibits growth factor signaling required by vascular cell recruitment, assembly, maintenance or survival.

Antibodies

Recently the application of antibodies to target tumor cells has been discovered and used successfully against CD20 expressing B-cells in non-Hodgkin Lymphoma and HER2 and EGFR overexpressing breast cancers. Antibodies against growth factor receptors can inhibit growth factor receptor function, inhibiting the growth of tumor cells as well as rendering these cells more susceptible to cytotoxic agents. Additionally, antibodies can mediate complement-dependent cytotoxicity or antibody-dependent cellular cytotoxicity to kill tumors expressing a target antigen. Antibodies can also be directly conjugated to toxins or radioisotopes to mediate tumor cell killing. Furthermore, tumor survival depends on neo-vascularization, and targeting angiogenesis via antibodies against VEGF has been used successfully to prolong patient survival.

The present invention provides isolated antibodies against a cancer stem cell marker. The antibody, or antibody fragment, can be any monoclonal or polyclonal antibody that specifically recognizes the described cancer stem cell marker. In some embodiments, the present invention provides monoclonal antibodies, or fragments thereof, that specifically bind to a cancer stem cell marker polypeptide described herein. In some embodiments, the monoclonal antibodies, or fragments thereof, are chimeric or humanized antibodies that specifically bind to the extracellular domain of a cancer stem cell marker polypeptide described herein. In other embodiments, the monoclonal antibodies, or fragments thereof, are human antibodies that specifically bind to the extracellular domain of a cancer stem cell marker polypeptide described herein.

The antibodies against a cancer stem cell marker find use in the experimental diagnostic and therapeutic methods described herein. In certain embodiments, the antibodies of the present invention are used to detect the expression of a cancer stem cell marker protein in biological samples such as, for example, a patient tissue biopsy, pleural effusion, or blood sample. Tissue biopsies can be sectioned and protein detected using, for example, immunofluorescence or immunohistochemistry. Alternatively, individual cells from a sample are isolated, and protein expression detected on fixed or live cells by FACS analysis. Furthermore, the antibodies can be used on protein arrays to detect expression of a cancer stem cell marker, for example, on tumor cells, in cell lysates, or in other protein samples. In other embodiments, the antibodies of the present invention are used to inhibit the growth of tumor cells by contacting the antibodies with tumor cells either in vitro cell based assays or in vivo animal models. In still other embodiments, the antibodies are used to treat cancer in a human patient by administering a therapeutically effective amount of an antibody against a cancer stem cell marker.

Polyclonal antibodies can be prepared by any known method. Polyclonal antibodies are raised by immunizing an animal (e.g. a rabbit, rat, mouse, donkey, etc.) by multiple subcutaneous or intraperitoneal injections of the relevant antigen (a purified peptide fragment, full-length recombinant protein, fusion protein, etc.) optionally conjugated to keyhole limpet hemocyanin (KLH), serum albumin, etc. diluted in sterile saline and combined with an adjuvant (e.g. Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay such as radioimmunoassay (RIA) or enzyme-linked immunosorbent assay (ELISA) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity, affinity, etc. of a monoclonal antibody.

More generally, modified antibodies useful in the present invention may be obtained or derived from any antibody. Further, the parent or precursor antibody, or fragment thereof, used to generate the disclosed modified antibodies may be murine, human, chimeric, humanized, non-human primate or primatized. In other embodiments the modified antibodies of the present invention can comprise single chain antibody constructs (such as that disclosed in U.S. Pat. No. 5,892,019, which is incorporated herein by reference) having altered constant domains as described herein. Consequently, any of these types of antibodies modified in accordance with the teachings herein are compatible with this invention.

According to the present invention, techniques can be adapted for the production of single-chain antibodies specific to a polypeptide of the invention (see U.S. Pat. No. 4,946,778). In addition, methods can be adapted for the construction of Fab expression libraries (Huse, et al., Science 246:1275-1281 (1989)) to allow rapid and effective identification of monoclonal Fab fragments with the desired specificity for NOTCH, or derivatives, fragments, analogs or homologs thereof. Antibody fragments that contain the idiotypes to a polypeptide of the invention may be produced by techniques in the art including, but not limited to: (a) an $F(ab')_2$ fragment produced by pepsin digestion of an antibody molecule; (b) an Fab fragment generated by reducing the disulfide bridges of an $F(ab')_2$ fragment, (c) an Fab fragment generated by the treatment of the antibody molecule with papain and a reducing agent, and (d) Fv fragments.

Bispecific antibodies are also within the scope of the invention. Bispecific antibodies are monoclonal, preferably human or humanized, antibodies that have binding specificities for at least two different antigens. In the present case, one of the binding specificities is for an antigenic polypeptide of the invention (NOTCH, or a fragment thereof). While the second binding target is any other antigen, and advantageously is a cell surface protein, or receptor or receptor subunit.

Methods for making bispecific antibodies are known in the art. Traditionally the recombinant production of bispecific antibodies is based on the co-expression of two immunoglobulin heavy chain/light chain pairs, where the two heavy chains have different specificities (Milstein and Cuello, Nature 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography.

Antibody variable domains with the desired binding specificities can be fused to immunoglobulin constant domain sequences. The fusion is with an immunoglobulin heavy chain constant domain, comprising at least part of the hinge, CH2 and CH3 regions. The first heavy chain constant region (CH1) containing the site necessary for light chain binding can be present in at least one of the fusions. DNA encoding the immunoglobulin heavy chain fusions and, if desired, the immunoglobulin light chain, are inserted into separate expression vectors, and are co-transfected into a suitable host organism. Further details of generating bispecific antibodies can be found in Suresh et al., Methods in Enzymology 121:210 (1986).

Bispecific antibodies can be prepared as full-length antibodies or antibody fragments. Techniques for generating bispecific antibodies from antibody fragments have been described in the literature. For example, bispecific antibodies can be prepared using chemical linkage. In addition, Brennan et al., Science 229:81 (1985) describe a procedure wherein intact antibodies are proteolytically cleaved to generate $F(ab')_2$ fragments.

Additionally, Fab' fragments can be directly recovered from *E. coli* and chemically coupled to form bispecific antibodies (Shalaby et al., J. Exp. Med. 175:217-225 (1992)) These methods can be used in the production of a fully humanized bispecific antibody $F(ab')_2$ molecule.

Antibodies with more than two valencies are also contemplated. For example, trispecific antibodies can be prepared (Tutt et al., J. Immunol. 147:60 (1991)).

Exemplary bispecific antibodies can bind to two different epitopes, at least one of which originates in a polypeptide of the invention. Alternatively, an anti-antigenic arm of an immunoglobulin molecule can be combined with an arm which binds to a triggering molecule on a leukocyte such as a T cell receptor molecule (e.g. CD2, CD3, CD28, or B7), or Fc receptors for IgG so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA.

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the polypeptides of NOTCH. In this regard, the variable region may comprise or be derived from any type of mammal that can be induced to mount a humoral response and generate immunoglobulins against the desired tumor associated antigen. As such, the variable region of the modified antibodies can be, for example, of human, murine, non-human primate (e.g. cynomolgus monkeys, macaques, etc.) or origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In some embodiments, of the present invention the monoclonal antibody against a cancer stem cell marker is a humanized antibody. Humanized antibodies are antibodies that contain minimal sequences from non-human (e.g. murine) antibodies within the variable regions. Such antibodies are used therapeutically to reduce antigenicity and HAMA (human anti-mouse antibody) responses when administered to a human subject. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDR of a human antibody with that of a non-human antibody (e.g. mouse, rat, rabbit, hamster, etc.) having the desired specificity, affinity, and capability (Jones et al., 1986, Nature, 321:522-525; Riechmann et al., 1988, Nature, 332:323-327; Verhoeyen et al., 1988, Science, 239: 1534-1536). The humanized antibody can be further modified by the substitution of additional residue either in the Fv framework region and or within the replaced non-human residues to refine and optimize antibody specificity, affinity, and/or capability.

Human antibodies can be directly prepared using various techniques known in the art. Immortalized human B lymphocytes immunized in vitro or isolated from an immunized individual that produce an antibody directed against a target antigen can be generated (See, for example, Cole et al., Monoclonal Antibodies and Cancer Therapy, Alan R. Liss, p. 77 (1985); Boemer et al., 1991, J. Immunol., 147 (0:86-95; and U.S. Pat. No. 5,750,373): Also, the human antibody can be selected from a phage library, where that phage library expresses human antibodies (Vaughan et al., 1996, Nature Biotechnology, 14:309-314; Sheets et al., 1998, PNAS, 95:6157-6162; Hoogenboom and Winter, 1991; J. Mol. Biol., 227:381; Marks et al., 1991, J. Mol. Biol., 222:581). Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

As an alternative to humanization, human antibodies can be generated. For example, it is now possible to produce transgenic animals mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno, 7:33 (1993); U.S. Pat. Nos. 5,545, 806, 5,569,825, 5,591,669 (all of GenPharm); U.S. Pat. No. 5,545,807; and WO 97/17852.

Alternatively, phage display technology can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats. Several sources of V-gene segments can be used for phage display. A diverse array of anti-oxazolone antibodies have been isolated from a small random combinatorial library of V genes derived from the spleens of immunized mice. A repertoire of V genes from unimmunized human donors can be constructed and antibodies to a diverse array of antigens (including self-antigens) can be isolated.

As discussed above, human antibodies may also be generated by in vitro activated B cells (see U.S. Pat. Nos. 5,567,610 and 5,229,275).

It will be appreciated that grafting the entire non-human variable domains onto human constant regions will produce "classic" chimeric antibodies. In the context of the present application the term "chimeric antibodies" will be held to mean any antibody wherein the immunoreactive region or site is obtained or derived from a first species and the constant region (which may be intact, partial or modified in accordance with this invention) is obtained from a second species. In some embodiments, the antigen binding region or site will be from a non-human source (e.g. mouse) and the constant region is human. While the immunogenic specificity of the variable region is not generally affected by its source, a human constant region is less likely to elicit an immune response from a human subject than would the constant region from a non-human source.

The variable domains in both the heavy and light chains are altered by at least partial replacement of one or more CDRs and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. Ti must be emphasized that it may not be necessary to replace all of the CDRs with the complete CDRs from the donor variable region to transfer the antigen binding capacity of one variable domain to another. Rather, it may only be necessary to transfer those residues that are necessary to maintain the activity of the antigen binding site. Given the explanations set forth in U.S. Pat. Nos. 5,585,089, 5,693,761 and 5,693,762, it will be well within the art, either by carrying out routine experimentation or by trial and error testing to obtain a functional antibody with reduced immunogenicity.

Alterations to the variable region notwithstanding, it will be appreciated that the modified antibodies of this invention will comprise antibodies, or immunoreactive fragments thereof, in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein may comprise alterations or modifications to one or more of the three heavy chain constant domains (CH1, CH2 or CH3) and/or to the light chain constant domain (CL). In some embodiments of the invention modified constant regions wherein one or more domains are partially or entirely deleted are contemplated. In other embodiments the modified antibodies will comprise domain deleted constructs or variants wherein the entire CH2 domain has been removed (ΔCH2 constructs). In still other embodiments the omitted constant region domain will be replaced by a short amino acid spacer (e.g. 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and can also be involved in autoimmune hypersensitivity. Further, antibodies bind to cells via the Fe region, with a Fe receptor site on the antibody Fe region binding to a Fe receptor (FcR) on a cell. There are a number of Fe receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. Although various Fe receptors and receptor sites have been studied to a certain extent, there is still much which is unknown about their location, structure and functioning.

While not limiting the scope of the present invention, it is believed that antibodies comprising constant regions modified as described herein provide for altered effector functions that, in turn, affect the biological profile of the administered antibody. For example, the deletion or inactivation (through point mutations or other means) of a constant region domain may reduce Fc receptor binding of the circulating modified antibody thereby increasing tumor localization. In other cases it may be that constant region modifications, consistent with this invention, moderate complement binding and thus reduce the serum half life and nonspecific association of a conjugated cytotoxin. Yet other modifications of the constant region may be used to eliminate disulfide linkages or oligosaccharide moieties that allow for enhanced localization due to increased antigen specificity or antibody flexibility. Similarly, modifications to the constant region in accordance with this invention may easily be made using well known biochemical or molecular engineering techniques.

It will be noted that the modified antibodies may be engineered to fuse the CH3 domain directly to the hinge region of the respective modified antibodies. In other constructs it may be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer may be added, for instance, to ensure that the regulatory elements of the constant domain remain free and accessible or that the hinge region remains flexible. However, it should be noted that amino acid spacers may, in some cases, prove to be immunogenic and elicit an unwanted immune response against the construct. Accordingly, any spacer added to the construct be relatively non-immunogenic or, even omitted altogether if the desired biochemical qualities of the modified antibodies may be maintained.

Besides the deletion of whole constant region domains, it will be appreciated that the antibodies of the present invention may be provided by the partial deletion or substitution of a few or even a single amino acid. For example, the mutation of a single amino acid in selected areas of the CH2 domain may be enough to substantially reduce Fe binding and thereby increase tumor localization. Similarly, it may be desirable to simply delete that part of one or more constant region domains that control the effector function (e.g. complement CLQ binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g. Fe binding) while substantially maintaining the configuration and immunogenic profile of the modified antibody. Yet other embodiments may comprise the addition of one or more amino acids to the constant region to enhance desirable characteristics such as effector function or provide for more cytotoxin or carbohydrate attachment. In such embodiments it can be desirable to insert or replicate specific sequences derived from selected constant region domains.

This invention also encompasses bispecific antibodies that specifically recognize a cancer stem cell marker. Bispecific antibodies are antibodies that are capable of specifically recognizing and binding at least two different epitopes. The different epitopes can either be within the same molecule (e.g. the same cancer stem cell marker polypeptide) or on different molecules such that both, for example, the antibodies can specifically recognize and bind a cancer stem cell marker as well as, for example, 1) an effector molecule on a leukocyte such as a T-cell receptor (e.g. CD3) or Fe receptor (e.g. CD64, CD32, or CD16) or 2) a cytotoxic agent as described in detail below. Bispecific antibodies can be intact antibodies or antibody fragments. Techniques for making bispecific antibodies are common in the art (Millstein et al., 1983, Nature 305:537-539; Brennan et al., 1985, Science 229:81; Suresh et al, 1986, Methods in Enzymol. 121:120; Traunecker et al., 1991, EMBO J. 10:3655-3659; Shalaby et al., 1992, J. Exp. Med. 175:217-225; Kostelny et al., 1992, J. Immunol. 148:1547-1553; Gruber et al., 1994, J. Immunol. 152:5368; and U.S. Pat. No. 5,731,168).

In certain embodiments of the invention, it can be desirable to use an antibody fragment, rather than an intact antibody, to increase tumor penetration, for example. Various techniques are known for the production of antibody fragments. Traditionally, these fragments are derived via proteolytic digestion of intact antibodies (for example Morimoto et al., 1993, Journal of Biochemical and Biophysical Methods 24:107-117 and Brennan et al., 1985, Science, 229:81). However, these fragments are now typically produced directly by recombinant host cells as described above. Thus Fab, Fv, and scfv antibody fragments can all be expressed in and secreted from *E. coli* or other host cells, thus allowing the production of large amounts of these fragments. Alternatively, such antibody fragments can be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The invention also pertains to immunoconjugates comprising an antibody conjugated to a cytotoxic agent. Cytotoxic agents include chemotherapeutic agents, growth inhibitory agents, toxins (e.g., an enzymatically active toxin of bacterial, fungal, plant, or animal origin, or fragments thereof), radioactive isotopes (i.e., a radioconjugate), etc. Chemotherapeutic agents useful in the generation of such immunoconjugates include, for example, methotrexate, adriamicin, doxorubicin, melphalan, mitomycin C, chlorambucil, daunorubicin or other intercalating agents. Enzymatically active toxins and fragments thereof that can be used include diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (DAPI, PAM, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies including 212Bi, 131I, 131In, 90Y, and 186Re. Conjugates of the antibody and cytotoxic agent are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoye-ethylenediamine), diisocyanates (such as tolyene 2,6-diisocyanate), and bis-active fluorine compounds (such as 1,5-difluoro-2,4-dinitrobenzene). Conjugates of an antibody and one or more small molecule toxins, such as a calicheamicin, maytansinoids, a trichothene, and CC1065, and the derivatives of these toxins that have toxin activity, can also be used.

Conjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

In some embodiments the antibody of the invention contains human Fc regions that are modified to enhance effector function, for example, antigen-dependent cell-mediated cytotoxicity (ADCC) and/or complement dependent cytotoxicity (CDC). This can be achieved by introducing one or more amino acid substitutions in an Fc region of the antibody. For example, cysteine residue(s) can be introduced in the Fc region to allow interchain disulfide bond formation in this region to improve complement-mediated cell killing and antibody-dependent cellular cytotoxicity (ADCC) (Caron et al., 1992, J. Exp Med. 176:1191-1195; Shopes, 1992, Immunol. 148:2918-2922). Homodimeric antibodies with enhanced anti-tumor activity can also be prepared using heterobifunctional cross-linkers as described in Wolff et al., 1993, Cancer Research 53:2560-2565. Alternatively, an antibody can be engineered which has dual Fc regions (Stevenson et al., 1989, Anti-Cancer Drug Design 3:219-230).

Regardless of how useful quantities are obtained, the antibodies of the present invention can be used in any one of a number of conjugated (i.e. an immunoconjugate) or unconjugated forms. Alternatively, the antibodies of this invention can be used in a nonconjugated or "naked" form to harness the subject's natural defense mechanisms including complement-dependent cytotoxicity (CDC) and antibody dependent cellular toxicity (ADCC) to eliminate the malignant cells. In some embodiments, the antibodies can be conjugated to radioisotopes, such as $^{90}$Y, $^{125}$I, $^{131}$I, $^{123}$I, $^{105}$Rh, $^{153}$Sm, $^{67}$Cu, $^{67}$Ga, $^{166}$Ho, $^{177}$Lu, $^{186}$Re and $^{188}$Re using anyone of a number of well known chelators or direct labeling. In other embodiments, the disclosed compositions can comprise antibodies coupled to drugs, prodrugs or biological response modifiers such as methotrexate, adriamycin, and lymphokines such as interferon. Still other embodiments of the present invention comprise the use of antibodies conjugated to specific biotoxins such as ricin or diptheria toxin. In yet other embodiments the modified antibodies can be complexed with other immunologically active ligands (e.g. antibodies or fragments thereof) wherein the resulting molecule binds to both the neoplastic cell and an effector cell such as a T cell. The selection of which conjugated or unconjugated modified antibody to use will depend of the type and stage of cancer, use of adjunct treatment (e.g., chemotherapy or external radiation) and patient condition. It will be appreciated that one could readily make such a selection in view of the teachings herein.

Antibody Binding Assays

The antibodies of the present invention can be assayed for immunospecific binding by any method known in the art. The immunoassays which can be used include, but are not limited to, competitive and non-competitive assay systems using techniques such as BIAcore analysis, FACS analysis, immunofluorescence, immunocytochemistry, Western blots, radioimmunoassays, ELISA, "sandwich" immunoassays, immunoprecipitation assays, precipitin reactions, gel diffusion precipitin reactions, immunodiffusion ion assays, agglutination assays, complement-fixation assays, immunoradiometric assays, fluorescent immunoassays, and protein A immunoassays. Such assays are routine and well known in the art (see, e.g., Ausubel et al, eds, 1994, Current Protocols in Molecular Biology, Vol. 1, John Wiley Sons, Inc., New York, which is incorporated by reference herein in its entirety).

In some embodiments, of the present invention the immunospecificity of an antibody against a cancer stem cell marker is determined using ELISA. An ELISA assay comprises preparing antigen, coating wells of a 96 well microliter plate with antigen, adding the antibody against a cancer stem cell marker conjugated to a detectable compound such as an enzymatic substrate (e.g. horseradish peroxidase or alkaline phosphatase) to the well, incubating for a period of time and detecting the presence of the antigen. Alternatively the antibody against a cancer stem cell marker is not conjugated to a detectable compound, but instead a second conjugated antibody that recognizes the antibody against a cancer stem cell marker is added to the well. Further, instead of coating the well with the antigen, the antibody against a cancer stem cell marker can be coated to the well and a second antibody conjugated to a detectable compound can be added following the addition of the antigen to the coated well. It is known as to the parameters that can be modified to increase the signal detected as well as other variations of ELISAs known in the art (see e.g. Ausubel et al, ells, 1994, Current Protocols in Molecular Biology, Vol. 1, John Wiley & Sons, Inc., New York at 11.2.1).

The binding affinity of an antibody to a cancer stem cell marker antigen and the off-rate of an antibody-antigen interaction can be determined by competitive binding assays. One example of a competitive binding assay is a radioimmunoassay comprising the incubation of labeled antigen (e.g. 3H or 125I), or fragment or variant thereof, with the antibody of interest in the presence of increasing amounts of unlabeled antigen followed by the detection of the antibody bound to the labeled antigen. The affinity of the antibody against a cancer stem cell marker and the binding off rates can be determined from the data by scatchard plot analysis. In some embodiments, BIAcore kinetic analysis is used to determine the binding on and off rates of antibodies against a cancer stem cell marker. BIAcore kinetic analysis comprises analyzing the binding and dissociation of antibodies from chips with immobilized cancer stem cell marker antigens on their surface.

Polynucleotides

The invention is directed to isolated polynucleotides encoding the polypeptides of SEQ ID NOS: 2, 3, 5, 7-17 and 19, as well as the polynucleotides of SEQ ID NOS: 1, 4, 6 and 18. The polynucleotides of the invention can be in the form of RNA or in the form of DNA, which DNA includes cDNA, gnomic DNA, and synthetic DNA. The DNA can be double-stranded or single-stranded, and if single stranded can be the coding strand or non-coding (anti-sense) strand.

Thus, the term "polynucleotide encoding a polypeptide" encompasses a polynucleotide which includes only coding sequences for the polypeptide as well as a polynucleotide which includes additional coding and/or non-coding sequences.

The present invention further relates to variants of the hereinabove described polynucleotides which encode for fragments, analogs, and derivatives. The variant of the polynucleotide can be a naturally occurring allelic variant of the polynucleotide or a non-naturally occurring variant of the polynucleotide.

As hereinabove indicated, the polynucleotide can have a coding sequence which is a naturally occurring allelic variant of the coding sequence of the disclosed polypeptides. As known in the art, an allelic variant is an alternate form of a polynucleotide sequence which have a substitution, deletion or addition of one or more nucleotides, which does not substantially alter the function of the encoded polypeptide.

The present invention also includes polynucleotides, wherein the coding sequence for the mature polypeptide can be fused in the same reading frame to a polynucleotide which aids in expression and secretion of a polypeptide from a host cell, for example, a leader sequence which functions as a secretory sequence for controlling transport of a polypeptide from the cell. The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention can encode for a mature protein, or for a protein having a prosequence or for a protein having both a prosequence and presequence (leader sequence).

The polynucleotides of the present invention can also have the coding sequence fused in frame to a marker sequence which allows for purification of the polypeptide of the present invention. The marker sequence can be a hexa-histidine tag supplied by a pQE-9 vector to provide for purification of the mature polypeptide fused to the marker in the case of a bacterial host, or, for example, the marker sequence can be a hemagglutinin (HA) tag when a mammalian host, e.g. COS-7 cells, is used. The HA tag corresponds to an epitope derived from the influenza hemagglutinin protein (Wilson, I., et al., Cell 37:767 (1984)).

Further embodiments of the invention include isolated nucleic acid molecules comprising a polynucleotide having a nucleotide sequence at least 90% identical, 95% identical, and in some embodiments, at least 96%, 97%, 98% or 99% identical to the disclosed sequences.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2: 482 489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*).

Polypeptides

The polypeptides of the present invention can be recombinant polypeptides, natural polypeptides, or synthetic polypeptides having the sequence of SEQ ID NOS: 2, 3, 5, 7-17 and 19, as well as the polypeptides encoded by the polynucleotides of SEQ ID NOS:1, 4, 6 and 8.

It will be recognized in the art that some amino acid sequences of the invention can be varied without significant effect of the structure or function of the protein. If such differences in sequence are contemplated, it should be remembered that there will be critical areas on the protein which determine activity.

Thus, the invention further includes variations of the polypeptides which show substantial activity or which include regions of NOTCH protein such as the protein portions discussed herein. Such mutants include deletions, insertions, inversions, repeats, and type substitutions. As indicated above, guidance concerning which amino acid changes are likely to be phenotypically silent can be found in Bowie, et al., "Deciphering the Message in Protein Sequences: Tolerance to Amino Acid Substitutions," Science 247:1306 1310 (1990).

Thus, the fragments, derivatives, or analogs of the polypeptides of the invention can be: (I) one in which one or more of the amino acid residues are substituted with a conserved or non-conserved amino acid residue (often a conserved amino acid residue) and such substituted amino acid residue can or can not be one encoded by the genetic code; or (ii) one in which one or more of the amino acid residues includes a substituent group; or (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence which is employed for purification of the mature polypeptide or a proprotein sequence. Such fragments, derivatives, and analogs are deemed to be within the scope of the teachings herein.

Of particular interest are substitutions of charged amino acids with another charged amino acid and with neutral or negatively charged amino acids. The latter results in proteins with reduced positive charge to improve the characteristics of the NOTCH protein. The prevention of aggregation is highly desirable. Aggregation of proteins not only results in a loss of activity but can also be problematic when preparing pharmaceutical formulations, because they can be immunogenic. (Pinckard et al., Clin. Exp. Immunol. 2:331-340 (1967); Robbins et al., Diabetes 36:838-845 (1987); Cleland et al. Crit. Rev. Therapeutic Drug Carrier Systems 10:307-377 (1993)).

As indicated, changes are typically of a minor nature, such as conservative amino acid substitutions that do not significantly affect the folding or activity of the protein (see Tables 1 and 2).

TABLE 1

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

TABLE 2

Amino Acid Substitutions

| Original Residue | Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Lys; Arg |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |
| Ser (S) | Thr | Thr |
| Thr (T) | Ser | Ser |
| Trp (W) | Tyr | Tyr |
| Tyr (Y) | Phe | Trp; Phe; Thr; Ser |
| Val (V) | Leu | Ile; Leu; Met; Phe; Ala; norleucine |

Of course, the number of amino acid substitutions made depends on many factors, including those described above. Generally speaking, the number of substitutions for any given NOTCH polypeptide will not be more than 50, 40, 30, 25, 20, 15, 10, 5 or 3.

The polypeptides and polynucleotides of the present invention are provided in an isolated form, and at times are purified to homogeneity.

The polypeptides of the present invention include the polypeptides of SEQ NOS: 2, 3, 5, 7-17 and 19 as well as polypeptides which have at least 90% similarity (at certain times at least 90% identity) to the polypeptides of SEQ ID NOS: 2, 3, 5, 7-17 and 19, and at least 95% similarity (at certain times at least 95% identity) to the polypeptides of SEQ ID NOS; 2, 3, 5, 7-17 and 19, and still other embodiments, 96%, 97%, 98%, or 99% similarity (at certain times 96%, 97%, 98%, or 99% identity) to the polypeptides of SEQ ID NOS: 2, 3, 5, 7-17 and 19. As known in the art "similarity" between two polypeptides is determined by comparing the amino acid sequence and its conserved amino acid substitutes of one polypeptide to the sequence of a second polypeptide.

Fragments or portions of the polypeptides of the present invention can be employed for producing the corresponding full-length polypeptide by peptide synthesis; therefore, the fragments can be employed as intermediates for producing the full-length polypeptides. Fragments or portions of the polynucleotides of the present invention can be used to synthesize full-length polynucleotides of the present invention.

A fragment of the proteins of this invention is a portion or all of a protein which is capable of binding to a cancer stem cell marker protein or cancer stem cell protein binding partner (e.g. a receptor, co-receptor, ligand, or co-ligand). This fragment has a high affinity for a cancer stem cell marker protein or cancer stem cell protein binding partner (e.g. a receptor, co-receptor, ligand, or co-ligand). Certain fragments of fusion proteins are protein fragments comprising at least part of the extracellular portion of a cancer stem cell marker protein or cancer stem cell protein binding partner bound to at least part of a constant region of an immunoglobulin. The affinity is typically in the range of about 10-11 to 10-12 M, although the affinity can vary considerably with fragments of different sizes, ranging from 10-7 to 10-13 M. In some embodiments, the fragment is about 10-110 amino acids in length and comprises the cancer stem cell marker protein ligand binding site linked to at least part of a constant region of an immunoglobulin.

The polypeptides and analogs can be further modified to contain additional chemical moieties not normally part of the protein. Those derivatized moieties can improve the solubility, the biological half life or absorption of the protein. The moieties can also reduce or eliminate any desirable side effects of the proteins and the like. An overview for those moieties can be found in REMINGTON'S PHARMACEUTICAL SCIENCES, 20th ed., Mack Publishing Co., Easton, Pa. (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. For example, eDNA can be obtained by screening a human cDNA library with a labeled DNA fragment encoding the polypeptide of SEQ ID NO: 1 and identifying positive clones by autoradiography. Further rounds of plaque purification and hybridization are performed using conventional methods.

In some embodiments of a recombinant method, a DNA sequence is constructed by isolating or synthesizing a DNA sequence encoding a wild-type protein of interest. Optionally, the sequence can be mutagenized by site-specific mutagenesis to provide functional analogs thereof. See, e.g. Zoeller et al., Proc.-Nat Acad. Sci. USA 81:5662-5066 (1984) and U.S. Pat. No. 4,588,585. Another method of constructing a DNA sequence encoding a polypeptide of interest would be by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced.

Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the mutant DNA sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene is operatively linked to transcriptional and translational expression control sequences that are functional in the chosen expression host.

Recombinant expression vectors are used to amplify and express DNA encoding cancer stem cell marker polypeptide fusions. Recombinant expression vectors are replicable DNA constructs which have synthetic or cDNA-derived DNA fragments encoding a cancer stem cell marker polypeptide fusion or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor Which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous and, in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovims and cytomegalovirus. Useful expression vectors for bacterial hosts include known bacterial plasmids, such as plasmids from *Escherichia coli*, including pCR 1, pBR322, pMB9 and their derivatives, wider host range plasmids, such as M13 and filamentous single-stranded DNA phages.

Suitable host cells for expression of a cancer stem cell marker protein include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al, (Cloning Vectors: A Laboratory Manual, Elsevier, N.Y., 1985), the relevant disclosure of which is hereby incorporated by reference.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sates, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAF) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a cancer stem cell protein-Fe composition. Some or all of the foregoing purification steps, in various combinations, can also be employed to provide a homogeneous recombinant protein.

Recombinant, protein produced in bacterial culture is usually isolated by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Inhibiting Tumor Cell Growth

The present invention also provides methods for inhibiting the growth of tumorigenic cells expressing a cancer stem cell marker using the antagonists of a cancer stem cell marker described herein. In some embodiments, the method of inhibiting the growth of tumorigenic cells expressing a cancer stem cell marker comprises contacting the cell with an antagonist against a cancer stem cell marker in vitro. For example, an immortalized cell line or a cancer cell line that expresses a cancer stein cell marker is cultured in medium to which is added an antagonist of the expressed cancer stem cell marker to inhibit cell growth. Alternatively tumor cells and/or tumor stem cells are isolated from a patient sample such as, for example, a tissue biopsy, pleural effusion, or blood sample and cultured in medium to which is added an antagonist of a cancer stein cell marker to inhibit cell growth. In some embodiments, the antagonist is an antibody that specifically recognizes an epitope of a cancer stem cell marker protein. For example, antibodies against a cancer stem cell marker protein can be added to the culture medium of isolated cancer stem cells to inhibit cell growth.

In some embodiments, the method of inhibiting the growth of tumorigenic cells expressing a cancer stem cell marker comprises contacting the cell with an antagonist against a cancer stem cell marker in vivo. In certain embodiments, contacting a tumorigenic cell with an antagonist to a cancer stem cell marker is undertaken in an animal model. For example, xenografts expressing a cancer stein cell marker are grown in immunocompromised mice (e.g. NOD/SCID mice) that are administered an antagonist to a cancer stem cell marker to inhibit tumor growth. Alternatively, cancer stem cells that express a cancer stem cell marker are isolated from a patient sample such as, for example, a tissue biopsy, pleural effusion, or blood sample and injected into immunocompromised mice that are then administered an antagonist against the cancer stem cell marker to inhibit tumor cell growth. In some embodiments, the antagonist of a cancer stem cell marker is administered at the same time or shortly after introduction of tumorigenic cells into the animal to prevent tumor growth. In other embodiments, the antagonist of a cancer stem cell marker is administered as a therapeutic after the tumorigenic cells have grown to a specified size. In some embodiments, the antagonist is a cancer stem cell marker protein fusion that specifically binds to a cancer stem cell marker protein or cancer stem cell marker binding protein (e.g. receptor, co-receptor, ligand, or co-ligand). In certain embodiments, the antagonist is an antibody that specifically recognizes an epitope of a cancer stem cell marker. In certain embodiments, contacting a tumorigenic cell with an antagonist to a cancer stem cell is undertaken in a human patient diagnosed with cancer. In some embodiments, the antagonist is a cancer stem cell marker protein fusion that specifically binds to a cancer stem cell marker protein or cancer stem cell marker binding protein (e.g. receptor, co-receptor, ligand, or co-ligand). In other embodiments, the antagonist is an antibody that specifically recognizes an epitope of a cancer stem cell marker.

Pharmaceutical Compositions

The present invention further provides pharmaceutical compositions comprising antagonists (e.g. antibodies) that target a cancer stem cell marker. These pharmaceutical compositions find use in inhibiting tumor cell growth and treating cancer in human patients.

Formulations are prepared storage and use by combining a purified antagonist antibody) of the present invention with a pharmaceutically acceptable carrier, excipient, and/or stabilizer as a sterile lyophilized powder, aqueous solution, etc (Remington, The Science and Practice of Pharmacy 20th Edition Mack Publishing, 2000). Suitable carriers, excipients, or stabilizers comprise nontoxic buffers such as phosphate, citrate, and other organic acids; salts such as sodium chloride; antioxidants including ascorbic acid and methionine, preservatives octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN or polyethylene glycol (PEG).

The pharmaceutical composition of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular infection or infusion; or intracranial (e.g., intrathecal or intraventricular) administration.

The therapeutic formulation can be in unit dosage form. Such formulations include tablets, pills, capsules, powders, granules, solutions or suspensions in water or non-aqueous media, or suppositories for oral, parenteral, or rectal administration or for administration by inhalation. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and other diluents (e.g. water) to form a solid preformulation composition containing a homogeneous mixture of a compound of the present invention, or a non-toxic pharmaceutically acceptable salt thereof. The solid preformulation composition is then subdivided into unit dosage forms of the type described above. The tablets, pills, etc of the novel composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials including a number of polymeric acids and mixtures of polymeric acids with such materials as shellac, cetyl alcohol and cellulose acetate.

Pharmaceutical formulations include antagonists of the present invention complexed with liposomes (Epstein, et al., 1985, Proc. Natl. Acad. Sci. USA 82:3688; Hwang, et al., 1980, Proc. Natl. Acad. Sci. USA 77:4030; and U.S. Pat. Nos. 4,485,045 and 4,544,545). Liposomes with enhanced circulation time are disclosed in U.S. Pat. No. 5,013,556. Some liposomes can be generated by the reverse phase evaporation with a lipid composition comprising phosphatidylcholine, cholesterol, and PEG-derivatized phosphatidylethanolamine (PEG-PE). Liposomes are extruded through filters of defined pore size to yield liposomes with the desired diameter.

The antagonist can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions as described in Remington, The Science and Practice of Pharmacy 20th Ed. Mack Publishing (2000).

In addition sustained-release preparations can be prepared. Suitable examples of sustained-release preparations include semipermeable matrices of solid hydrophobic polymers containing the antibody, which matrices are in the form of shaped articles (e.g. films, or microcapsules). Examples of sustained-release matrices include polyesters, hydrogels such as poly(2-hydroxyethyl-methacrylate) or poly(vinylalcohol), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

Treatment with Antagonists

It is envisioned that the antagonists of the present invention can be used to treat various conditions characterized by expression and/or increased responsiveness of cells to a cancer stem cell marker. Particularly it is envisioned that the antagonists (e.g. antibodies) against a cancer stem cell marker will be used to treat proliferative disorders including but not limited to benign and malignant tumors of the kidney, liver, bladder, breast, stomach, ovary, colon, rectum, prostate, lung, vulva, thyroid, head and neck, brain (glioblastoma, astrocytoma, medulloblastoma, etc), blood and lymph (leukemias and lymphomas).

The antagonists are administered as an appropriate pharmaceutical composition to a human patient according with known methods. Suitable method of administration include intravenous administration as a bolus or by continuous infusion over a period of time, by intramuscular, intraperitoneal, intravenous, intracerobrospinal, subcutaneous, intraarticular, intrasynovial, intrathecal, oral, topical, or inhalation routes.

In some embodiments, the treatment involves the combined administration of an antagonist of the present invention and a chemotherapeutic agent or cocktail of multiple different chemotherapeutic agents. Treatment with an antagonist can occur prior to, concurrently with, or subsequent to administration of chemotherapies. Chemotherapies contemplated by the invention include chemical substances or drugs which are known in the art and are commercially available, such as Doxorubicin, 5-Fluorouracil, Cytosine arabinoside ("Ara-C"), Cyclophosphamide, Thiotepa, Busulfan, Cytoxin, Taxol, Methotrexate, Cisplatin, Melphalan, Vinblastine and Carboplatin. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically. Preparation and dosing schedules for such chemotherapy are also described in Chemotherapy Service Ed., M. C. Perry, Williams & Wilkins, Baltimore, Md. (1992).

In other embodiments, the treatment involves the combined administration of an antagonist of the present invention and radiation therapy. Treatment with an antagonist can occur prior to, concurrently with, or subsequent to administration of radiation therapy. Any dosing schedules for such radiation therapy can be used.

In other embodiments, the treatment can involve the combined administration of antibodies of the present invention with other antibodies against additional tumor associated antigens including, but not limited to, antibodies that bind to the EGF receptor (EGFR) (Erbitux®), the erbB2 receptor (HER2) (Herceptin®), and vascular endothelial growth factor (VEGF) (Avastin®). Furthermore, treatment can include administration of one or more cytokines, can be accompanied by surgical removal of cancer cells or any other therapy deemed necessary by a treating physician.

For the treatment of the disease, the appropriate dosage of an antagonist of the present invention depends on the type of disease to be treated, the severity and course of the disease, the responsiveness of the disease, whether the antagonist is administered for therapeutic or preventative purposes, previous therapy, patient's clinical history, and so on all at the discretion of the treating physician. The antagonist can be administered one time or over a series of treatments lasting from several days to several months, or until a cure is effected or a diminution of the disease state is achieved (e.g. reduction in tumor size). Optimal dosing schedules can be calculated from measurements of drug accumulation in the body of the patient and will vary depending on the relative potency of an individual antagonist. The administering physician can easily determine optimum dosages, dosing methodologies and repetition rates. In general, dosage is from 0.01 µg to 100 mg per kg of body weight, and can be given once or more daily, weekly, monthly or yearly. The treating physician can estimate repetition rates for dosing based on measured residence times and concentrations of the drug in bodily fluids or tissues.

Kits

In yet other embodiments, the present invention provides kits that can be used to perform the methods described herein. In some embodiments, a kit comprises an antibody or antibodies specific for a cancer stem cell marker, a purified antibody or antibodies, in one or more containers. In some embodiments, a kit further comprises a substantially isolated cancer stem cell marker polypeptide comprising an epitope that is specifically immunoreactive with the antibody or antibodies included in the kit, a control antibody that does not react with the cancer stem cell marker polypeptide, and/or a means for detecting the binding of an antibody to a cancer stem cell marker polypeptide (such as, for example, a fluorescent chromophore, an enzymatic substrate, a radioactive compound or a luminescent compound conjugated to the antibody against a cancer stem cell marker or to a second antibody that recognizes the antibody against a cancer stem cell marker). In other embodiments, a kit comprises reagents specific for the detection of mRNA or cDNA (e.g., oligonucleotide probes or primers) of one or more cancer stem cell marker. In some embodiments, the kits contain all of the components necessary and/or sufficient to perform a detection assay, including all controls, directions for performing assays, and any necessary software for analysis and presentation of results.

A compartment kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies or probes used in the methods, containers which contain wash reagents (such as phosphate buffered saline, Tris-buffers, etc.), and containers which contain the reagents used to detect the bound antibody or probe. One will readily recognize that the disclosed polynucleotides, polypeptides and antibodies of the present invention can be readily incorporated into one of the established kit formats which are well known in the art.

Screening Methods

In certain embodiments, the present invention provides a method of identifying a molecule that binds to a non-ligand binding region of an extracellular domain of a human NOTCH receptor and inhibits growth of tumor cells, the method comprising: i) incubating the molecule with the non-ligand binding domain of the extracellular domain of the human Notch receptor; ii) determining if the molecule binds to the non-ligand binding region of the extracellular domain of the human Notch receptor; and iii) determining if the molecule inhibits growth of tumor cells. Molecules that specifically bind a non-ligand binding region of an extracellular domain of a human NOTCH receptor include, but are not limited to, small organic molecules, polypeptides, and antibodies.

Screening can be performed using any suitable method known in the art. In certain embodiments, screening is performed in vitro. In some embodiments, cells expressing a non-ligand binding region of the extracellular domain of a human NOTCH receptor are incubated with a labeled molecule and specific binding of the labeled molecule to a non-ligand binding region of the extracellular domain of a human NOTCH receptor is determined by FACS analysis. In some embodiments, a non-ligand binding region of the extracellular domain of a human NOTCH receptor is expressed by phage display, and molecules that specifically binding to a non-binding region of the extracellular domain of a human NOTCH receptor are identified. Other suitable methods for identifying molecules that specifically bind to a non-ligand binding region of a human NOTCH receptor include, but are not limited to, ELISA; Western (or immuno) blotting; and yeast-two-hybrid.

Molecules that specifically bind to a non-ligand binding region of an extracellular domain of a human NOTCH receptor are then tested for inhibition of tumor cell growth. Testing can be performed using any suitable method known in the art. In certain embodiments, molecules that specifically bind to non-ligand binding region of the extracellular domain of a human NOTCH receptor are tested for the ability to inhibit tumor growth in vitro. In some embodiments, molecules that specifically bind a non-ligand binding region of the extracellular domain of a human NOTCH receptor are incubate d with tumor cells in culture and proliferation of tumor cells in the presence of a molecule that specifically binds a non-ligand binding region of the extracellular domain of a human NOTCH receptor is determined and compared to tumor cells incubated with a non-binding control molecule. In certain embodiments, molecules that specifically bind to non-ligand binding region of the extracellular domain of a human NOTCH receptor are tested for the ability to inhibit tumor growth in vivo. In certain embodiments, molecules that specifically bind a non-ligand binding region of the extracellular domain of a human NOTCH receptor are injected into an animal xenograft model and the growth of tumors in animals treated with molecules that specifically bind to non-ligand binding region of the extracellular domain of a human NOTCH receptor is determined and compared to animals treated with a non-binding control molecule.

EXAMPLES

Example 1

Production of Antibodies

Antigen Production

Antibodies were generated against the non-ligand binding region of NOTCH1 find NOTCH2.

In certain embodiments, recombinant polypeptide fragments of the human NOTCH1 extracellular domain were generated as antigens for antibody production. Standard recombinant DNA technology was used to isolate polynucleotides encoding amino acids 1-220 of NOTCH1 (SEQ ID NO: 1) and amino acids 1427-1563 of NOTCH1 (SEQ ID NO: 18). These polynucleotides were separately ligated in-frame N-terminal to a human Fe and histidine-tag and cloned into a transfer plasmid vector for baculovirus mediated expression in insect cells. Standard transfection, infection, and cell culture protocols were used to produce recombinant insect cells expressing the corresponding NOTCH1 polypeptides corresponding to EGF repeats 1-5 (SEQ ID NO: 2) and EGF repeats 10-15 (SEQ ID NO: 19) (O'Reilley et al., Baculovirus expression vectors: A Laboratory Manual, Oxford: Oxford University Press (1994)).

Cleavage of the endogenous NOTCH1 signal sequence was approximated using cleavage prediction software SignalP 3.0 at between amino acid 18 and 19, however the actual in vivo cleavage point can differ by a couple of amino acids either direction. Thus NOTCH1 antigen protein corresponding to FOE repeats 1-5 comprises approximately amino acid 19 through amino acid 220 (SEQ ID NO: 3). Antigen protein was purified from insect cell lysates using protein A and Ni++-chelate affinity chromatography. Purified antigen protein was dialyzed against PBS (pH=7), concentrated to approximately 1 mg/ml, and sterile filtered in preparation for immunization.

In certain embodiments, recombinant polypeptide fragments of the human NOTCH2 extracellular domain were generated as antigens for antibody production Standard recombinant DNA technology was used to isolate a polynucleotide encoding amino acids 1-493 of Notch2 (SEQ ID NO: 1). This polynucleotide was ligated in-frame N-terminal to either a human Fc-tag or histidine-tag and cloned into a transfer plasmid vector for baculovirus mediated expression in insect cells. Standard transfection, infection, and cell culture protocols were used to produce recombinant insect cells expressing the corresponding Notch2 polypeptide (O'Reilley et al., Baculovirus expression vectors: A Laboratory Manual, Oxford: Oxford University Press (1994)).

Cleavage of the endogenous signal sequence of human Notch2 was approximated using cleavage prediction software SignalP 3.0, however the actual in vivo cleavage point can differ by a couple of amino acids either direction. The predicated cleavage of Notch2 is between amino acids 1 and 26, thus Notch2 antigen protein comprises approximately amino acid 27 through amino acid 493. Antigen protein was purified from insect cell conditioned medium using Protein A and $Ni^{++}$-chelate affinity chromatography. Purified antigen protein was then dialyzed against PBS (pH=7), concentrated to approximately 1 mg/ml, and sterile filtered in preparation for immunization.

Immunization

Mice (n=3) were immunized with purified NOTCH1 or NOTCH2 antigen protein (Antibody Solutions; Mountain View, Calif.) using standard techniques. Blood from individual mice was screened approximately 70 days after initial immunization for antigen recognition using ELISA and FACS analysis (described in detail below). The two animals with the highest antibody titers were selected for final antigen boost after which spleen cells were isolated for hybridoma production. Hybridoma cells were plated at 1 cell per well in 96 well plates, and the supernatant from each well screened by ELISA and FACS analysis against antigen protein. Several hybridomas with high antibody titer were selected and scaled up in static flask culture. Antibodies were purified from the hybridoma supernatant using protein A or protein G agarose chromatography and antibodies were tested by FACS as described below. Several anti-NOTCH1 antibodies were isolated including 13M57 (also referred to as 13M30) from animals immunized with NOTCH1 antigen corresponding to EGF repeats 1-5 and 31M80, 31M103, 31M106, and 31M108 from animals immunized with NOTCH1 antigen corresponding to EGF repeats 10-15. The nucleotide and predicted protein sequences of both the heavy chain (SEQ ID NO: 4-5) and light chain (SEQ ID NO: 6-7) of antibody 13M57 were determined. A NOTCH2 antibody, 59M07 (ATCC deposit no PTA-10634; hybridoma deposited on Feb. 4, 2010 at American Type Culture Collection, 10801 University Boulevard, Manassas, Va. 20110-2209), was generated that specifically binds to EGF repeat 2.

Epitope Mapping

To identify antibodies that recognize specific non-ligand binding regions of the NOTCH receptor extracellular domains, epitope mapping was preformed. In certain embodiments, mammalian expression plasmid vectors comprising a CMV promoter upstream of polynucleotides that encode fragments of the extracellular NOTCH1 domain as Fe fusion proteins were generated using standard recombinant DNA technology. These fusion proteins included a series of NOTCH1 fragments containing a nested series of deletions of EGF domains 1-5 or 10-15. Recombinant proteins were then expressed in cultured mammalian cells by transient transfection. Twenty-four to 48 hours following transfection, cells were harvested and cell lysate protein separated on non-reducing SDS-PAGE acrylamide gels for Western blotting using antibodies from mice immunized with NOTCH1 antigen. As shown in FIGS. 1A and B monoclonal antibody 13M57 recognized an epitope contained within EGF repeat 4 (SEQ ID NO: 8) with a $K_D$ of 0.2 nM. Monoclonal antibody 31M80 recognized an epitope within EGF repeat 13 (FIG. 1C). Antibodies 31M103 ($K_D$=0.2 nM), 31M106 ($K_D$=3 nM), and 31M108 ($K_D$=0.2 nM) also recognize an epitope within EGF13 of Notch1. All antibody affinities were determined by BIAcore.

To identify specific epitopes within the extracellular domains recognized by an antibody against NOTCH1 the SPOTs system is used (Sigma Genosys, The Woodlands, Tex.). A series of 10-residue linear peptides overlapping by one amino acid and covering the entire NOTCH1 extracellular domain are synthesized and covalently bound to a cellulose membrane by the SPOT synthesis technique. The membrane is preincubated for 8 hours at room temperature with blocking buffer and hybridized with antibody overnight at 4° C. The membrane is then washed, incubated with a secondary antibody conjugated to horseradish peroxidase (HRP) (Amersham Bioscience, Piscataway, N.J.), re-washed, and visualized with signal development solution containing 3-amino-9-ethylcarbazole. Specific epitopes recognized by an antibody are thus determined.

FACS Analysis

Figure 2A:
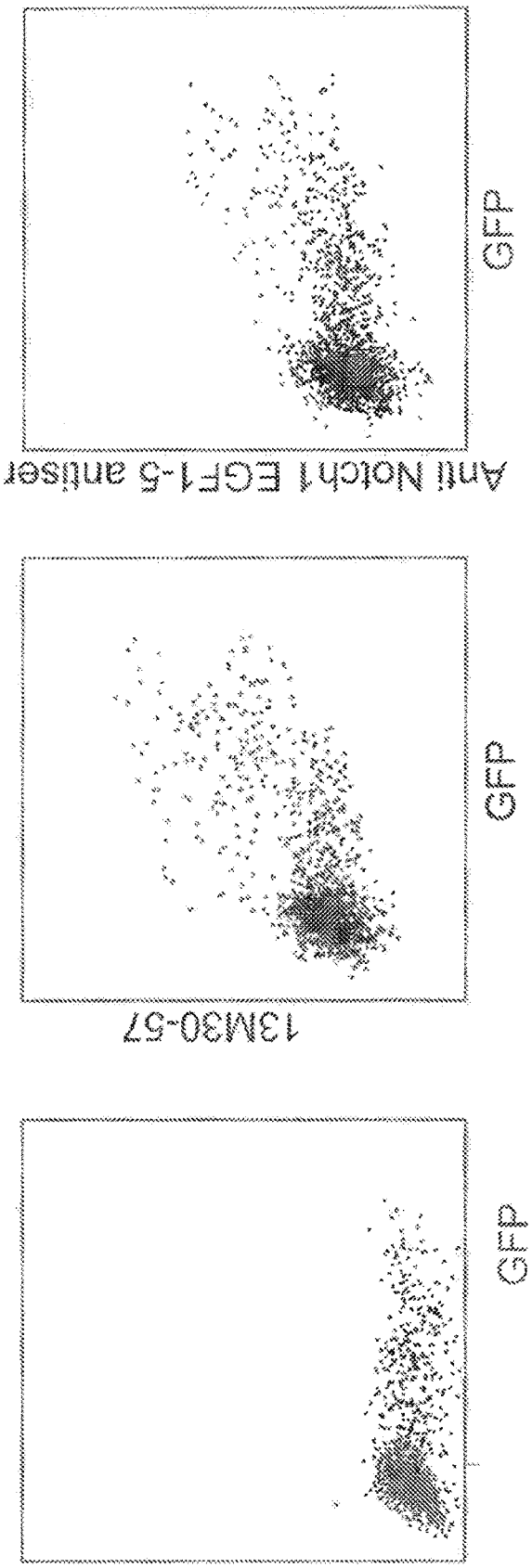

To select monoclonal antibodies produced by hybridoma clones that recognize native cell-surface NOTCH1 protein, FACs analysis was used. To facilitate the screening of cells by FACS, an isotype control mouse IgG1κ antibody and anti-NOTCH1 monoclonal antibody clones 13M57 and 31M80 were conjugated to Alexa Fluor™ 647 (AF647) using invitrogen kit #A-20186. The conjugation reaction resulted in approximately 0.1 of AF647-labeled anti-Notch1 antibody at 1.0 mg/mL and AF647-labeled isotype control antibody at approximately 0.5 mg/mL. HEK293 cells were transiently transfected with expression vectors encoding full length NOTCH1 and GFP. Twenty-four to 48-hours post-transfection cells were collected in suspension and incubated on ice with either anti-NOTCH1 13M57 antibody, the corresponding anti-human NOTCH1 antisera, or control IgG1 antibodies to detect background antibody binding. The cells were washed and then sorted by FACS to identify antibody binding to cell surface expressed NOTCH1. Anti-NOTCH1 antibody 13M57 recognizes cell-surface NOTCH1 on HEK 293 cells (FIG. 2A). Similarly, anti-NOTCH1 antibody 31M80 specifically recognizes HEK 293 cells transfected with NOTCH1 receptor but not untransfected cells, and this binding is blocked by increasing amounts of antigen protein containing NOTCH EGF repeats 10-16 linked to human Fc (Ag31) but not antigen protein containing EGF repeats 1-5 linked to Fc (Ag13) (FIG. 2B).

Figure 2D:
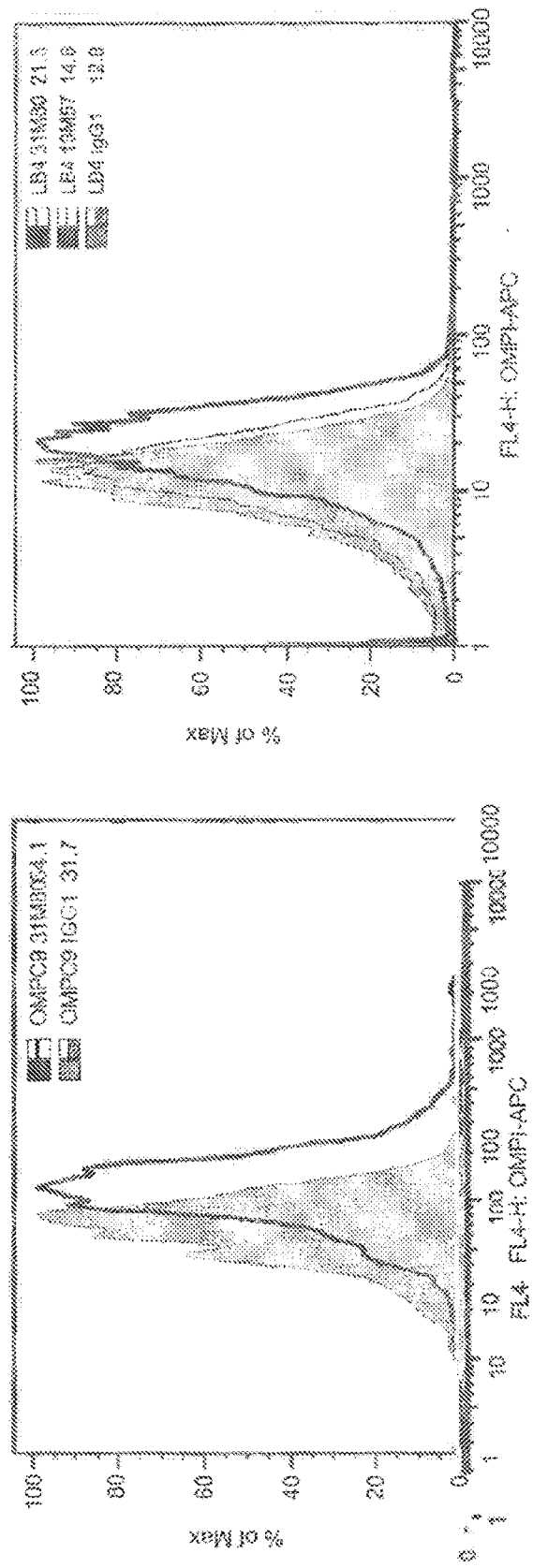

To determine if anti-NOTCH1 antibodies recognize NOTCH1 receptor protein on tumor cells, dissociated tumor cells were analyzed by FACS. Dissociated breast tumor cells were incubated with anti-ESA, anti-CD44, and anti-NOTCH1 antibodies. Both 3M57 and 31M80 antibodies showed increased binding to cells from two different breast tumors (PE13 and T3) compared to an isotype antibody control (FIG. 2C). Furthermore, these breast tumor cells expressed high levels of ESA and CD44 suggesting that both antibodies recognize NOTCH1 receptor on cancer stem cells (FIG. 2C). Anti-NOTCH1 receptor antibody 31M80 also showed increased binding to dissociated colon tumor cells from two different patients (FIG. 2D).

To determine whether NOTCH1 expression levels are directly associated with the tumorigenic activity of ESA+ CD44+ cells, subpopulations of PE13 cells were isolated by FACS based on 31M180-AF647 and CD44–PECy7 staining (FIG. 2C). Isolated cells are then injected into mice and their tumorigenicity, the number of injected cells required for consistent tumor formation, is determined in comparison with ESA+CD44+NOTCH1$^{low}$ and CD44− tumor cells.

Chimeric Antibodies

After monoclonal antibodies that specifically recognize a non-ligand binding domain of a NOTCH receptor are identified, these antibodies are modified to overcome the human anti-mouse antibody (HAMA) immune response when rodent antibodies are used as therapeutics agents. The variable regions of the heavy-chain and light-chain of the selected monoclonal antibody are isolated by RT-PCR from hybridoma cells and ligated in-frame to human IgG1 heavy-chain and kappa light chain constant regions, respectively, in mammalian expression vectors. Alternatively a human Ig expression vector such as TCAE 5.3 is used that contains the human IgG1 heavy-chain and kappa light-chain constant region genes on the same plasmid (Preston et al., 1998, Infection & Immunity 66:4137-42). Expression vectors encoding chimeric heavy- and light-chains are then co-transfected into Chinese hamster ovary (CHO) cells for chimeric antibody production. Immunoreactivity and affinity of chimeric antibodies are compared to parental murine antibodies by ELISA and FACS.

Humanized Antibodies

As chimeric antibody therapeutics are still frequently antigenic, producing a human anti-chimeric antibody (HACA) immune response, chimeric antibodies against a NOTCH1 receptor can require further humanization. To generate humanized antibodies the three short hypervariable sequences, or complementary determining regions (CDRs), of the chimeric antibody heavy- and light-chain variable domains described above are engineered using recombinant DNA technology into the variable domain framework of a human heavy- and light-chain sequences, respectively, and then cloned into a mammalian expression vector for expression in CHO cells. The immunoreactivity and affinity of the humanized antibodies are compared to parental chimeric antibodies by ELISA and FACS. Additionally, site-directed or high-density mutagenesis of the variable region can be used to optimize specificity, affinity, etc. of the humanized antibody.

Human Antibodies

In alternative embodiments, human antibodies that specifically recognize the non-ligand, extracellular domain of a NOTCH receptor are isolated using phage display technology. A synthetic antibody library containing human antibody variable domains (MorphoSys, Munich, Germany) is screened for specific and high affinity recognition of a NOTCH receptor antigen described above. CDR cassettes in the library are specifically exchanged via unique flanking restriction sites for antibody optimization. Optimized human variable regions are then cloned into an Ig expression vector containing human IgG1 heavy-chain and kappa light-chain for expression of human antibodies in CHO cells.

Example 2

In Vitro Assays to Evaluate Antibodies Against a NOTCH1 Receptor

This example describes methods for in vitro assays to test the activity of antibodies generated against a NOTCH1 receptor on cell proliferation and cytotoxicity.

Ligand Binding

Antibodies against NOTCH1 were tested for their ability to block ligand binding of the NOTCH receptor ligands DLL4 and JAGGED1 (JAG1). HEK 293 cells stably transfected with a full-length NOTCH1 cDNA were incubated with either DLL4-Fc or JAG1-Fc in the presence of anti-NOTCH1 antibodies (13M57, 31M103, 31M106, or 31M108) or control anti-DLL4 (21M18) or anti-JAG1 (64M14) antibodies Binding of Fc fusion proteins to cells expressing NOTCH1 was detected by PE-conjugated goat anti-Fc antibody and flow cytometry.

Anti-NOTCH1 antibodies against EGF13 fail to effectively block ligand binding (FIG. 3). Anti-DLL4 or anti-JAG1 antibody inhibition of DLL4 or JAG1 binding to the NOTCH1 receptor, respectively, was compared to inhibition by anti-NOTCH1 antibodies. Anti-NOTCH1 antibodies 31M103, 31M106, and 31M108, all of which specifically bind to EGF13, only partially inhibit ligand binding. 31M108 showed between 50-75% inhibition compared to the ligand antibodies. Similarly, 31M103 and 31M106 showed only between 25-50% inhibition.

Anti-NOTCH1 antibodies against EGF4 do no block ligand binding (FIG. 3). Again, anti-DLL4 or anti-JAG1 antibody inhibition of DLL4 or JAG1 binding to NOTCH1 was compared to inhibition by the anti-NOTCH1 antibodies 13M57, which specifically bind to EGF4. 13M57 showed no inhibition of ligand binding when compared to inhibition by anti-DLL4 or anti-JAG1 antibodies.

Proliferation Assay

Antibodies against NOTCH1 were tested for their effect on tumor cell growth in vitro using a BrdU based assay. Freshly dissociated, Lin-depleted breast tumor cells were cultured in low oxygen for between 2-5 days. Cells were then cultured at 20,000 cells/well with 2.5 ug/mL or 5.0 ug/mL anti-NOTCH1 (13M57), control non-specific murine IgG, or no antibody for three days followed by 18 hours BrdU labeling. All experiments are performed with 5 replicates. The ability of anti-NOTCH1 antibodies to inhibit cell proliferation compared to control antibodies is shown in FIG. 4.

Complement-Dependent Cytotoxicity Assay

Cancer cell lines expressing a NOTCH1 receptor or, alternatively, cancer stem cells isolated from a patients sample passaged as a xenograft in immunocompromised mice (described in detail below) are used to measure complement dependent cytotoxicity (CDC) mediated by an antibody against a NOTCH1 receptor. Cells are suspended in 200 ul RPMI 1640 culture medium supplemented with antibiotics and 5% FBS at 106 cells/ml. Suspended cells are then mixed with 200 ul serum or heat-inactivated serum with antibodies against a NOTCH1 receptor or control antibodies in triplicate. Cell mixtures are incubated for 1 to 4 hours at 37° C. in 5% CO2. Treated cells are then collected, resuspended in 100 ul FITC-labeled annexin V diluted in culture medium and incubated at room temperature for 10 min. One hundred ul of a propidium iodide solution (25 ug/ml) diluted in HBSS is added and incubated for 5 min at room temperature. Cells are collected, resuspended in culture medium and analyzed by flow cytometry. Flow cytometry of FITC stained cells provides total cell counts, and propidium iodide uptake by dead cells as a percentage of total cell numbers is used to measure cell death in the presence of serum and antibodies against a NOTCH1 compared to heat-inactivated serum and control antibodies. The ability of anti-NOTCH1 antibodies to mediated complement-dependent cytotoxicity is thus determined.

Antibody-Dependent Cellular Cytotoxicity Assay

Cancer cell lines expressing a NOTCH1 receptor or, alternatively, cancer stem cells isolated from a patients sample passaged as a xenograft immunocompromised mice (described in detail below) are used to measure antibody dependent cellular cytotoxicity (ADCC) mediated by an antibody against a NOTCH1 receptor. Cells are suspended in 200 ul phenol red-free RPMI 1640 culture medium supplemented with antibiotics and 5% FBS at 106 cells/ml. Peripheral blood mononuclear cells (PBMCs) are isolated from heparinized peripheral blood by Ficoll-Paque density gradient centrifugation for use as effector cells. Target cells (T) are then mixed with PBMC effector cells (E) at E/T ratios of 25:1, 10:1 and 5:1 in 96-well plates in the presence of a NOTCH1 receptor or control antibodies. Controls include incubation of target cells alone and effector cells alone in the presence of antibody. Cell mixtures are incubated for 1 to 6 hours at 37° C. in 5% CO2. Released lactate dehydrogenase (LDH), a stable cytosolic enzyme released upon cell lysis, is then measured by a colorimetric assay (CytoTox96 Non-radioactive Cytotoxicity Assay; Promega; Madison, Wis.). Absorbance data at 490 are collected with a standard 96-well plate reader and background corrected. The percentage of specific cytotoxicity is calculated according to the formula: % cytotoxicity=100×(experimental LDH release−effector spontaneous LDH release−target spontaneous LDH release)/(target maximal LDH release−target spontaneous LDH release). The ability of antibodies against a NOTCH1 receptor to mediated antibody dependent cellular cytotoxicity is thus determined.

Example 3

In Vivo Prevention of Tumor Growth Using Non-Ligand Binding Region Anti-NOTCH Receptor Antibodies This example describes the use of anti-NOTCH1 and anti-NOTCH2 receptor antibodies against a non-ligand binding region to prevent tumor growth in a xenograft model.

Tumor cells from a patient sample UM-PE13, OMP-C9, OMP-C8, and OMP-C6 that have been passaged as a xenograft in mice were prepared for injection into experimental animals. Tumor tissue was removed under sterile conditions, cut up into small pieces, minced completely using sterile blades, and single cell suspensions obtained by enzymatic digestion and mechanical disruption. The resulting tumor pieces were mixed with ultra-pure collagenase III in culture medium (200-250 units of collagenase per mL) and incubated at 37° C. for 3-4 hours with pipetting up and down through a 10-mL pipette every 15-20 min. Digested cells were filtered through a 45 ul nylon mesh, washed with RPMI/20% FBS, and washed twice with HBSS. Dissociated tumor cells were then injected subcutaneously into NOD/SCID mice at 6-8 weeks to elicit tumor growth. For UM-PE13 breast tumor cells, 50,000 cells in 100 ul were injected into the right mammary fat pad (n=20) along with the implantation of an estrogen pellet. For OMP-C9 colon tumor cells, 50,000 cells in 100 ul were injected into the right flank region (n=20). For OMP-C8 colon tumor cells, 10,000 cells in 100 ul were injected into the right flank area (n=10). For OMP-C6 colon tumor cells, 10,000 cells in 100 ul were injected into the right flank (n 10).

In alternative embodiments, dissociated tumor cells are first sorted into tumorigenic and non-tumorigenic cells based on cell surface markers before injection into experimental animals. Specifically, tumor cells dissociated as described above are washed twice with Hepes buffered saline solution (HBSS) containing 2% heat-inactivated calf serum (HICS) and resuspended at 106 cells per 100 ul. Antibodies are added and the cells incubated for 20 min on ice followed by two washes with HBSS/2% HICS. Antibodies include anti- ESA (Biomeda, Foster City, Calif.), anti-CD44, anti-CD24, and Lineage markers anti-CD2, -CD3, -CD10, -CD16, -CD18, -CD31, -CD64, and -CD140b (collectively referred to as Lin; PharMingen, San Jose, Calif.). Antibodies are directly conjugated to fluorochromes to positively or negatively select cells expressing these markers. Mouse cells are eliminated by selecting against H2Kd+ cells, and dead cells are eliminated by using the viability dye 7AAD. Flow cytometry is performed on a FACSVantage (Becton Dickinson, Franklin Lakes, N.J.). Side scatter and forward scatter profiles are used to eliminate cell clumps. Isolated ESA+, CD44+, CD24−/low, Lin-tumorigenic cells are then injected subcutaneously into NOD/SCID mice to elicit tumor growth.

Three days after tumor cell injection, antibody treatment was commenced. Each injected animal received 10 mg/kg anti-NOTCH1 antibodies or PBS as a control intraperitoneal (i.p.) two times per week for a total of 6 to 8 weeks. Animals injected with UM-PE13 cells received injections into the right upper mammary fat pad in addition to estrogen pellet injections. Animals injected with OMP-C9, OMP-C8, or UM-C6 cells received injections in the right lower quadrant of the abdomen. Tumor size was assessed twice a week. Animals treated with anti-NOTCH1 13M57 antibodies had significantly reduced PE-13 breast tumor cell growth (FIG. 5) and significantly reduced OMP-C9 colon tumor cell growth (FIG. 6A) compared to PBS injected controls. Animals treated with anti-NOTCH1 13M57, 31M103, or 31M106 antibodies had significantly reduced OMP-C8 colon tumor cell growth (FIG. 6B) compared to controls. Further experimentation has indicated some variability in the effect of anti-NOTCH1 13M57 antibodies in reducing OMP-C9 tumor cell growth in NOD/SCID mice.

Injection of PE-13 cells expressing luciferase under the control of a strong, constitutive promoter allows sensitive and accurate in vivo detection of tumor growth during the course of treatment. Animals are injected with luciferin, which is converted by the luciferase enzyme to produce light that can be imaged through the skin. Treatment with 13M30 (13M57) antibodies significantly reduced growth of luciferase expressing PE-13 tumor cells compared to treatment with PBS or control antibodies (FIG. 7).

In certain embodiments, the anti-NOTCH2 antibody 59M07 was administered at 10 mg/kg 2 days after C6 tumor cell injection. Antibody was given twice weekly for a total of 48 days. Treatment with 59M07 significantly reduced colon tumor cell growth (FIG. 8).

Example 4

Production of Antibodies Against NOTCH1, NOTCH2, NOTCH3, and NOTCH4 EGF Repeat 4

Identification of an antibody against the fourth EGF repeat of NOTCH1 that reduces tumor growth in animals suggests the importance of the non-ligand domain, and the fourth EGF repeat in particular, for effective cancer therapies. To target the EGF repeat 4 in other Notch receptor family members, antibodies against NOTCH2, NOTCH3, and NOTCH4 EGF repeat 4 are produced and analyzed as described above for anti-NOTCH1 13M57. Specifically, mice are immunized with antigens comprising the fourth EGF repeat of NOTCH2 (SEQ ID NO: 9); NOTCH3 (SEQ ID NO: 10), or NOTCH4 (SEQ ID NO: 11). Antibodies that recognize specific Notch receptors as well as recognize different combinations of the four Notch receptors are identified using FACS analysis of HEK 293 cells transfected with each Notch receptor as described in detail above. Antibodies that recognize the fourth EGF repeat of two Notch receptor family members are envisioned (e.g. antibodies that recognize the fourth EGF repeat of NOTCH1 and NOTCH2; NOTCH1 and NOTCH3; NOTCH1 and NOTCH4; NOTCH2 and NOTCH3; NOTCH2 and NOTCH4; or NOTCH3 and NOTCH4). Antibodies that recognize the fourth EGF repeat of three Notch receptor family members are envisioned (e.g. antibodies that recognize the fourth EGF repeat of NOTCH1, NOTCH2, and NOTCH3; NOTCH1, NOTCH2, and NOTCH4; or NOTCH2, NOTCH3, and NOTCH4). And antibodies that recognize the fourth EGF repeat of four Notch receptor family members are envisioned (e.g. antibodies that recognize the fourth EGF repeat of NOTCH1, NOTCH2, NOTCH3 and NOTCH4).

Example 5

In Vivo Treatment of Tumors Using Anti-NOTCH1 Receptor Antibodies

This example describes the use of anti-NOTCH1 receptor antibodies to treat cancer in a xenograft model.

Tumor cells from a patient sample (solid tumor biopsy or pleural effusion) that have been passaged as a xenograft in mice are prepared for repassaging into experimental animals. Tumor tissue is removed, cut up into small pieces, minced completely using sterile blades, and single cell suspensions obtained by enzymatic digestion and mechanical disruption. Dissociated tumor cells are then injected subcutaneously either into the mammary fat pads, for breast tumors, or into the flank, for non-breast tumors, of NOD/SCID mice to elicit tumor growth. Alternatively, ESA+, CD44+, CD24−/low, Lin-tumorigenic tumor cells are isolated as described in detail above and injected.

Following tumor cell injection, animals are monitored for tumor growth. Once tumors reach an average size of approximately 150 to 200 rum, antibody treatment begins. Each animal receives 100 ug NOTCH1 receptor antibodies or control antibodies i.p. two to five times per week for a total of 6 weeks. Tumor size is assessed twice a week during these 6 weeks. The ability of NOTCH1 receptor antibodies to prevent further tumor growth or to reduce tumor size compared to control antibodies is thus determined.

At the end point of antibody treatment, tumors are harvested for further analysis. In some embodiments, a portion of the tumor is analyzed by immunofluorescence to assess antibody penetration into the tumor and tumor response. A portion of each harvested tumor from anti-NOTCH1 receptor treated and control antibody treated mice is fresh-frozen in liquid nitrogen, embedded in O.C.T., and cut on a cryostat as 10 urn sections onto glass slides. Alternatively a portion of each tumor is formalin-fixed, paraffin-embedded and cut on a microtome as 10 um section onto glass slides. Sections are post-fixed and incubated with chromophore labeled antibodies that specifically recognize injected antibodies to detect anti-NOTCH1 receptor or control antibodies present in the tumor biopsy. Furthermore antibodies that detect different tumor and tumor recruited cell types such as, for example, anti-VE cadherin (CD144) or anti-PECAN-1 (CD31) antibodies to detect vascular endothelial cells, anti-smooth muscle alpha-actin antibodies detect vascular smooth muscle cells, anti-Ki67 antibodies to detect proliferating cells, TUNEL assays to detect dying cells, and anti-intracellular domain (ICD) Notch fragment antibodies to detect Notch signaling can be used to assess affects of antibody treatment on angiogenesis, tumor growth and tumor morphology.

The effect of anti-NOTCH1 receptor antibody treatment on tumor cell gene expression is also assessed. Total RNA is extracted from a portion of each harvested tumor from NOTCH1 antibody treated and control antibody treated mice and used for quantitative RT-PCR. Expression levels of NOTCH1, components of Notch signaling pathway including, as well as addition cancer stem cell markers previously identified including, for example, CD44 are analyzed relative to the house-keeping gene GAPDH as an internal control. Changes in tumor cell gene expression upon NOTCH1 receptor antibody treatment are thus determined.

In addition, the effect of anti-NOTCH1 receptor antibody treatment on the presence of cancer stem cells in a tumor is assessed. Tumor samples from NOTCH1 versus control antibody treated mice are cut up into small pieces, minced completely using sterile blades, and single cell suspensions obtained by enzymatic digestion and mechanical disruption. Dissociated tumor cells are then analyzed by FACS analysis for the presence of tumorigenic cancer stem cells based on ESA+, CD44+, CD24−/low, Lin-surface cell marker expression as described in detail above.

The tumorigenicity of cells isolated based on ESA+, CD44+, CD24−/low, Lin-expression following anti-NOTCH1 antibody treatment can then assessed. 5,000, 1,000, 500, and 100 isolated ESA+CD44+, CD24−/low, Lin-cancer stem cells from NOTCH1 antibody treated versus control antibody treated mice are re-injected subcutaneously into the mammary fat pads of NOD/SCID mice. The tumorigenicity of cancer stein cells based on the number of injected cells required for consistent tumor formation is thus determined.

Example 6

In Vivo Treatment of Tumors Using Combination Therapy: Anti-NOTCH1 Receptor Antibodies and Chemotherapy This example describes methods of treating cancer using combination therapy. Specifically anti-NOTCH1 antibodies in combination with chemotherapy treatment were used to treat both initial and established tumor growth in a xenograft model.

In certain embodiments, breast tumor cells were treated with a combination of anti-NOTCH1 antibodies and the chemotherapeutic, paclitaxel. Tumor cells from a patient sample UM-PE13 that have been passaged as a xenograft in mice were prepared for injection into experimental animals as described above. Dissociated UM-PE13 tumor cells (50,000 per animal) were injected subcutaneously into the right mammary fat pad of NOD/SCID mice along with the implantation of an estrogen pellet Tumors were allowed to grow for twenty-four days after which the tumors were measured and animals were split into four groups (n=10), each with an average tumor volume of 130 mm$^3$. Each of the four groups was treated as follows for 4 weeks: Group 1: paclitaxel; Group 2: paclitaxel; Group 3 paclitaxel+13M57; and Group 4: paclitaxel+13M57. All injections were administered IP, 2× per week. Paclitaxel was dosed at 15 mg/kg and 13M57 was dosed at 30 mg/kg. Treatments with paclitaxel or paclitaxel 13M57 were stopped at day 52 after the tumors had regressed and were undetectable. The animals were then treated as follows: Group 1: PBS; Group 2: 13M57; Group 3: PBS; and Group 4: 13M57. Tumor volume was checked once per week for the remainder of the experiment.

As shown in FIG. 9, concurrent combination treatment (paclitaxel+13M57) followed by continual treatment with anti-NOTCH1 13M57 antibodies had the greatest effect on tumor reoccurrence. Specifically, animals in Group 4 that were treated with a combination of paclitaxel and 13M57 for four weeks followed by continual treatment with 13M57 alone showed minimal tumor regrowth forty days following the termination of paclitaxel treatment (FIG. 9A). Only one animal in Group 4 showed appreciable tumor regrowth (FIG. 9B). Similarly, combination treatment in which paclitaxel treatment was administered prior to 13M57 treatment (Group 2) also showed significant reduction in tumor regrowth compared to animals treated with paclitaxel alone (Group 1), the latter of which showed tumor reoccurrence reaching tumor volumes near 100 mm$^3$. And finally, combination therapy-without continued treatment with anti-Notch 13M57 antibodies (Group 3) also showed significant efficacy in reducing tumor regrowth compared to paclitaxel treatment alone (FIG. 9).

In certain embodiments, colon tumor cells were treated with a combination of anti-NOTCH1 antibodies and the chemotherapeutic, irinotecan. Tumor cells from the patient sample OMP-C8 passaged as a xenograft in mice were prepared for injection into experimental animals as described above. Dissociated OMP-C8 cells (20,000 cells per animal) were injected into NOD/SOD mice in the right lower quadrant of the abdomen. 2 days after cell injection, animals were treated either with 7.5 mg/kg irinotecan alone (n=10) or with 10 mg/kg of the anti-NOTCH1 antibody 13M57 plus 7.5 mg/kg irinotecan 10). Animals received treatment two per week for up to 56 days, and tumor volume was assessed twice weekly.

As shown in FIG. 10, concurrent combination treatment of irinotecan plus 13M57 prevented colon tumor growth during treatment and also maintained tumor cells in this non-proliferative state for up to thirty days following the cessation of treatment. Nearly all animals treated with irinotecan alone showed growth of tumors during the treatment phase, after which tumors continued to grow until termination of the experiment (FIG. 10A). In contrast, animals treated with 13M57 plus irinotecan showed little to no tumor growth during combination treatment (FIG. 10B). Furthermore, tumor cells remained quiescent post-treatment, with only two animals showing tumor growth nearly thirty days (FIG. 10B).

In certain embodiments, colon tumor cells were treated with a combination of anti-NOTCH1 antibodies and the chemotherapeutic agent, oxaliplatin. Tumor cells from the patient sample OMP-C8 were prepared for injection into experimental animals as described above. Dissociated OMP-C8 cells (20,000 cells per animal) were injected into NOD/SCID mice in the right lower quadrant of the abdomen and were allowed to grow until they reached an average tumor volume of 200 mm$^3$. Animals (n=10 per experimental group) were treated either with oxaliplatin (7.5 mg/kg), 10 mg/kg 13M57, a combination of oxaliplatin and 13M57, or a control antibody. Treatment was given twice weekly for 22 days; tumor volume was assessed twice weekly.

As shown in FIG. 11, combination treatment was more effective inhibiting established tumor growth than oxaliplatin or 13M57 treatment alone. Treatment with either anti-NOTCH1 13M57 or oxaliplatin significantly reduced tumor growth (p=0.04 vs. control), but combination treatment further reduced growth compared to treatment with either agent alone (p=0.03 vs. single agent) (FIG. 11).

Example 7

In Vivo Treatment of Tumors Using Combination Therapy: Anti-NOTCH1 and Anti-NOTCH2 Receptor Antibodies This example describes methods of treating cancer using combination antibody therapy. In certain embodiments, breast tumor cells were treated with a combination of anti-NOTCH1 and anti-NOTCH2 antibodies. Tumor cells from the patient sample UM-PE13 expressing luciferase under the control of a strong, constitutive promoter were prepared for injection into experimental animals as described above. Dissociated PE13 tumor cells (50,000 per animal) were injected subcutaneously into the right mammary fat pad of NOD/SCID mice along with an estrogen pellet. Two days following cell injection, animals were treated either with 10 mg/kg anti-NOTCH1 31M108, 10 mg/kg 59M07 anti-NOTCH2, a combination of anti-NOTCH1 and NOTCH2 antibodies, or a control antibody (n=8-10 for each experimental group). Prior to imaging bioluminescence, animals were injected with luciferin; luciferin is converted by the luciferase enzyme to light that can be imaged through the skin. Animals were imaged and tumor volume was assessed twice weekly.

As shown in FIG. 12, treatment with a combination of NOTCH receptor antibodies has a significant effect on breast tumor cell growth. Treatment with 13M108 or 59M07 antibodies alone showed only a slight reduction in breast tumor growth (FIG. 12A). In contrast, combination treatment with anti-NOTCH1 and anti-NOTCH2 antibodies significantly reduced growth of luciferase expressing PE13 tumor cells (FIG. 12A). Determination of total tumor volume showed a similar reduction in PE13 breast tumor cells (FIG. 12B). Animals treated with 31M108 antibodies showed a significant reduction in total tumor volume compared to control treated animals (p<0.05). Further reduction was observed in animals treated with the antibody combination: treatment with NOTCH1 and NOTCH2 antibodies reduced tumor growth significant compared to treatment with either antibody alone (p<0.05) (FIG. 12B).

Example 8

Treatment of Human Cancer Using Anti-NOTCH1 Receptor Antibodies

This example describes methods for treating cancer using antibodies against a NOTCH1 receptor to target tumors comprising cancer stem cells and/or tumor cells in which NOTCH1 receptor expression has been detected.

The presence of cancer stem cell marker expression can first be determined from a tumor biopsy. Tumor cells from a biopsy from a patient diagnosed with cancer are removed under sterile conditions. In some embodiments, the tissue biopsy is fresh-frozen in liquid nitrogen, embedded in O.C.T., and cut on a cryostat as 10 um sections onto glass slides. Alternatively the tissue biopsy is formalin-fixed, paraffin-embedded, and cut on a microtome as 10 um section onto glass slides. Sections are incubated with antibodies against a NOTCH1 receptor to detect protein expression. Additionally, the presence of cancer stem cells can be determined. Tissue biopsy samples are cut up into small pieces, minced completely using sterile blades, and cells subject to enzymatic digestion and mechanical disruption to obtain a single cell suspension. Dissociated tumor cells are then incubated with anti-ESA, -CD44, -CD24, -Lin, and -NOTCH1 antibodies to detect cancer stem cells, and the presence of ESA+, CD44+, CD24-/low, Lin-, NOTCH1+ tumor stem cells is determined by flow cytometry as described in detail above.

Cancer patients whose tumors are diagnosed as expressing a NOTCH1 receptor are treated with anti-NOTCH1 receptor antibodies. Humanized or human monoclonal anti-NOTCH1 receptor antibodies generated as described above are purified and formulated with a suitable pharmaceutical carrier in PBS for injection. Patients are treated with the NOTCH1 antibodies once a week for at least 10 weeks, but in certain cases once a week for at least about 14 weeks. Each administration of the antibody should be a pharmaceutically effective dose about 2 to about 100 mg/ml and in certain cases between about 5 to about 40 mg/ml. The antibody can be administered prior to, concurrently with, or after standard radiotherapy regimens or chemotherapy regimens using one or more chemotherapeutic agent, such as oxaliplatin, fluorouracil, leucovorin, or streptozocin. Patients are monitored to determine whether such treatment has resulted in an anti-tumor response, for example, based on tumor regression, reduction in the incidences of new tumors, lower tumor antigen expression, decreased numbers of cancer stem cells, or other means of evaluating disease prognosis.

All publications and patents mentioned in the above specification are herein incorporated by reference. Various modifications and variations of the described method and system of the invention will be apparent to those in the art without departing from the scope and spirit of the invention. Although the invention has been described in connection with specific embodiments it should be understood that the invention as claimed should not be unduly limited to such specific embodiments. Indeed, various modifications of the described modes for carrying out the invention which are obvious to those in the relevant fields are intended to be within the scope of the following claims.

What is claimed is:

1. An isolated monoclonal antibody that specifically binds a non-ligand binding region of the extracellular domain of at least two human Notch receptors.

2. The antibody of claim 1, which specifically binds a non-ligand binding region of the extracellular domain of Notch2 and at least one additional human Notch receptor.

3. The antibody of claim 2, wherein the at least one additional human Notch receptor is Notch1, Notch3, and/or Notch4.

4. The antibody of claim 2, which binds Notch2 and Notch3.

5. The antibody of claim 1, which specifically binds a non-ligand binding region of the extracellular domain of Notch1 and at least one additional human Notch receptor.

6. The antibody of claim 5, wherein the at least one additional human Notch receptor is Notch2, Notch3, and/or Notch4.

7. The antibody of claim 1, wherein the antibody is a chimeric antibody.

8. The antibody of claim 1, wherein the antibody is a humanized antibody.

9. The antibody of claim 1, wherein the antibody is a human antibody.

10. The antibody of claim 1, wherein the non-ligand binding region comprises epidermal growth factor (EGF) repeats 1-10.

11. The antibody of claim 1, wherein the non-ligand binding region comprises EGF repeats 13-36.

12. A pharmaceutical composition comprising the antibody of claim 1.

* * * * *